(12) United States Patent
Van Dyk

(10) Patent No.: US 8,614,085 B2
(45) Date of Patent: Dec. 24, 2013

(54) YEAST WITH INCREASED BUTANOL TOLERANCE INVOLVING A MULTIDRUG EFFLUX PUMP GENE

(75) Inventor: Tina K. Van Dyk, Wilmington, DE (US)

(73) Assignee: Butamax(TM) Advanced Biofuels LLC, Wilmington, DE (US)

( * ) Notice: Subject to any disclaimer, the term of this patent is extended or adjusted under 35 U.S.C. 154(b) by 719 days.

(21) Appl. No.: 12/711,308

(22) Filed: Feb. 24, 2010

(65) Prior Publication Data

US 2010/0221801 A1 Sep. 2, 2010

Related U.S. Application Data

(60) Provisional application No. 61/156,067, filed on Feb. 27, 2009.

(51) Int. Cl.
| | | |
|---|---|---|
| *C12N 1/15* | (2006.01) | |
| *C12N 1/19* | (2006.01) | |
| *C12N 15/00* | (2006.01) | |
| *C12P 7/16* | (2006.01) | |
| *C07K 14/00* | (2006.01) | |
| *C07H 21/00* | (2006.01) | |
| *C12N 9/00* | (2006.01) | |
| *C12P 21/00* | (2006.01) | |

(52) U.S. Cl.
USPC ............. 435/254.2; 435/160; 435/320.1; 435/69.1; 435/440; 435/183; 530/350; 536/23.2

(58) Field of Classification Search
USPC .............. 435/254.2, 69.1, 320, 160, 440; 530/350; 536/23.1
See application file for complete search history.

(56) References Cited

U.S. PATENT DOCUMENTS

| | | | |
|---|---|---|---|
| 4,683,202 | A | 7/1987 | Mullis et al. |
| 2007/0031918 | A1 | 2/2007 | Dunson et al. |
| 2007/0092957 | A1 | 4/2007 | Donaldson et al. |
| 2007/0259410 | A1 | 11/2007 | Donaldson et al. |
| 2007/0292927 | A1 | 12/2007 | Donaldson et al. |
| 2008/0182308 | A1 | 7/2008 | Donaldson et al. |
| 2008/0261230 | A1 | 10/2008 | Liao et al. |
| 2009/0163376 | A1 | 6/2009 | Li et al. |
| 2009/0269823 | A1 | 10/2009 | Bramucci et al. |
| 2010/0081154 | A1 | 4/2010 | Flint et al. |

OTHER PUBLICATIONS

Leonard et al., Antimicrobial Agents and Chemotherapy 38(10):2492-2494, 1994.*
Dickinson et al., Journal of Biological Chemistry 273(40):25751-25756, 1998.*
Sousa et al., Microbiology 148(Pt5):1291-1303, 2002.*
Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Altschul et al., J. Mol. Biol., 215:403 410 (1990).
Ashe et al. The EMBO Journal (2001) 20:6464-6474.
Deshpande, Mukund V., Appl. Biochem. Biotechnol., 36:227, (1992).
Frohman et al., PNAS USA 85:8998 (1988).
Guo et al., J. Membr. Sci. 245, 199-210 (2004).
Loh et al., Science 243:217 (1989).
Lorenz et al. Molec. Biol. of the Cell (2000) 11:183-199.
Mnaimneh et al. (2004) Cell 118(1):31-44.
Ohara et al., PNAS USA 86:5673 (1989).
Sulter et al., Arch. Microbiol. 153:485 489 (1990).
Smirnova et al. Molecular and Cellular Bioloty (2005) 25:9340-9349.
Tabor, S. et al., Proc. Acad. Sci. USA 82:1074 (1985).
Van Ness and Chen, Nucl. Acids Res. 19:5143 5151 (1991).
Wach et al. (1994) Yeast 10:1793-1808.
Walker, et al., Proc. Natl. Acad. Sci. U.S.A., 89:392 (1992).
Watanabe et al. (2000) J Biosci Bioeng 89, 569-76.
Winzeler al. Science, 285:901-906, (1999).
Aden et al. Lignocellulosic Biomass to Ethanol Process Design and Economics Utilizing Co-Current Dilute Acid Prehydrolysis and Enzymatic Hydrolysis for Corn Stover, Report NREL/TP-510-32438, National Renewable Energy Laboratory, Jun. 2002.
Ausubel, F. M. et al., In Current Protocols in Molecular Biology, published by Greene Publishing and Wiley-Interscience, 1987.
Bellion et al., Microb. Growth C1 Compd., [Int. Symp.], 7th (1993), 415 32, Editor(s): Murrell, J. Collin; Kelly, Don P. Publisher: Intercept, Andover, UK.
Biocomputing: Informatics and Genome Projects (Smith, D. W., Ed.) Academic: NY (1993).
Thomas D. Brock in Biotechnology: A Textbook of Industrial Microbiology, Second Edition (1989) Sinauer Associates, Inc., Sunderland, MA.
Computer Analysis of Sequence Data, Part I (Griffin, A. M., and Griffin, H. G., Eds.) Humania: NJ (1994).
Computational Molecular Biology (Lesk, A. M., Ed.) Oxford University: NY (1988).
Doherty and Malone, Conceptual Design of Distillation Systems, McGraw Hill, New York, 2001.
Methods in Enzymology, v194, pp. 281-301 (1991).
Methods in Yeast Genetics, 2005, Cold Spring Harbor Laboratory Press, Cold Spring Harbor, NY.
Pearson, Comput. Methods Genome Res., [Proc. Int. Symp.] (1994), Meeting Date 1992, 111 20. Editor(s): Suhai, Sandor. Plenum: New York, NY.
Rychlik, W., In Methods in Molecular Biology, White, B. A. Ed., (1993) vol. 15, pp. 31 39, PCR Protocols: Current Methods and Applications, Humania: Totowa, NJ.

(Continued)

*Primary Examiner* — Delia Ramirez
(74) *Attorney, Agent, or Firm* — Christine M. Lhulier

(57) ABSTRACT

Increasing tolerance to butanol in yeast has been accomplished by decreasing activity of Pdr5p encoded by an endogenous PDR5 gene. A deletion mutation of the PDR5 gene led to improved growth yield in the presence of butanol. Yeast cells with reduced Pdr5p activity, or other multidrug resistance ATP-binding cassette transporter protein activity encoded by CDR1 or BFR1, and a butanol biosynthetic pathway may be used for improved butanol production.

5 Claims, No Drawings

(56) References Cited

OTHER PUBLICATIONS

Sambrook, J., Fritsch, E. F. and Maniatis, T. Molecular Cloning: A Laboratory Manual, 3rd ed., Cold Spring Harbor Laboratory: Cold Spring Harbor, NY (2001), particularly Chapter 11 and Table 11.1.
Sequence Analysis in Molecular Biology (von Heinje, G., Ed.) Academic (1987).
Sequence Analysis Primer (Gribskov, M. and Devereux, J., Eds.) Stockton: NY (1991).
Silhavy, T. J., Bennan, M. L. and Enquist, L. W. Experiments with Gene Fusions; Cold Spring Harbor Laboratory: Cold Spring Harbor, New York, 1984.
Spencer et al., Mutagenesis in Yeast, 1996, Yeast Protocols: Methods in Cell and Molecular Biology, Humana Press, Totowa, NJ.
Thein and Wallace, "The use of oligonucleotides as specific hybridization probes in the Diagnosis of Genetic Disorders", in Human Genetic Diseases: A Practical Approach, K. E. Davis Ed., (1986) pp. 33-50, IRL: Herndon, VA.
Yeast Protocols, Second Edition Wei Xiao, ed; Humana Press, Totowa, NJ (2006).
Anonymous: "Saccharomyces cerevisiae Meyen ex E.C. Hansen deposited as Saccharomyces cerevisiae Hansen, teleomorph (ATCC No. 4002409)" [Online] 1999, LGC/ATCC Standards.
Search Report and Written Opinion in corresponding PCT/US2010/025735 patent application mailed Jun. 14, 2010.

* cited by examiner

SEQUENCE LISTING

```
<160> NUMBER OF SEQ ID NOS: 65

<210> SEQ ID NO 1
<211> LENGTH: 1179
<212> TYPE: DNA
<213> ORGANISM: Clostridium acetobutylicum

<400> SEQUENCE: 1
atgaaagaag ttgtaatagc tagtgcagta agaacagcga ttggatctta tggaaagtct      60
cttaaggatg taccagcagt agatttagga gctacagcta taaggaagc agttaaaaaa     120 gcaggaataa aaccagagga tgttaatgaa gtcattttag gaaatgttct tcaagcaggt    180
ttaggacaga atccagcaag acaggcatct tttaaagcag gattaccagt tgaaattcca    240
gctatgacta ttaataaggt ttgtggttca ggacttagaa cagttagctt agcagcacaa    300
attataaaag caggagatgc tgacgtaata atagcaggtg gtatggaaaa tatgtctaga    360
```

```
gctccttact tagcgaataa cgctagatgg ggatatagaa tgggaaacgc taaatttgtt    420
gatgaaatga tcactgacgg attgtgggat gcatttaatg attaccacat gggaataaca    480
gcagaaaaca tagctgagag atggaacatt tcaagagaag aacaagatga gtttgctctt    540
gcatcacaaa aaaagctgaa gaagctata aaatcaggtc aatttaaaga tgaaatagtt     600
cctgtagtaa ttaaaggcag aaagggagaa actgtagttg atacagatga gcaccctaga    660
tttggatcaa ctatagaagg acttgcaaaa ttaaaacctg ccttcaaaaa agatggaaca    720
gttacagctg gtaatgcatc aggattaaat gactgtgcag cagtacttgt aatcatgagt    780
gcagaaaaag ctaaagagct tggagtaaaa ccacttgcta agatagtttc ttatggttca    840
gcaggagttg acccagcaat aatgggatat ggacctttct atgcaacaaa agcagctatt    900
gaaaaagcag gttggacagt tgatgaatta gatttaatag aatcaaatga agcttttgca    960
gctcaaagtt tagcagtagc aaaagattta aaatttgata tgaataaagt aaatgtaaat   1020
ggaggagcta ttgcccttgg tcatccaatt ggagcatcag gtgcaagaat actcgttact   1080
cttgtacacg caatgcaaaa aagagatgca aaaaaaggct tagcaacttt atgtataggt   1140
ggcggacaag gaacagcaat attgctagaa aagtgctag                          1179

<210> SEQ ID NO 2
<211> LENGTH: 392
<212> TYPE: PRT
<213> ORGANISM: Clostridium acetobutylicum

<400> SEQUENCE: 2

Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
                20                  25                  30

Ala Ile Lys Glu Ala Val Lys Lys Ala Gly Ile Lys Pro Glu Asp Val
            35                  40                  45

Asn Glu Val Ile Leu Gly Asn Val Leu Gln Ala Gly Leu Gly Gln Asn
        50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
                85                  90                  95

Leu Ala Ala Gln Ile Ile Lys Ala Gly Asp Ala Asp Val Ile Ile Ala
            100                 105                 110

Gly Gly Met Glu Asn Met Ser Arg Ala Pro Tyr Leu Ala Asn Asn Ala
        115                 120                 125

Arg Trp Gly Tyr Arg Met Gly Asn Ala Lys Phe Val Asp Glu Met Ile
    130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Glu Ala Ile Lys Ser
            180                 185                 190

Gly Gln Phe Lys Asp Glu Ile Val Pro Val Ile Lys Gly Arg Lys
        195                 200                 205

Gly Glu Thr Val Val Asp Thr Asp Glu His Pro Arg Phe Gly Ser Thr
    210                 215                 220

Ile Glu Gly Leu Ala Lys Leu Lys Pro Ala Phe Lys Lys Asp Gly Thr
225                 230                 235                 240
```

```
Val Thr Ala Gly Asn Ala Ser Gly Leu Asn Asp Cys Ala Ala Val Leu
            245                 250                 255

Val Ile Met Ser Ala Glu Lys Ala Lys Glu Leu Gly Val Lys Pro Leu
        260                 265                 270

Ala Lys Ile Val Ser Tyr Gly Ser Ala Gly Val Asp Pro Ala Ile Met
    275                 280                 285

Gly Tyr Gly Pro Phe Tyr Ala Thr Lys Ala Ala Ile Glu Lys Ala Gly
    290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
            325                 330                 335

Val Asn Val Asn Gly Gly Ala Ile Ala Leu Gly His Pro Ile Gly Ala
        340                 345                 350

Ser Gly Ala Arg Ile Leu Val Thr Leu Val His Ala Met Gln Lys Arg
    355                 360                 365

Asp Ala Lys Lys Gly Leu Ala Thr Leu Cys Ile Gly Gly Gly Gln Gly
    370                 375                 380

Thr Ala Ile Leu Leu Glu Lys Cys
385                 390

<210> SEQ ID NO 3
<211> LENGTH: 1179
<212> TYPE: DNA
<213> ORGANISM: Clostridium acetobutylicum

<400> SEQUENCE: 3
atgagagatg tagtaatagt aagtgctgta agaactgcaa taggagcata tggaaaaaca        60
ttaaaggatg tacctgcaac agagttagga gctatagtaa taaggaagc tgtaagaaga       120 gctaatataa atccaaatga gattaatgaa gttattttg gaaatgtact tcaagctgga       180
ttaggccaaa acccagcaag acaagcagca gtaaaagcag gattaccttt agaaacacct       240
gcgtttacaa tcaataaggt ttgtggttca ggtttaagat ctataagttt agcagctcaa       300
attataaaag ctggagatgc tgataccatt gtagtaggtg gtatggaaaa atatgtctaga      360 tcaccatatt tgattaacaa tcagagatgg ggtcaaagaa tgggagatag tgaattagtt       420
gatgaaatga taaaggatgg tttgtgggat gcatttaatg atatcatat gggagtaact        480 gcagaaaata ttgcagaaca atggaatata acaagagaag agcaagatga atttcactt        540 atgtcacaac aaaaagctga aaaagccatt aaaaatggag aatttaagga tgaaatagtt       600
cctgtattaa taaagactaa aaaaggtgaa atagtctttg atcaagatga atttcctaga       660
ttcggaaaca ctattgaagc attaagaaaa cttaaaccta ttttcaagga aatggtact        720 gttacagcag gtaatgcatc cggattaaat gatggagctg cagcactagt aataatgagc       780
gctgataaag ctaacgctct cggaataaaa ccacttgcta agattacttc ttacggatca       840 tatgggggtag atccatcaat aatgggatat ggagcttttt atgcaactaa agctgcctta       900
gataaaatta atttaaaacc tgaagactta gatttaattg aagctaacga ggcatatgct       960
tctcaaagta tagcagtaac tagagattta aatttagata tgagtaaagt taatgttaat      1020
ggtggagcta tagcacttgg acatccaata ggtgcatctg gtgcacgtat tttagtaaca      1080
ttactatacg ctatgcaaaa aagagattca aaaaaaggtc ttgctactct atgtattggt      1140
ggaggtcagg gaacagctct cgtagttgaa agagactaa                            1179
```

```
<210> SEQ ID NO 4
<211> LENGTH: 392
<212> TYPE: PRT
<213> ORGANISM: Clostridium acetobutylicum

<400> SEQUENCE: 4

Met Arg Asp Val Val Ile Val Ser Ala Val Arg Thr Ala Ile Gly Ala
1               5                   10                  15

Tyr Gly Lys Thr Leu Lys Asp Val Pro Ala Thr Glu Leu Gly Ala Ile
            20                  25                  30

Val Ile Lys Glu Ala Val Arg Ala Asn Ile Asn Pro Asn Glu Ile
        35                  40                  45

Asn Glu Val Ile Phe Gly Asn Val Leu Gln Ala Gly Leu Gly Gln Asn
    50                  55                  60

Pro Ala Arg Gln Ala Ala Val Lys Ala Gly Leu Pro Leu Glu Thr Pro
65                  70                  75                  80

Ala Phe Thr Ile Asn Lys Val Cys Gly Ser Gly Leu Arg Ser Ile Ser
                85                  90                  95

Leu Ala Ala Gln Ile Ile Lys Ala Gly Asp Ala Asp Thr Ile Val Val
            100                 105                 110

Gly Gly Met Glu Asn Met Ser Arg Ser Pro Tyr Leu Ile Asn Asn Gln
        115                 120                 125

Arg Trp Gly Gln Arg Met Gly Asp Ser Glu Leu Val Asp Glu Met Ile
130                 135                 140

Lys Asp Gly Leu Trp Asp Ala Phe Asn Gly Tyr His Met Gly Val Thr
145                 150                 155                 160

Ala Glu Asn Ile Ala Glu Gln Trp Asn Ile Thr Arg Glu Glu Gln Asp
                165                 170                 175

Glu Phe Ser Leu Met Ser Gln Gln Lys Ala Glu Lys Ala Ile Lys Asn
            180                 185                 190

Gly Glu Phe Lys Asp Glu Ile Val Pro Val Leu Ile Lys Thr Lys Lys
        195                 200                 205

Gly Glu Ile Val Phe Asp Gln Asp Glu Phe Pro Arg Phe Gly Asn Thr
    210                 215                 220

Ile Glu Ala Leu Arg Lys Leu Lys Pro Ile Phe Lys Glu Asn Gly Thr
225                 230                 235                 240

Val Thr Ala Gly Asn Ala Ser Gly Leu Asn Asp Gly Ala Ala Ala Leu
                245                 250                 255

Val Ile Met Ser Ala Asp Lys Ala Asn Ala Leu Gly Ile Lys Pro Leu
            260                 265                 270

Ala Lys Ile Thr Ser Tyr Gly Ser Tyr Gly Val Asp Pro Ser Ile Met
        275                 280                 285

Gly Tyr Gly Ala Phe Tyr Ala Thr Lys Ala Ala Leu Asp Lys Ile Asn
    290                 295                 300

Leu Lys Pro Glu Asp Leu Asp Leu Ile Glu Ala Asn Glu Ala Tyr Ala
305                 310                 315                 320

Ser Gln Ser Ile Ala Val Thr Arg Asp Leu Asn Leu Asp Met Ser Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Leu Tyr Ala Met Gln Lys Arg
        355                 360                 365
```

Asp Ser Lys Lys Gly Leu Ala Thr Leu Cys Ile Gly Gly Gln Gly
    370                 375                 380

Thr Ala Leu Val Val Glu Arg Asp
385                 390

<210> SEQ ID NO 5
<211> LENGTH: 849
<212> TYPE: DNA
<213> ORGANISM: Clostridium acetobutylicum

<400> SEQUENCE: 5

```
atgaaaaagg tatgtgttat aggtgcaggt actatgggtt caggaattgc tcaggcattt      60
gcagctaaag gatttgaagt agtattaaga gatattaaag atgaatttgt tgatagagga     120
ttagatttta tcaataaaaa tctttctaaa ttagttaaaa aggaaagat  agaagaagct     180
actaaagttg aaatcttaac tagaatttcc ggaacagttg accttaatat ggcagctgat     240
tgcgatttag ttatagaagc agctgttgaa agaatggata ttaaaaagca gattttttgct    300
gacttagaca atatatgcaa gccagaaaca attcttgcat caaatacatc atcactttca    360
ataacagaag tggcatcagc aactaaaaga cctgataagg ttataggtat gcatttctt     420
aatccagctc ctgttatgaa gcttgtagag gtaataagag aatagctac atcacaagaa     480
acttttgatg cagttaaaga gacatctata gcaataggaa aagatcctgt agaagtagca    540
gaagcaccag gatttgttgt aaatagaata ttaataccaa tgattaatga gcagttggt    600
atattagcag aaggaatagc ttcagtagaa gacatagata agctatgaa  acttggagct    660
aatcacccaa tgggaccatt agaattaggt gattttatag gtcttgatat atgtcttgct    720
ataatggatg tttatactc agaaactgga gattctaagt atagaccaca tacattactt    780
aagaagtatg taagagcagg atggcttgga agaaaatcag gaaaaggttt ctacgattat    840
tcaaaataa                                                             849
```

<210> SEQ ID NO 6
<211> LENGTH: 282
<212> TYPE: PRT
<213> ORGANISM: Clostridium acetobutylicum

<400> SEQUENCE: 6

Met Lys Lys Val Cys Val Ile Gly Ala Gly Thr Met Gly Ser Gly Ile
1               5                   10                  15

Ala Gln Ala Phe Ala Ala Lys Gly Phe Glu Val Val Leu Arg Asp Ile
            20                  25                  30

Lys Asp Glu Phe Val Asp Arg Gly Leu Asp Phe Ile Asn Lys Asn Leu
        35                  40                  45

Ser Lys Leu Val Lys Lys Gly Lys Ile Glu Glu Ala Thr Lys Val Glu
    50                  55                  60

Ile Leu Thr Arg Ile Ser Gly Thr Val Asp Leu Asn Met Ala Ala Asp
65                  70                  75                  80

Cys Asp Leu Val Ile Glu Ala Ala Val Glu Arg Met Asp Ile Lys Lys
                85                  90                  95

Gln Ile Phe Ala Asp Leu Asp Asn Ile Cys Lys Pro Glu Thr Ile Leu
            100                 105                 110

Ala Ser Asn Thr Ser Ser Leu Ser Ile Thr Glu Val Ala Ser Ala Thr
        115                 120                 125

Lys Arg Pro Asp Lys Val Ile Gly Met His Phe Phe Asn Pro Ala Pro
    130                 135                 140

```
Val Met Lys Leu Val Glu Val Ile Arg Gly Ile Ala Thr Ser Gln Glu
145                 150                 155                 160

Thr Phe Asp Ala Val Lys Glu Thr Ser Ile Ala Ile Gly Lys Asp Pro
                165                 170                 175

Val Glu Val Ala Glu Ala Pro Gly Phe Val Val Asn Arg Ile Leu Ile
                180                 185                 190

Pro Met Ile Asn Glu Ala Val Gly Ile Leu Ala Glu Gly Ile Ala Ser
            195                 200                 205

Val Glu Asp Ile Asp Lys Ala Met Lys Leu Gly Ala Asn His Pro Met
                210                 215                 220

Gly Pro Leu Glu Leu Gly Asp Phe Ile Gly Leu Asp Ile Cys Leu Ala
225                 230                 235                 240

Ile Met Asp Val Leu Tyr Ser Glu Thr Gly Asp Ser Lys Tyr Arg Pro
                245                 250                 255

His Thr Leu Leu Lys Lys Tyr Val Arg Ala Gly Trp Leu Gly Arg Lys
                260                 265                 270

Ser Gly Lys Gly Phe Tyr Asp Tyr Ser Lys
            275                 280

<210> SEQ ID NO 7
<211> LENGTH: 786
<212> TYPE: DNA
<213> ORGANISM: Clostridium acetobutylicum

<400> SEQUENCE: 7
atggaactaa acaatgtcat ccttgaaaag gaaggtaaag ttgctgtagt taccattaac    60
agacctaaag cattaaatgc gttaaatagt gatacactaa agaaatggga ttatgttata   120
ggtgaaattg aaaatgatag cgaagtactt gcagtaattt taactggagc aggagaaaaa   180
tcatttgtag caggagcaga tatttctgag atgaaggaaa tgaataccat tgaaggtaga   240
aaattcggga tacttggaaa taagtgtttt agaagattag aacttcttga aaagcctgta   300
atagcagctg ttaatggttt tgctttagga ggcggatgcg aaatagctat gtcttgtgat   360
ataagaatag cttcaagcaa cgcaagattt ggtcaaccag aagtaggtct cggaataaca   420
cctggttttg gtggtacaca aagactttca agattagttg gaatgggcat ggcaaagcag   480
cttatattta ctgcacaaaa tataaaggca gatgaagcat taagaatcgg acttgtaaat   540
aaggtagtag aacctagtga attaatgaat acagcaaaag aaattgcaaa caaaattgtg   600
agcaatgctc cagtagctgt taagttaagc aaacaggcta ttaatagagg aatgcagtgt   660
gatattgata ctgctttagc atttgaatca gaagcatttg gagaatgctt ttcaacagag   720
gatcaaaagg atgcaatgac agctttcata gagaaaagaa aaattgaagg cttcaaaaat   780
agatag                                                            786

<210> SEQ ID NO 8
<211> LENGTH: 261
<212> TYPE: PRT
<213> ORGANISM: Clostridium acetobutylicum

<400> SEQUENCE: 8

Met Glu Leu Asn Asn Val Ile Leu Glu Lys Glu Gly Lys Val Ala Val
1               5                   10                  15

Val Thr Ile Asn Arg Pro Lys Ala Leu Asn Ala Leu Asn Ser Asp Thr
                20                  25                  30

Leu Lys Glu Met Asp Tyr Val Ile Gly Glu Ile Glu Asn Asp Ser Glu
            35                  40                  45
```

```
Val Leu Ala Val Ile Leu Thr Gly Ala Gly Glu Lys Ser Phe Val Ala
 50                  55                  60
Gly Ala Asp Ile Ser Glu Met Lys Glu Met Asn Thr Ile Glu Gly Arg
 65                  70                  75                  80
Lys Phe Gly Ile Leu Gly Asn Lys Val Phe Arg Arg Leu Glu Leu Leu
                 85                  90                  95
Glu Lys Pro Val Ile Ala Ala Val Asn Gly Phe Ala Leu Gly Gly Gly
            100                 105                 110
Cys Glu Ile Ala Met Ser Cys Asp Ile Arg Ile Ala Ser Ser Asn Ala
            115                 120                 125
Arg Phe Gly Gln Pro Glu Val Gly Leu Gly Ile Thr Pro Gly Phe Gly
    130                 135                 140
Gly Thr Gln Arg Leu Ser Arg Leu Val Gly Met Gly Met Ala Lys Gln
145                 150                 155                 160
Leu Ile Phe Thr Ala Gln Asn Ile Lys Ala Asp Glu Ala Leu Arg Ile
                165                 170                 175
Gly Leu Val Asn Lys Val Val Glu Pro Ser Glu Leu Met Asn Thr Ala
            180                 185                 190
Lys Glu Ile Ala Asn Lys Ile Val Ser Asn Ala Pro Val Ala Val Lys
            195                 200                 205
Leu Ser Lys Gln Ala Ile Asn Arg Gly Met Gln Cys Asp Ile Asp Thr
    210                 215                 220
Ala Leu Ala Phe Glu Ser Glu Ala Phe Gly Glu Cys Phe Ser Thr Glu
225                 230                 235                 240
Asp Gln Lys Asp Ala Met Thr Ala Phe Ile Glu Lys Arg Lys Ile Glu
                245                 250                 255
Gly Phe Lys Asn Arg
            260

<210> SEQ ID NO 9
<211> LENGTH: 1197
<212> TYPE: DNA
<213> ORGANISM: Clostridium acetobutylicum

<400> SEQUENCE: 9
atgatagtaa aagcaaagtt tgtaaaagga tttatcagag atgtacatcc ttatggttgc      60
agaagggaag tactaaatca aatagattat tgtaagaagg ctattgggtt taggggacca     120
aagaaggttt taattgttgg agcctcatct gggtttggtc ttgctactag aatttcagtt     180
gcatttggag gtccagaagc tcacacaatt ggagtatcct atgaaacagg agctacagat     240
agaagaatag gaacagcggg atggtataat aacatatttt ttaaagaatt tgctaaaaaa     300
aaaggattag ttgcaaaaaa cttcattgag gatgcctttt ctaatgaaac caaagataaa     360
gttattaagt atataaagga tgaatttggt aaaatagatt tatttgttta gtttagct      420 gcgcctagga gaaaggacta taaaactgga atgttttata cttcaagaat aaaaacaatt     480
ttaggagatt ttgagggacc gactattgat gttgaaagag acgagattac tttaaaaaag     540
gttagtagtg ctagcattga agaaattgaa gaaactagaa aggtaatggg tggagaggat     600
tggcaagagt ggtgtgaaga gctgctttat gaagattgtt tttcggataa agcaactacc     660
atagcatact cgtatatagg atcccccaaga acctacaaga tatatagaga aggtactata     720
ggaatagcta aaaggatct tgaagataag gctaagctta taaatgaaaa acttaacaga     780
gttataggtg gtagagccttt tgtgtctgtg aataaagcat tagttacaaa agcaagtgca     840
tatattccaa ctttttcctct ttatgcagct atttttatata aggtcatgaa agaaaaaaat     900
```

```
attcatgaaa attgtattat gcaaattgag agaatgtttt ctgaaaaaat atattcaaat    960
gaaaaaatac aatttgatga caagggaaga ttaaggatgg acgatttaga gcttagaaaa   1020
gacgttcaag acgaagttga tagaatatgg agtaatatta ctcctgaaaa ttttaaggaa   1080
ttatctgatt ataagggata caaaaaagaa ttcatgaact taaacggttt tgatctagat   1140
ggggttgatt atagtaaaga cctggatata gaattattaa gaaaattaga accttaa     1197
```

<210> SEQ ID NO 10
<211> LENGTH: 398
<212> TYPE: PRT
<213> ORGANISM: Clostridium acetobutylicum

<400> SEQUENCE: 10

```
Met Ile Val Lys Ala Lys Phe Val Lys Gly Phe Ile Arg Asp Val His
1               5                   10                  15

Pro Tyr Gly Cys Arg Arg Glu Val Leu Asn Gln Ile Asp Tyr Cys Lys
            20                  25                  30

Lys Ala Ile Gly Phe Arg Gly Pro Lys Val Leu Ile Val Gly Ala
        35                  40                  45

Ser Ser Gly Phe Gly Leu Ala Thr Arg Ile Ser Val Ala Phe Gly Gly
    50                  55                  60

Pro Glu Ala His Thr Ile Gly Val Ser Tyr Glu Thr Gly Ala Thr Asp
65                  70                  75                  80

Arg Arg Ile Gly Thr Ala Gly Trp Tyr Asn Asn Ile Phe Phe Lys Glu
                85                  90                  95

Phe Ala Lys Lys Lys Gly Leu Val Ala Lys Asn Phe Ile Glu Asp Ala
            100                 105                 110

Phe Ser Asn Glu Thr Lys Asp Lys Val Ile Lys Tyr Ile Lys Asp Glu
        115                 120                 125

Phe Gly Lys Ile Asp Leu Phe Val Tyr Ser Leu Ala Ala Pro Arg Arg
    130                 135                 140

Lys Asp Tyr Lys Thr Gly Asn Val Tyr Thr Ser Arg Ile Lys Thr Ile
145                 150                 155                 160

Leu Gly Asp Phe Glu Gly Pro Thr Ile Asp Val Glu Arg Asp Glu Ile
                165                 170                 175

Thr Leu Lys Lys Val Ser Ser Ala Ser Ile Glu Glu Ile Glu Glu Thr
            180                 185                 190

Arg Lys Val Met Gly Gly Glu Asp Trp Gln Glu Trp Cys Glu Glu Leu
        195                 200                 205

Leu Tyr Glu Asp Cys Phe Ser Asp Lys Ala Thr Thr Ile Ala Tyr Ser
    210                 215                 220

Tyr Ile Gly Ser Pro Arg Thr Tyr Lys Ile Tyr Arg Glu Gly Thr Ile
225                 230                 235                 240

Gly Ile Ala Lys Lys Asp Leu Glu Asp Lys Ala Lys Leu Ile Asn Glu
                245                 250                 255

Lys Leu Asn Arg Val Ile Gly Gly Arg Ala Phe Val Ser Val Asn Lys
            260                 265                 270

Ala Leu Val Thr Lys Ala Ser Ala Tyr Ile Pro Thr Phe Pro Leu Tyr
        275                 280                 285

Ala Ala Ile Leu Tyr Lys Val Met Lys Glu Lys Asn Ile His Glu Asn
    290                 295                 300

Cys Ile Met Gln Ile Glu Arg Met Phe Ser Lys Ile Tyr Ser Asn
305                 310                 315                 320

Glu Lys Ile Gln Phe Asp Asp Lys Gly Arg Leu Arg Met Asp Asp Leu
                325                 330                 335
```

Glu Leu Arg Lys Asp Val Gln Asp Glu Val Asp Arg Ile Trp Ser Asn
            340                 345                 350

Ile Thr Pro Glu Asn Phe Lys Glu Leu Ser Asp Tyr Lys Gly Tyr Lys
        355                 360                 365

Lys Glu Phe Met Asn Leu Asn Gly Phe Asp Leu Asp Gly Val Asp Tyr
    370                 375                 380

Ser Lys Asp Leu Asp Ile Glu Leu Leu Arg Lys Leu Glu Pro
385                 390                 395

<210> SEQ ID NO 11
<211> LENGTH: 1407
<212> TYPE: DNA
<213> ORGANISM: Clostridium beijerinckii

<400> SEQUENCE: 11

| | | | | | |
|---|---|---|---|---|---|
| atgaataaag | acacactaat | acctacaact | aaagatttaa | aagtaaaaac | aaatggtgaa | 60 |
| aacattaatt | taaagaacta | caaggataat | tcttcatgtt | tcggagtatt | cgaaaatgtt | 120 |
| gaaaatgcta | taagcagcgc | tgtacacgca | caaaagatat | tatcccttca | ttatacaaaa | 180 |
| gagcaaagag | aaaaaatcat | aactgagata | agaaggccg | cattacaaaa | taagagggtc | 240 |
| ttggctacaa | tgattctaga | agaaacacat | atgggaagat | atgaggataa | aatattaaaa | 300 |
| catgaattgg | tagctaaata | tactcctggt | acagaagatt | taactactac | tgcttggtca | 360 |
| ggtgataatg | gtcttacagt | tgtagaaatg | tctccatatg | gtgttatagg | tgcaataact | 420 |
| ccttctacga | atccaactga | aactgtaata | tgtaatagca | taggcatgat | agctgctgga | 480 |
| aatgctgtag | tatttaacgg | acacccatgc | gctaaaaat | gtgttgcctt | tgctgttgaa | 540 |
| atgataaata | aggcaattat | ttcatgtggc | ggtcctgaaa | atctagtaac | aactataaaa | 600 |
| aatccaacta | tggagtctct | agatgcaatt | attaagcatc | cttcaataaa | acttctttgc | 660 |
| ggaactgggg | gtccaggaat | ggtaaaaacc | ctcttaaatt | ctggtaagaa | agctataggt | 720 |
| gctggtgctg | gaaatccacc | agttattgta | gatgatactg | ctgatataga | aaaggctggt | 780 |
| aggagcatca | ttgaaggctg | ttctttttgat | aataatttac | cttgtattgc | agaaaaagaa | 840 |
| gtatttgttt | ttgagaatgt | tgcagatgat | ttaatatcta | acatgctaaa | aaataatgct | 900 |
| gtaattataa | atgaagatca | agtatcaaaa | ttaatagatt | tagtattaca | aaaaaataat | 960 |
| gaaactcaag | aatactttat | aaacaaaaaa | tgggtaggaa | aagatgcaaa | attattctta | 1020 |
| gatgaaatag | atgttgagtc | tccttcaaat | gttaaatgca | taatctgcga | agtaaatgca | 1080 |
| aatcatccat | ttgttatgac | agaactcatg | atgccaatat | tgccaattgt | aagagttaaa | 1140 |
| gatatagatg | aagctattaa | atatgcaaag | atagcagaac | aaaatagaaa | acatagtgcc | 1200 |
| tatatttatt | ctaaaaatat | agacaaccta | aatagatttg | aaagagaaat | agatactact | 1260 |
| atttttgtaa | agaatgctaa | atcttttgct | ggtgttggtt | atgaagcaga | aggatttaca | 1320 |
| actttcacta | ttgctggatc | tactggtgag | ggaataacct | ctgcaaggaa | ttttacaaga | 1380 |
| caaagaagat | gtgtacttgc | cggctaa | | | | 1407 |

<210> SEQ ID NO 12
<211> LENGTH: 468
<212> TYPE: PRT
<213> ORGANISM: Clostridium beijerinckii

<400> SEQUENCE: 12

Met Asn Lys Asp Thr Leu Ile Pro Thr Thr Lys Asp Leu Lys Val Lys
1               5                   10                  15

```
Thr Asn Gly Glu Asn Ile Asn Leu Lys Asn Tyr Lys Asp Asn Ser Ser
            20                  25                  30

Cys Phe Gly Val Phe Glu Asn Val Glu Asn Ala Ile Ser Ser Ala Val
            35                  40                  45

His Ala Gln Lys Ile Leu Ser Leu His Tyr Thr Lys Glu Gln Arg Glu
 50                  55                  60

Lys Ile Ile Thr Glu Ile Arg Lys Ala Ala Leu Gln Asn Lys Glu Val
 65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
                100                 105                 110

Asp Leu Thr Thr Thr Ala Trp Ser Gly Asp Asn Gly Leu Thr Val Val
                115                 120                 125

Glu Met Ser Pro Tyr Gly Val Ile Gly Ala Ile Thr Pro Ser Thr Asn
        130                 135                 140

Pro Thr Glu Thr Val Ile Cys Asn Ser Ile Gly Met Ile Ala Ala Gly
145                 150                 155                 160

Asn Ala Val Val Phe Asn Gly His Pro Cys Ala Lys Lys Cys Val Ala
                165                 170                 175

Phe Ala Val Glu Met Ile Asn Lys Ala Ile Ile Ser Cys Gly Gly Pro
                180                 185                 190

Glu Asn Leu Val Thr Thr Ile Lys Asn Pro Thr Met Glu Ser Leu Asp
        195                 200                 205

Ala Ile Ile Lys His Pro Ser Ile Lys Leu Leu Cys Gly Thr Gly Gly
        210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Arg Ser Ile Ile Glu Gly Cys Ser Phe Asp Asn Asn
                260                 265                 270

Leu Pro Cys Ile Ala Glu Lys Glu Val Phe Val Phe Glu Asn Val Ala
                275                 280                 285

Asp Asp Leu Ile Ser Asn Met Leu Lys Asn Asn Ala Val Ile Ile Asn
        290                 295                 300

Glu Asp Gln Val Ser Lys Leu Ile Asp Leu Val Leu Gln Lys Asn Asn
305                 310                 315                 320

Glu Thr Gln Glu Tyr Phe Ile Asn Lys Lys Trp Val Gly Lys Asp Ala
                325                 330                 335

Lys Leu Phe Leu Asp Glu Ile Asp Val Glu Ser Pro Ser Asn Val Lys
                340                 345                 350

Cys Ile Ile Cys Glu Val Asn Ala Asn His Pro Phe Val Met Thr Glu
                355                 360                 365

Leu Met Met Pro Ile Leu Pro Ile Val Arg Val Lys Asp Ile Asp Glu
        370                 375                 380

Ala Ile Lys Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
                420                 425                 430

Gly Tyr Glu Ala Glu Gly Phe Thr Thr Phe Thr Ile Ala Gly Ser Thr
        435                 440                 445
```

```
Gly Glu Gly Ile Thr Ser Ala Arg Asn Phe Thr Arg Gln Arg Arg Cys
    450                 455                 460

Val Leu Ala Gly
465

<210> SEQ ID NO 13
<211> LENGTH: 1215
<212> TYPE: DNA
<213> ORGANISM: Clostridium acetobutylicum

<400> SEQUENCE: 13
atggttgatt tcgaatattc aataccaact agaatttttt tcggtaaaga taagataaat      60
gtacttggaa gagagcttaa aaaatatggt tctaaagtgc ttatagttta tggtggagga     120
agtataaaga gaaatggaat atatgataaa gctgtaagta tacttgaaaa aaacagtatt     180
aaattttatg aacttgcagg agtagagcca atccaagag taactacagt tgaaaaagga     240
gttaaaatat gtagagaaaa tggagttgaa gtagtactag ctataggtgg aggaagtgca     300
atagattgcg caaaggttat agcagcagca tgtgaatatg atggaaatcc atgggatatt     360
gtgttagatg ctcaaaaat aaaaagggtg cttcctatag ctagtatatt aaccattgct     420
gcaacaggat cagaaatgga tacgtgggca gtaataaata atatggatac aaacgaaaaa     480
ctaattgcgg cacatccaga tatggctcct aagttttcta tattagatcc aacgtatacg     540
tataccgtac ctaccaatca aacagcagca ggaacagctg atattatgag tcatatattt     600
gaggtgtatt ttagtaatac aaaaacagca tatttgcagg atagaatggc agaagcgtta     660
ttaagaactt gtattaaata tggaggaata gctcttgaga agccggatga ttatgaggca     720
agagccaatc taatgtgggc ttcaagtctt gcgataaatg acttttaac atatggtaaa     780 gacactaatt ggagtgtaca cttaatggaa catgaattaa gtgcttatta cgacataaca     840
cacggcgtag gcttgcaat tttaacacct aattggatgg agtatatttt aaataatgat     900
acagtgtaca gtttgttga atatggtgta atgtttggg aatagacaa agaaaaaat      960 cactatgaca tagcacatca agcaatacaa aaaacaagag attactttgt aaatgtacta    1020
ggtttaccat ctagactgag agatgttgga attgaagaag aaaaattgga cataatggca    1080
aaggaatcag taaagcttac aggaggaacc ataggaaacc taagaccagt aaacgcctcc    1140
gaagtcctac aaatattcaa aaaatctgtg taaaacgcct ccgaagtcct acaaatattc    1200
aaaaaatctg tgtaa                                                     1215

<210> SEQ ID NO 14
<211> LENGTH: 390
<212> TYPE: PRT
<213> ORGANISM: Clostridium acetobutylicum

<400> SEQUENCE: 14

Met Val Asp Phe Glu Tyr Ser Ile Pro Thr Arg Ile Phe Phe Gly Lys
1               5                   10                  15

Asp Lys Ile Asn Val Leu Gly Arg Glu Leu Lys Lys Tyr Gly Ser Lys
            20                  25                  30

Val Leu Ile Val Tyr Gly Gly Gly Ser Ile Lys Arg Asn Gly Ile Tyr
        35                  40                  45

Asp Lys Ala Val Ser Ile Leu Glu Lys Asn Ser Ile Lys Phe Tyr Glu
    50                  55                  60

Leu Ala Gly Val Glu Pro Asn Pro Arg Val Thr Thr Val Glu Lys Gly
65                  70                  75                  80
```

```
Val Lys Ile Cys Arg Glu Asn Gly Val Glu Val Leu Ala Ile Gly
             85                  90                  95
Gly Gly Ser Ala Ile Asp Cys Ala Lys Val Ile Ala Ala Cys Glu
            100                 105                 110
Tyr Asp Gly Asn Pro Trp Asp Ile Val Leu Asp Gly Ser Lys Ile Lys
        115                 120                 125
Arg Val Leu Pro Ile Ala Ser Ile Leu Thr Ile Ala Ala Thr Gly Ser
        130                 135                 140
Glu Met Asp Thr Trp Ala Val Ile Asn Asn Met Asp Thr Asn Glu Lys
145                 150                 155                 160
Leu Ile Ala Ala His Pro Asp Met Ala Pro Lys Phe Ser Ile Leu Asp
                165                 170                 175
Pro Thr Tyr Thr Tyr Thr Val Pro Thr Asn Gln Thr Ala Ala Gly Thr
            180                 185                 190
Ala Asp Ile Met Ser His Ile Phe Glu Val Tyr Phe Ser Asn Thr Lys
        195                 200                 205
Thr Ala Tyr Leu Gln Asp Arg Met Ala Glu Ala Leu Leu Arg Thr Cys
        210                 215                 220
Ile Lys Tyr Gly Gly Ile Ala Leu Glu Lys Pro Asp Asp Tyr Glu Ala
225                 230                 235                 240
Arg Ala Asn Leu Met Trp Ala Ser Ser Leu Ala Ile Asn Gly Leu Leu
                245                 250                 255
Thr Tyr Gly Lys Asp Thr Asn Trp Ser Val His Leu Met Glu His Glu
            260                 265                 270
Leu Ser Ala Tyr Tyr Asp Ile Thr His Gly Val Gly Leu Ala Ile Leu
        275                 280                 285
Thr Pro Asn Trp Met Glu Tyr Ile Leu Asn Asn Asp Thr Val Tyr Lys
        290                 295                 300
Phe Val Glu Tyr Gly Val Asn Val Trp Gly Ile Asp Lys Glu Lys Asn
305                 310                 315                 320
His Tyr Asp Ile Ala His Gln Ala Ile Gln Lys Thr Arg Asp Tyr Phe
                325                 330                 335
Val Asn Val Leu Gly Leu Pro Ser Arg Leu Arg Asp Val Gly Ile Glu
            340                 345                 350
Glu Glu Lys Leu Asp Ile Met Ala Lys Glu Ser Val Lys Leu Thr Gly
        355                 360                 365
Gly Thr Ile Gly Asn Leu Arg Pro Val Asn Ala Ser Glu Val Leu Gln
        370                 375                 380
Ile Phe Lys Lys Ser Val
385                 390

<210> SEQ ID NO 15
<211> LENGTH: 1170
<212> TYPE: DNA
<213> ORGANISM: Clostridium acetobutylicum

<400> SEQUENCE: 15
atgctaagtt ttgattattc aataccaact aaagttttt ttggaaaagg aaaaatagac      60
gtaattggag aagaaattaa gaaatatggc tcaagagtgc ttatagttta tggcggagga     120
agtataaaaa ggaacggtat atatgataga gcaacagcta tattaaaaga aaacaatata     180
gctttctatg aactttcagg agtagagcca atcctagga taacaacagt aaaaaaaggc     240
atagaaatat gtagagaaaa taatgtggat ttagtattag caataggggg aggaagtgca     300
atagactgtt ctaaggtaat tgcagctgga gtttattatg atggcgatac atgggacatg     360
```

-continued

```
gttaaagatc catctaaaat aactaaagtt cttccaattg caagtatact tactctttca    420
gcaacagggt ctgaaatgga tcaaattgca gtaatttcaa atatggagac taatgaaaag    480
cttggagtag acatgatga tatgagacct aaattttcag tgttagatcc tacatatact    540
tttacagtac ctaaaaatca aacagcagcg ggaacagctg acattatgag tcacaccttt    600
gaatcttact ttagtggtgt tgaaggtgct tatgtgcagg acggtatagc agaagcaatc    660
ttaagaacat gtataaagta tggaaaaata gcaatggaga agactgatga ttacgaggct    720
agagctaatt tgatgtgggc ttcaagttta gctataaatg gtctattatc acttggtaag    780
gatagaaaat ggagttgtca tcctatggaa cacgagttaa gtgcatatta tgatataaca    840
catggtgtag acttgcaat tttaacacct aattggatgg aatatattct aaatgacgat    900
acacttcata aatttgtttc ttatggaata aatgtttggg aatagacaa gaacaaagat    960 aactatgaaa tagcacgaga ggctattaaa aatacgagag aatactttaa ttcattgggt   1020
attccttcaa agcttagaga agttggaata ggaaaagata actagaact aatggcaaag   1080 caagctgtta gaaattctgg aggaacaata ggaagtttaa gaccaataaa tgcagaggat   1140
gttcttgaga tatttaaaaa atcttattaa                                    1170
```

<210> SEQ ID NO 16
<211> LENGTH: 389
<212> TYPE: PRT
<213> ORGANISM: Clostridium acetobutylicum

<400> SEQUENCE: 16

```
Met Leu Ser Phe Asp Tyr Ser Ile Pro Thr Lys Val Phe Phe Gly Lys
1               5                   10                  15

Gly Lys Ile Asp Val Ile Gly Glu Glu Ile Lys Lys Tyr Gly Ser Arg
            20                  25                  30

Val Leu Ile Val Tyr Gly Gly Gly Ser Ile Lys Arg Asn Gly Ile Tyr
        35                  40                  45

Asp Arg Ala Thr Ala Ile Leu Lys Glu Asn Asn Ile Ala Phe Tyr Glu
    50                  55                  60

Leu Ser Gly Val Glu Pro Asn Pro Arg Ile Thr Thr Val Lys Lys Gly
65                  70                  75                  80

Ile Glu Ile Cys Arg Glu Asn Asn Val Asp Leu Val Leu Ala Ile Gly
                85                  90                  95

Gly Gly Ser Ala Ile Asp Cys Ser Lys Val Ile Ala Ala Gly Val Tyr
            100                 105                 110

Tyr Asp Gly Asp Thr Trp Asp Met Val Lys Asp Pro Ser Lys Ile Thr
        115                 120                 125

Lys Val Leu Pro Ile Ala Ser Ile Leu Thr Leu Ser Ala Thr Gly Ser
    130                 135                 140

Glu Met Asp Gln Ile Ala Val Ile Ser Asn Met Glu Thr Asn Glu Lys
145                 150                 155                 160

Leu Gly Val Gly His Asp Asp Met Arg Pro Lys Phe Ser Val Leu Asp
                165                 170                 175

Pro Thr Tyr Thr Phe Thr Val Pro Lys Asn Gln Thr Ala Ala Gly Thr
            180                 185                 190

Ala Asp Ile Met Ser His Thr Phe Glu Ser Tyr Phe Ser Gly Val Glu
        195                 200                 205

Gly Ala Tyr Val Gln Asp Gly Ile Ala Glu Ala Ile Leu Arg Thr Cys
    210                 215                 220

Ile Lys Tyr Gly Lys Ile Ala Met Glu Lys Thr Asp Asp Tyr Glu Ala
225                 230                 235                 240
```

```
Arg Ala Asn Leu Met Trp Ala Ser Ser Leu Ala Ile Asn Gly Leu Leu
                245                 250                 255

Ser Leu Gly Lys Asp Arg Lys Trp Ser Cys His Pro Met Glu His Glu
            260                 265                 270

Leu Ser Ala Tyr Tyr Asp Ile Thr His Gly Val Gly Leu Ala Ile Leu
                275                 280                 285

Thr Pro Asn Trp Met Glu Tyr Ile Leu Asn Asp Asp Thr Leu His Lys
        290                 295                 300

Phe Val Ser Tyr Gly Ile Asn Val Trp Gly Ile Asp Lys Asn Lys Asp
305                 310                 315                 320

Asn Tyr Glu Ile Ala Arg Glu Ala Ile Lys Asn Thr Arg Glu Tyr Phe
                325                 330                 335

Asn Ser Leu Gly Ile Pro Ser Lys Leu Arg Glu Val Gly Ile Gly Lys
            340                 345                 350

Asp Lys Leu Glu Leu Met Ala Lys Gln Ala Val Arg Asn Ser Gly Gly
        355                 360                 365

Thr Ile Gly Ser Leu Arg Pro Ile Asn Ala Glu Asp Val Leu Glu Ile
    370                 375                 380

Phe Lys Lys Ser Tyr
385

<210> SEQ ID NO 17
<211> LENGTH: 780
<212> TYPE: DNA
<213> ORGANISM: Klebsiella pneumoniae

<400> SEQUENCE: 17
atgaatcatt ctgctgaatg cacctgcgaa gagagtctat gcgaaaccct gcgggcgttt      60
tccgcgcagc atcccgagag cgtgctctat cagacatcgc tcatgagcgc cctgctgagc     120
ggggtttacg aaggcagcac caccatcgcg gacctgctga acacggcga tttcggcctc     180 ggcacctta atgagctgga cggggagctg atcgccttca gcagtcaggt ctatcagctg     240
cgcgccgacg gcagcgcgcg caaagcccag ccggagcaga aaacgccgtt cgcggtgatg     300
acctggttcc agccgcagta ccggaaaacc tttgaccatc cggtgagccg ccagcagctg     360
cacgaggtga tcgaccagca aatcccctct gacaacctgt tctgcgccct gcgcatcgac     420
ggccatttcc gccatgccca tacccgcacc gtgccgcgcc agacgccgcc gtaccgggcg     480
atgaccgacg tcctcgacga tcagccggtg ttccgcttta accagcgcga aggggtgctg     540
gtcggcttcc ggaccccgca gcatatgcag gggatcaacg tcgccgggta tcacgagcac     600
tttattaccg atgaccgcaa aggcggcggt cacctgctgg attaccagct cgaccatggg     660
gtgctgacct tcggcgaaat tcacaagctg atgatcgacc tgcccgccga cagcgcgttc     720
ctgcaggcta atctgcatcc cgataatctc gatgccgcca tccgttccgt agaaagttaa     780

<210> SEQ ID NO 18
<211> LENGTH: 259
<212> TYPE: PRT
<213> ORGANISM: Klebsiella pneumoniae

<400> SEQUENCE: 18

Met Asn His Ser Ala Glu Cys Thr Cys Glu Glu Ser Leu Cys Glu Thr
1               5                   10                  15

Leu Arg Ala Phe Ser Ala Gln His Pro Glu Ser Val Leu Tyr Gln Thr
            20                  25                  30

Ser Leu Met Ser Ala Leu Leu Ser Gly Val Tyr Glu Gly Ser Thr Thr
```

```
                    35                  40                  45
Ile Ala Asp Leu Leu Lys His Gly Asp Phe Gly Leu Gly Thr Phe Asn
 50                  55                  60

Glu Leu Asp Gly Glu Leu Ile Ala Phe Ser Ser Gln Val Tyr Gln Leu
 65                  70                  75                  80

Arg Ala Asp Gly Ser Ala Arg Lys Ala Gln Pro Glu Gln Lys Thr Pro
                 85                  90                  95

Phe Ala Val Met Thr Trp Phe Gln Pro Gln Tyr Arg Lys Thr Phe Asp
                100                 105                 110

His Pro Val Ser Arg Gln Gln Leu His Glu Val Ile Asp Gln Gln Ile
            115                 120                 125

Pro Ser Asp Asn Leu Phe Cys Ala Leu Arg Ile Asp Gly His Phe Arg
130                 135                 140

His Ala His Thr Arg Thr Val Pro Arg Gln Thr Pro Pro Tyr Arg Ala
145                 150                 155                 160

Met Thr Asp Val Leu Asp Asp Gln Pro Val Phe Arg Phe Asn Gln Arg
                165                 170                 175

Glu Gly Val Leu Val Gly Phe Arg Thr Pro Gln His Met Gln Gly Ile
            180                 185                 190

Asn Val Ala Gly Tyr His Glu His Phe Ile Thr Asp Asp Arg Lys Gly
        195                 200                 205

Gly Gly His Leu Leu Asp Tyr Gln Leu Asp His Gly Val Leu Thr Phe
    210                 215                 220

Gly Glu Ile His Lys Leu Met Ile Asp Leu Pro Ala Asp Ser Ala Phe
225                 230                 235                 240

Leu Gln Ala Asn Leu His Pro Asp Asn Leu Asp Ala Ala Ile Arg Ser
                245                 250                 255

Val Glu Ser

<210> SEQ ID NO 19
<211> LENGTH: 1680
<212> TYPE: DNA
<213> ORGANISM: Klebsiella pneumoniae

<400> SEQUENCE: 19
atggacaaac agtatccggt acgccagtgg gcgcacggcg ccgatctcgt cgtcagtcag    60
ctggaagctc agggagtacg ccaggtgttc ggcatcccg gcgccaaaat tgacaaggtc   120
ttcgactcac tgctggattc ctcgattcgc attattccgg tacgcacga agccaacgcc   180 gcgtttatgg ccgccgccgt cggacgcatt accggcaaag cgggcgtggc gctggtcacc   240
tccggtccgg gctgttccaa cctgatcacc ggcatggcca ccgcgaacag cgaaggcgac   300
ccggtggtgg ccctgggcgg cgcggtaaaa cgcgccgata aagcgaagca ggtccaccag   360
agtatggata cggtggcgat gttcagcccg gtcaccaaat acgccgtcga ggtgacggcg   420
ccggatgcgc tggcggaagt ggtctccaac gccttccgcg ccgccgagca gggccggccg   480
ggcagcgcgt tcgttagcct gccgcaggat gtggtcgatg cccggtcag cggcaaagtg   540 ctgccggcca gcggggcccc gcagatgggc gccgcgccgg atgatgccat cgaccaggtg   600
gcgaagctta tcgcccaggc gaagaacccg atcttcctgc tcggcctgat ggccagccag   660
ccggaaaaca gcaaggcgct cgccgtttg ctggagacca ccatattcc agtcaccagc   720 acctatcagg ccgccggagc ggtgaatcag ataacttct ctcgcttcgc cggccgggtt   780
gggctgttta caaccaggc cggggaccgt ctgctgcagc tcgccgacct ggtgatctgc   840
atcggctaca gcccggtgga atacgaaccg gcgatgtgga acagcggcaa cgcgacgctg   900
```

```
gtgcacatcg acgtgctgcc cgcctatgaa gagcgcaact acaccccgga tgtcgagctg     960
gtgggcgata tcgccggcac tctcaacaag ctggcgcaaa atatcgatca tcggctggtg    1020
ctctccccgc aggcggcgga gatcctccgc gaccgccagc accagcgcga gctgctggac    1080
cgccgcggcg cgcagctgaa ccagtttgcc ctgcatccgc tgcgcatcgt tcgcgccatg    1140
caggacatcg tcaacagcga cgtcacgttg accgtggaca tgggcagctt ccatatctgg    1200
attgcccgct acctgtacag cttccgcgcc cgtcaggtga tgatctccaa cggccagcag    1260
accatgggcg tcgccctgcc ctgggctatc ggcgcctggc tggtcaatcc tgagcgaaaa    1320
gtggtctccg tctccggcga cggcggcttc ctgcagtcga gcatggagct ggagaccgcc    1380
gtccgcctga agccaacgt actgcacctg atctgggtcg ataacggcta caacatggtg    1440
gccattcagg aagagaaaaa ataccagcgc ctgtccggcg tcgagttcgg gccgatggat    1500
tttaaagcct atgccgaatc cttcggcgcg aaagggtttg ccgtggaaag cgccgaggcg    1560
ctggagccga ccctgcacgc ggcgatggac gtcgacggcc cggcggtggt ggccattccg    1620
gtggattatc gcgataaccc gctgctgatg ggccagctgc atctgagtca gattctgtaa    1680
```

<210> SEQ ID NO 20
<211> LENGTH: 559
<212> TYPE: PRT
<213> ORGANISM: Klebsiella pneumoniae

<400> SEQUENCE: 20

```
Met Asp Lys Gln Tyr Pro Val Arg Gln Trp Ala His Gly Ala Asp Leu
1               5                   10                  15

Val Val Ser Gln Leu Glu Ala Gln Gly Val Arg Gln Val Phe Gly Ile
                20                  25                  30

Pro Gly Ala Lys Ile Asp Lys Val Phe Asp Ser Leu Leu Asp Ser Ser
            35                  40                  45

Ile Arg Ile Ile Pro Val Arg His Glu Ala Asn Ala Ala Phe Met Ala
        50                  55                  60

Ala Ala Val Gly Arg Ile Thr Gly Lys Ala Gly Val Ala Leu Val Thr
65                  70                  75                  80

Ser Gly Pro Gly Cys Ser Asn Leu Ile Thr Gly Met Ala Thr Ala Asn
                85                  90                  95

Ser Glu Gly Asp Pro Val Val Ala Leu Gly Gly Ala Val Lys Arg Ala
            100                 105                 110

Asp Lys Ala Lys Gln Val His Gln Ser Met Asp Thr Val Ala Met Phe
        115                 120                 125

Ser Pro Val Thr Lys Tyr Ala Val Glu Val Thr Ala Pro Asp Ala Leu
    130                 135                 140

Ala Glu Val Val Ser Asn Ala Phe Arg Ala Ala Glu Gln Gly Arg Pro
145                 150                 155                 160

Gly Ser Ala Phe Val Ser Leu Pro Gln Asp Val Asp Gly Pro Val
                165                 170                 175

Ser Gly Lys Val Leu Pro Ala Ser Gly Ala Pro Gln Met Gly Ala Ala
            180                 185                 190

Pro Asp Asp Ala Ile Asp Gln Val Ala Lys Leu Ile Ala Gln Ala Lys
        195                 200                 205

Asn Pro Ile Phe Leu Leu Gly Leu Met Ala Ser Gln Pro Glu Asn Ser
    210                 215                 220

Lys Ala Leu Arg Arg Leu Leu Glu Thr Ser His Ile Pro Val Thr Ser
225                 230                 235                 240
```

```
Thr Tyr Gln Ala Ala Gly Ala Val Asn Gln Asp Asn Phe Ser Arg Phe
                245                 250                 255

Ala Gly Arg Val Gly Leu Phe Asn Asn Gln Ala Gly Asp Arg Leu Leu
            260                 265                 270

Gln Leu Ala Asp Leu Val Ile Cys Ile Gly Tyr Ser Pro Val Glu Tyr
        275                 280                 285

Glu Pro Ala Met Trp Asn Ser Gly Asn Ala Thr Leu Val His Ile Asp
    290                 295                 300

Val Leu Pro Ala Tyr Glu Glu Arg Asn Tyr Thr Pro Asp Val Glu Leu
305                 310                 315                 320

Val Gly Asp Ile Ala Gly Thr Leu Asn Lys Leu Ala Gln Asn Ile Asp
                325                 330                 335

His Arg Leu Val Leu Ser Pro Gln Ala Ala Glu Ile Leu Arg Asp Arg
            340                 345                 350

Gln His Gln Arg Glu Leu Leu Asp Arg Arg Gly Ala Gln Leu Asn Gln
        355                 360                 365

Phe Ala Leu His Pro Leu Arg Ile Val Arg Ala Met Gln Asp Ile Val
    370                 375                 380

Asn Ser Asp Val Thr Leu Thr Val Asp Met Gly Ser Phe His Ile Trp
385                 390                 395                 400

Ile Ala Arg Tyr Leu Tyr Ser Phe Arg Ala Arg Gln Val Met Ile Ser
                405                 410                 415

Asn Gly Gln Gln Thr Met Gly Val Ala Leu Pro Trp Ala Ile Gly Ala
            420                 425                 430

Trp Leu Val Asn Pro Glu Arg Lys Val Val Ser Val Ser Gly Asp Gly
        435                 440                 445

Gly Phe Leu Gln Ser Ser Met Glu Leu Glu Thr Ala Val Arg Leu Lys
    450                 455                 460

Ala Asn Val Leu His Leu Ile Trp Val Asp Asn Gly Tyr Asn Met Val
465                 470                 475                 480

Ala Ile Gln Glu Glu Lys Lys Tyr Gln Arg Leu Ser Gly Val Glu Phe
                485                 490                 495

Gly Pro Met Asp Phe Lys Ala Tyr Ala Glu Ser Phe Gly Ala Lys Gly
            500                 505                 510

Phe Ala Val Glu Ser Ala Glu Ala Leu Glu Pro Thr Leu His Ala Ala
        515                 520                 525

Met Asp Val Asp Gly Pro Ala Val Val Ala Ile Pro Val Asp Tyr Arg
    530                 535                 540

Asp Asn Pro Leu Leu Met Gly Gln Leu His Leu Ser Gln Ile Leu
545                 550                 555

<210> SEQ ID NO 21
<211> LENGTH: 771
<212> TYPE: DNA
<213> ORGANISM: Klebsiella pneumoniae

<400> SEQUENCE: 21
atgaaaaaag tcgcacttgt taccggcgcc ggccagggga ttggtaaagc tatcgccctt      60
cgtctggtga aggatggatt tgccgtggcc attgccgatt ataacgacgc caccgccaaa     120
gcggtcgcct cggaaatcaa ccaggccggc ggacacgccg tggcggtgaa agtggatgtc     180
tccgaccgcg atcaggtatt tgccgccgtt gaacaggcgc gcaaaacgct gggcggcttc     240
gacgtcatcg tcaataacgc cggtgtggca ccgtctacgc cgatcgagtc cattaccccg     300
gagattgtcg acaaagtcta caacatcaac gtcaaagggg tgatctgggg tattcaggcg     360
```

```
gcggtcgagg cctttaagaa agaggggcac ggcgggaaaa tcatcaacgc ctgttcccag    420
gccggccacg tcggcaaccc ggagctggcg gtgtatagct ccagtaaatt cgcggtacgc    480
ggcttaaccc agaccgccgc tcgcgacctc gcgccgctgg gcatcacggt caacggctac    540
tgcccgggga ttgtcaaaac gccaatgtgg gccgaaattg accgccaggt gtccgaagcc    600
gccggtaaac cgctgggcta cggtaccgcc gagttcgcca acgcatcac tctcggtcgt     660 ctgtccgagc cggaagatgt cgccgcctgc gtctcctatc ttgccagccc ggattctgat    720
tacatgaccg gtcagtcgtt gctgatcgac ggcgggatgg tatttaacta a             771
```

<210> SEQ ID NO 22
<211> LENGTH: 256
<212> TYPE: PRT
<213> ORGANISM: Klebsiella pneumoniae

<400> SEQUENCE: 22

```
Met Lys Lys Val Ala Leu Val Thr Gly Ala Gly Gln Gly Ile Gly Lys
1               5                   10                  15

Ala Ile Ala Leu Arg Leu Val Lys Asp Gly Phe Ala Val Ala Ile Ala
            20                  25                  30

Asp Tyr Asn Asp Ala Thr Ala Lys Ala Val Ala Ser Glu Ile Asn Gln
        35                  40                  45

Ala Gly Gly His Ala Val Ala Val Lys Val Asp Val Ser Asp Arg Asp
    50                  55                  60

Gln Val Phe Ala Ala Val Glu Gln Ala Arg Lys Thr Leu Gly Gly Phe
65                  70                  75                  80

Asp Val Ile Val Asn Asn Ala Gly Val Ala Pro Ser Thr Pro Ile Glu
                85                  90                  95

Ser Ile Thr Pro Glu Ile Val Asp Lys Val Tyr Asn Ile Asn Val Lys
            100                 105                 110

Gly Val Ile Trp Gly Ile Gln Ala Ala Val Glu Ala Phe Lys Lys Glu
        115                 120                 125

Gly His Gly Gly Lys Ile Ile Asn Ala Cys Ser Gln Ala Gly His Val
    130                 135                 140

Gly Asn Pro Glu Leu Ala Val Tyr Ser Ser Ser Lys Phe Ala Val Arg
145                 150                 155                 160

Gly Leu Thr Gln Thr Ala Ala Arg Asp Leu Ala Pro Leu Gly Ile Thr
                165                 170                 175

Val Asn Gly Tyr Cys Pro Gly Ile Val Lys Thr Pro Met Trp Ala Glu
            180                 185                 190

Ile Asp Arg Gln Val Ser Glu Ala Ala Gly Lys Pro Leu Gly Tyr Gly
        195                 200                 205

Thr Ala Glu Phe Ala Lys Arg Ile Thr Leu Gly Arg Leu Ser Glu Pro
    210                 215                 220

Glu Asp Val Ala Ala Cys Val Ser Tyr Leu Ala Ser Pro Asp Ser Asp
225                 230                 235                 240

Tyr Met Thr Gly Gln Ser Leu Leu Ile Asp Gly Gly Met Val Phe Asn
                245                 250                 255
```

<210> SEQ ID NO 23
<211> LENGTH: 1665
<212> TYPE: DNA
<213> ORGANISM: Klebsiella oxytoca

<400> SEQUENCE: 23

```
atgagatcga aaagatttga agcactggcg aaacgccctg tgaatcagga cggcttcgtt    60
```

```
aaggagtgga tcgaagaagg ctttatcgcg atggaaagcc cgaacgaccc aaaaccgtcg    120
attaaaatcg ttaacggcgc ggtgaccgag ctggacggga aaccggtaag cgattttgac    180
ctgatcgacc actttatcgc ccgctacggt atcaacctga accgcgccga agaagtgatg    240
gcgatggatt cggtcaagct ggccaacatg ctgtgcgatc cgaacgttaa acgcagcgaa    300
atcgtcccgc tgaccaccgc gatgacgccg gcgaaaattg tcgaagtggt ttcgcatatg    360
aacgtcgtcg agatgatgat ggcgatgcag aaaatgcgcg cccgccgcac cccgtcccag    420
caggcgcacg tcaccaacgt caaagataac ccggtacaga ttgccgccga cgccgccgaa    480
ggggcatggc gcggatttga cgaacaggaa accaccgttg cggtagcgcg ctatgcgccg    540
ttcaacgcca tcgcgctgct ggtgggctcg caggtaggcc gtccgggcgt gctgacgcag    600
tgctcgctgg aagaagccac cgagctgaag ctcggcatgc tgggccacac ctgctacgcc    660
gaaaccatct ccgtctacgg caccgagccg gtctttaccg acggcgacga cacgccgtgg    720
tcgaagggct tcctcgcctc gtcctacgcc tctcgcgggc tgaaaatgcg ctttacctcc    780
ggctccggct cggaagtgca gatgggctac gccgaaggca atccatgct ttatctggaa    840 gcgcgctgca tctacatcac caaagccgcg ggcgtacagg tcgtgcaaaa cggttccgta    900
agctgcatcg gcgtgccgtc tgcggtgcct tccggcattc gcgcggtgct ggcggaaaac    960
ctgatctgtt cgtcgctgga tctggagtgc gcctccagca acgaccagac cttcacccac   1020
tccgatatgc gtcgtaccgc gcgcctgctg atgcagttcc tgccgggcac cgactttatc   1080
tcctccggtt attccgcggt gccgaactac gacaacatgt tcgccggctc caacgaagat   1140
gccgaagact ttgacgacta caacgtcatc cagcgcgacc tgaaggtgga cggcggtttg   1200
cgtccggttc gcgaagagga cgtcatcgcc atccgtaaca agccgcccg cgcgctgcag   1260 gccgtgtttg ccggaatggg gctgccgccg attaccgatg aagaagttga agccgcgacc   1320 tacgccacg gttcgaaaga tatgccgagc gcaacatcg tcgaagacat caagttcgcc   1380
caggaaatca tcaataaaaa ccgcaacggt ctggaagtgg tgaaagcgct ggcgcagggc   1440
ggattcaccg acgtggccca ggacatgctc aacatccaga aagctaagct gaccggggac   1500
tacctgcata cctccgcgat tatcgtcggc gacgggcagg tgctgtcagc cgtcaacgac   1560
gtcaacgact atgccggtcc ggcaacgggc tatcgcctgc agggcgaacg ctgggaagag   1620
attaaaaaca tccctggcgc tcttgatccc aacgagattg attaa                   1665
```

<210> SEQ ID NO 24
<211> LENGTH: 554
<212> TYPE: PRT
<213> ORGANISM: Klebsiella oxytoca

<400> SEQUENCE: 24

Met Arg Ser Lys Arg Phe Glu Ala Leu Ala Lys Arg Pro Val Asn Gln
1               5                   10                  15

Asp Gly Phe Val Lys Glu Trp Ile Glu Glu Gly Phe Ile Ala Met Glu
            20                  25                  30

Ser Pro Asn Asp Pro Lys Pro Ser Ile Lys Ile Val Asn Gly Ala Val
        35                  40                  45

Thr Glu Leu Asp Gly Lys Pro Val Ser Asp Phe Asp Leu Ile Asp His
    50                  55                  60

Phe Ile Ala Arg Tyr Gly Ile Asn Leu Asn Arg Ala Glu Glu Val Met
65                  70                  75                  80

Ala Met Asp Ser Val Lys Leu Ala Asn Met Leu Cys Asp Pro Asn Val
                85                  90                  95

-continued

```
Lys Arg Ser Glu Ile Val Pro Leu Thr Thr Ala Met Thr Pro Ala Lys
            100                 105                 110
Ile Val Glu Val Val Ser His Met Asn Val Val Glu Met Met Met Ala
        115                 120                 125
Met Gln Lys Met Arg Ala Arg Arg Thr Pro Ser Gln Gln Ala His Val
130                 135                 140
Thr Asn Val Lys Asp Asn Pro Val Gln Ile Ala Ala Asp Ala Ala Glu
145                 150                 155                 160
Gly Ala Trp Arg Gly Phe Asp Glu Gln Glu Thr Thr Val Ala Val Ala
                165                 170                 175
Arg Tyr Ala Pro Phe Asn Ala Ile Ala Leu Leu Val Gly Ser Gln Val
            180                 185                 190
Gly Arg Pro Gly Val Leu Thr Gln Cys Ser Leu Glu Glu Ala Thr Glu
        195                 200                 205
Leu Lys Leu Gly Met Leu Gly His Thr Cys Tyr Ala Glu Thr Ile Ser
210                 215                 220
Val Tyr Gly Thr Glu Pro Val Phe Thr Asp Gly Asp Asp Thr Pro Trp
225                 230                 235                 240
Ser Lys Gly Phe Leu Ala Ser Ser Tyr Ala Ser Arg Gly Leu Lys Met
                245                 250                 255
Arg Phe Thr Ser Gly Ser Gly Ser Glu Val Gln Met Gly Tyr Ala Glu
            260                 265                 270
Gly Lys Ser Met Leu Tyr Leu Glu Ala Arg Cys Ile Tyr Ile Thr Lys
        275                 280                 285
Ala Ala Gly Val Gln Gly Leu Gln Asn Gly Ser Val Ser Cys Ile Gly
290                 295                 300
Val Pro Ser Ala Val Pro Ser Gly Ile Arg Ala Val Leu Ala Glu Asn
305                 310                 315                 320
Leu Ile Cys Ser Ser Leu Asp Leu Glu Cys Ala Ser Ser Asn Asp Gln
                325                 330                 335
Thr Phe Thr His Ser Asp Met Arg Arg Thr Ala Arg Leu Leu Met Gln
            340                 345                 350
Phe Leu Pro Gly Thr Asp Phe Ile Ser Ser Gly Tyr Ser Ala Val Pro
        355                 360                 365
Asn Tyr Asp Asn Met Phe Ala Gly Ser Asn Glu Asp Ala Glu Asp Phe
370                 375                 380
Asp Asp Tyr Asn Val Ile Gln Arg Asp Leu Lys Val Asp Gly Gly Leu
385                 390                 395                 400
Arg Pro Val Arg Glu Glu Asp Val Ile Ala Ile Arg Asn Lys Ala Ala
                405                 410                 415
Arg Ala Leu Gln Ala Val Phe Ala Gly Met Gly Leu Pro Pro Ile Thr
            420                 425                 430
Asp Glu Glu Val Glu Ala Thr Tyr Ala His Gly Ser Lys Asp Met
435                 440                 445
Pro Glu Arg Asn Ile Val Glu Asp Ile Lys Phe Ala Gln Glu Ile Ile
        450                 455                 460
Asn Lys Asn Arg Asn Gly Leu Glu Val Val Lys Ala Leu Ala Gln Gly
465                 470                 475                 480
Gly Phe Thr Asp Val Ala Gln Asp Met Leu Asn Ile Gln Lys Ala Lys
                485                 490                 495
Leu Thr Gly Asp Tyr Leu His Thr Ser Ala Ile Ile Val Gly Asp Gly
            500                 505                 510
Gln Val Leu Ser Ala Val Asn Asp Val Asn Asp Tyr Ala Gly Pro Ala
        515                 520                 525
```

```
Thr Gly Tyr Arg Leu Gln Gly Glu Arg Trp Glu Glu Ile Lys Asn Ile
        530                 535                 540
Pro Gly Ala Leu Asp Pro Asn Glu Ile Asp
545                 550

<210> SEQ ID NO 25
<211> LENGTH: 675
<212> TYPE: DNA
<213> ORGANISM: Klebsiella oxytoca

<400> SEQUENCE: 25
atggaaatta atgaaaaatt gctgcgccag ataattgaag acgtgctcag cgagatgaag      60
ggcagcgata aaccggtctc gtttaatgcg ccggcggcct ccgcggcgcc ccaggccacg     120
ccgcccgccg gcgacggctt cctgacggaa gtgggcgaag cgcgtcaggg aacccagcag     180
gacgaagtga ttatcgccgt cggcccgggc ttcggcctgg cgcagaccgt caatatcgtc     240
ggcatcccgc ataagagcat tttgcgcgaa gtcattgccg gtattgaaga agaaggcatt     300
aaggcgcgcg tgattcgctg cttaaatcc tccgacgtgg ccttcgtcgc cgttgaaggt      360
aatcgcctga gcggctccgg catctctatc ggcatccagt cgaaaggcac cacggtgatc     420
caccagcagg gctgccgcc gctctctaac ctggagctgt tcccgcaggc gccgctgctg      480
accctggaaa cctatcgcca gatcggcaaa aacgccgccc gctatgcgaa cgcgaatcg      540 ccgcagccgg tcccgacgct gaatgaccag atggcgcggc cgaagtacca ggcgaaatcg     600
gccattttgc acattaaaga gaccaagtac gtggtgacgg gcaaaaaccc gcaggaactg     660
cgcgtggcgc tttga                                                      675

<210> SEQ ID NO 26
<211> LENGTH: 224
<212> TYPE: PRT
<213> ORGANISM: Klebsiella oxytoca

<400> SEQUENCE: 26

Met Glu Ile Asn Glu Lys Leu Leu Arg Gln Ile Ile Glu Asp Val Leu
1                   5                   10                  15

Ser Glu Met Lys Gly Ser Asp Lys Pro Val Ser Phe Asn Ala Pro Ala
                20                  25                  30

Ala Ser Ala Ala Pro Gln Ala Thr Pro Pro Ala Gly Asp Gly Phe Leu
            35                  40                  45

Thr Glu Val Gly Glu Ala Arg Gln Gly Thr Gln Gln Asp Glu Val Ile
        50                  55                  60

Ile Ala Val Gly Pro Ala Phe Gly Leu Ala Gln Thr Val Asn Ile Val
65                  70                  75                  80

Gly Ile Pro His Lys Ser Ile Leu Arg Glu Val Ile Ala Gly Ile Glu
                85                  90                  95

Glu Glu Gly Ile Lys Ala Arg Val Ile Arg Cys Phe Lys Ser Ser Asp
            100                 105                 110

Val Ala Phe Val Ala Val Glu Gly Asn Arg Leu Ser Gly Ser Gly Ile
        115                 120                 125

Ser Ile Gly Ile Gln Ser Lys Gly Thr Thr Val Ile His Gln Gln Gly
    130                 135                 140

Leu Pro Pro Leu Ser Asn Leu Glu Leu Phe Pro Gln Ala Pro Leu Leu
145                 150                 155                 160

Thr Leu Glu Thr Tyr Arg Gln Ile Gly Lys Asn Ala Ala Arg Tyr Ala
                165                 170                 175
```

```
Lys Arg Glu Ser Pro Gln Pro Val Pro Thr Leu Asn Asp Gln Met Ala
            180                 185                 190

Arg Pro Lys Tyr Gln Ala Lys Ser Ala Ile Leu His Ile Lys Glu Thr
        195                 200                 205

Lys Tyr Val Val Thr Gly Lys Asn Pro Gln Glu Leu Arg Val Ala Leu
    210                 215                 220

<210> SEQ ID NO 27
<211> LENGTH: 522
<212> TYPE: DNA
<213> ORGANISM: Klebsiella oxytoca

<400> SEQUENCE: 27
atgaataccg acgcaattga atcgatggta cgcgacgtat tgagccgcat gaacagcctg    60
cagggcgagg cgcctgcggc ggctccggcg gctggcggcg cgtcccgtag cgccagggtc   120
agcgactacc cgctggcgaa caagcacccg gaatgggtga aaaccgccac caataaaacg   180
ctggacgact ttacgctgga aaacgtgctg agcaataaag tcaccgccca ggatatgcgt   240
attaccccgg aaaccctgcg cttacaggct tctattgcca agacgcgggg ccgcgaccgg   300
ctggcgatga acttcgagcg cgccgccgag ctgaccgcgg taccggacga tcgcattctt   360
gaaatctaca cgccctccg ccctatcgc tcgacgaaag aggagctgct ggcgatcgcc    420
gacgatctcg aaagccgcta tcaggcgaag atttgcgccg ctttcgttcg cgaagcggcc   480
acgctgtacg tcgagcgtaa aaaactcaaa ggcgacgatt aa                     522

<210> SEQ ID NO 28
<211> LENGTH: 173
<212> TYPE: PRT
<213> ORGANISM: Klebsiella oxytoca

<400> SEQUENCE: 28

Met Asn Thr Asp Ala Ile Glu Ser Met Val Arg Asp Val Leu Ser Arg
1               5                   10                  15

Met Asn Ser Leu Gln Gly Glu Ala Pro Ala Ala Ala Pro Ala Ala Gly
            20                  25                  30

Gly Ala Ser Arg Ser Ala Arg Val Ser Asp Tyr Pro Leu Ala Asn Lys
        35                  40                  45

His Pro Glu Trp Val Lys Thr Ala Thr Asn Lys Thr Leu Asp Asp Phe
    50                  55                  60

Thr Leu Glu Asn Val Leu Ser Asn Lys Val Thr Ala Gln Asp Met Arg
65                  70                  75                  80

Ile Thr Pro Glu Thr Leu Arg Leu Gln Ala Ser Ile Ala Lys Asp Ala
                85                  90                  95

Gly Arg Asp Arg Leu Ala Met Asn Phe Glu Arg Ala Ala Glu Leu Thr
            100                 105                 110

Ala Val Pro Asp Asp Arg Ile Leu Glu Ile Tyr Asn Ala Leu Arg Pro
        115                 120                 125

Tyr Arg Ser Thr Lys Glu Glu Leu Leu Ala Ile Ala Asp Asp Leu Glu
    130                 135                 140

Ser Arg Tyr Gln Ala Lys Ile Cys Ala Ala Phe Val Arg Glu Ala Ala
145                 150                 155                 160

Thr Leu Tyr Val Glu Arg Lys Lys Leu Lys Gly Asp Asp
                165                 170

<210> SEQ ID NO 29
<211> LENGTH: 1041
<212> TYPE: DNA
```

<213> ORGANISM: Rhodococcus ruber

<400> SEQUENCE: 29

```
atgaaagccc tccagtacac cgagatcggc tccgagccgg tcgtcgtcga cgtccccacc      60
ccggcgcccg ggccgggtga gatcctgctg aaggtcaccg cggccggctt gtgccactcg     120
gacatcttcg tgatggacat gccggcagag cagtacatct acggtcttcc cctcacccty     180
ggccacgagg gcgtcggcac cgtcgccgaa ctcggcgccg cgtcaccgg attcgagacg      240
ggggacgccg tcgccgtgta cgggccgtgg gggtgcggtg cgtgccacgc gtgcgcgcgc     300
ggccgggaga actactgcac ccgcgccgcc gagctgggca tcaccccgcc cggtctcggc     360
tcgcccgggt cgatggccga gtacatgatc gtcgactcgg cgcgccacct cgtcccgatc     420
ggggacctcg accccgtcgc ggcggttccg ctcaccgacg cgggcctgac gccgtaccac     480
gcgatctcgc gggtcctgcc cctgctggga cccggctcga ccgcggtcgt catcggggtc     540
ggcggactcg gcacgtcgg catccagatc ctgcgcgccg tcagcgcggc ccgcgtgatc      600
gccgtcgatc tcgacgacga ccgactcgcg ctcgcccgcg aggtcggcgc cgacgcggcg     660
gtgaagtcgg gcgccggggc ggcggacgcg atcggggagc tgaccggcgg tgagggcgcg     720
acggcggtgt tcgacttcgt cggcgcccag tcgacgatcg acacggcgca gcaggtggtc     780
gcgatcgacg ggcacatctc ggtggtcggc atccatgccg gcgcccacgc caaggtcggc     840
ttcttcatga tcccgttcgg cgcgtccgtc gtgacgccgt actggggcac gcggtccgag     900
ctgatggacg tcgtggacct ggccgtgcc ggccggctcg acatccacac cgagacgttc      960
acccctcgacg agggacccac ggcctaccgg cggctacgcg agggcagcat ccgcggccgc    1020
ggggtggtcg tcccgggctg a                                               1041
```

<210> SEQ ID NO 30
<211> LENGTH: 346
<212> TYPE: PRT
<213> ORGANISM: Rhodococcus ruber

<400> SEQUENCE: 30

```
Met Lys Ala Leu Gln Tyr Thr Glu Ile Gly Ser Glu Pro Val Val
1               5                  10                  15

Asp Val Pro Thr Pro Ala Pro Gly Pro Gly Glu Ile Leu Leu Lys Val
            20                  25                  30

Thr Ala Ala Gly Leu Cys His Ser Asp Ile Phe Val Met Asp Met Pro
        35                  40                  45

Ala Glu Gln Tyr Ile Tyr Gly Leu Pro Leu Thr Leu Gly His Glu Gly
    50                  55                  60

Val Gly Thr Val Ala Glu Leu Gly Ala Gly Val Thr Gly Phe Glu Thr
65                  70                  75                  80

Gly Asp Ala Val Ala Val Tyr Gly Pro Trp Gly Cys Gly Ala Cys His
                85                  90                  95

Ala Cys Ala Arg Gly Arg Glu Asn Tyr Cys Thr Arg Ala Ala Glu Leu
            100                 105                 110

Gly Ile Thr Pro Pro Gly Leu Gly Ser Pro Gly Ser Met Ala Glu Tyr
        115                 120                 125

Met Ile Val Asp Ser Ala Arg His Leu Val Pro Ile Gly Asp Leu Asp
    130                 135                 140

Pro Val Ala Ala Val Pro Leu Thr Asp Ala Gly Leu Thr Pro Tyr His
145                 150                 155                 160

Ala Ile Ser Arg Val Leu Pro Leu Leu Gly Pro Gly Ser Thr Ala Val
                165                 170                 175
```

```
Val Ile Gly Val Gly Gly Leu Gly His Val Gly Ile Gln Ile Leu Arg
            180                 185                 190
Ala Val Ser Ala Ala Arg Val Ile Ala Val Asp Leu Asp Asp Asp Arg
        195                 200                 205
Leu Ala Leu Ala Arg Glu Val Gly Ala Asp Ala Ala Val Lys Ser Gly
        210                 215                 220
Ala Gly Ala Ala Asp Ala Ile Arg Glu Leu Thr Gly Glu Gly Ala
225                 230                 235                 240
Thr Ala Val Phe Asp Phe Val Gly Ala Gln Ser Thr Ile Asp Thr Ala
                245                 250                 255
Gln Gln Val Val Ala Ile Asp Gly His Ile Ser Val Val Gly Ile His
            260                 265                 270
Ala Gly Ala His Ala Lys Val Gly Phe Phe Met Ile Pro Phe Gly Ala
        275                 280                 285
Ser Val Val Thr Pro Tyr Trp Gly Thr Arg Ser Glu Leu Met Asp Val
        290                 295                 300
Val Asp Leu Ala Arg Ala Gly Arg Leu Asp Ile His Thr Glu Thr Phe
305                 310                 315                 320
Thr Leu Asp Glu Gly Pro Thr Ala Tyr Arg Arg Leu Arg Glu Gly Ser
                325                 330                 335
Ile Arg Gly Arg Gly Val Val Val Pro Gly
            340                 345

<210> SEQ ID NO 31
<211> LENGTH: 1476
<212> TYPE: DNA
<213> ORGANISM: Escherichia coli

<400> SEQUENCE: 31
atggctaact acttcaatac actgaatctg cgccagcagc tggcacagct gggcaaatgt      60
cgctttatgg ccgcgatga attcgccgat ggcgcgagct accttcaggg taaaaaagta     120
gtcatcgtcg gctgtggcgc acagggtctg aaccagggcc tgaacatgcg tgattctggt     180
ctcgatatct cctacgctct gcgtaaagaa gcgattgccg agaagcgcgc gtcctggcgt     240
aaagcgaccg aaaatggttt taaagtgggt acttacgaag aactgatccc acaggcggat     300
ctggtgatta acctgacgcc ggacaagcag cactctgatg tagtgcgcac cgtacagcca     360
ctgatgaaag acggcgcggc gctgggctac tcgcacggtt tcaacatcgt cgaagtgggc     420
gagcagatcc gtaaagatat caccgtagtg atggttgcgc cgaaatgccc aggcaccgaa     480
gtgcgtgaag agtacaaacg tgggttcggc gtaccgacgc tgattgccgt tcacccggaa     540
aacgatccga aggcgaagg catggcgatt gccaaagcct gggcggctgc aaccggtggt     600
caccgtgcgg gtgtgctgga atcgtccttc gttgcggaag tgaaatctga cctgatgggc     660
gagcaaacca tcctgtgcgg tatgttgcag gctggctctc tgctgtgctt cgacaagctg     720
gtggaagaag gtaccgatcc agcatacgca gaaaaactga ttcagttcgg ttgggaaacc     780
atcaccgaag cactgaaaca gggcggcatc accctgatga tggaccgtct ctctaacccg     840
gcgaaactgc gtgcttatgc gcttctgaa cagctgaaag atcatggc accctgttc       900
cagaaacata tggacgacat catctccggc gaattctctt ccggtatgat ggcggactgg     960
gccaacgatg ataagaaact gctgacctgg cgtgaagaga ccggcaaaac cgcgtttgaa    1020
accgcgccgc agtatgaagg caaaatcggc gagcaggagt acttcgataa aggcgtactg    1080
atgattgcga tggtgaaagc gggcgttgaa ctggcgttcg aaaccatggt cgattccggc    1140
```

-continued

```
atcattgaag agtctgcata ttatgaatca ctgcacgagc tgccgctgat tgccaacacc    1200
atcgcccgta agcgtctgta cgaaatgaac gtggttatct ctgataccgc tgagtacggt    1260
aactatctgt tctcttacgc ttgtgtgccg ttgctgaaac cgtttatggc agagctgcaa    1320
ccgggcgacc tgggtaaagc tattccggaa ggcgcggtag ataacgggca actgcgtgat    1380
gtgaacgaag cgattcgcag ccatgcgatt gagcaggtag gtaagaaact gcgcggctat    1440
atgacagata tgaaacgtat tgctgttgcg ggttaa                              1476
```

<210> SEQ ID NO 32
<211> LENGTH: 491
<212> TYPE: PRT
<213> ORGANISM: Escherichia coli

<400> SEQUENCE: 32

| | | | | | | | | | | | | | |
|---|---|---|---|---|---|---|---|---|---|---|---|---|---|
| Met | Ala | Asn | Tyr | Phe | Asn | Thr | Leu | Asn | Leu | Arg | Gln | Gln | Leu | Ala | Gln |
| 1 | | | | 5 | | | | | 10 | | | | | 15 | |

| Leu | Gly | Lys | Cys | Arg | Phe | Met | Gly | Arg | Asp | Glu | Phe | Ala | Asp | Gly | Ala |
|---|---|---|---|---|---|---|---|---|---|---|---|---|---|---|---|
| | | | 20 | | | | | 25 | | | | | 30 | | |

| Ser | Tyr | Leu | Gln | Gly | Lys | Lys | Val | Ile | Val | Gly | Cys | Gly | Ala | Gln |
|---|---|---|---|---|---|---|---|---|---|---|---|---|---|---|
| | | 35 | | | | | 40 | | | | | 45 | | |

Gly Leu Asn Gln Gly Leu Asn Met Arg Asp Ser Gly Leu Asp Ile Ser
         50                  55                  60

Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                 85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

```
Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
                485                 490

<210> SEQ ID NO 33
<211> LENGTH: 1851
<212> TYPE: DNA
<213> ORGANISM: Escherichia coli

<400> SEQUENCE: 33
atgcctaagt accgttccgc caccaccact catggtcgta atatggcggg tgctcgtgcg      60
ctgtggcgcg ccaccggaat gaccgacgcc gatttcggta agccgattat cgcggttgtg     120
aactcgttca cccaatttgt accgggtcac gtccatctgc gcgatctcgg taaactggtc     180
gccgaacaaa ttgaagcggc tggcggcgtt gccaaagagt tcaacaccat tgcggtggat     240
gatgggattg ccatgggcca cggggggatg ctttattcac tgccatctcg cgaactgatc     300
gctgattccg ttagtatat ggtcaacgcc cactgcgccg acgccatggt ctgcatctct     360
aactgcgaca aaatcacccc gggatgctg atggcttccc tgcgcctgaa tattccggtg     420
atctttgttt ccggcggccc gatggaggcc gggaaaacca acttccga tcagatcatc     480 aagctcgatc tggttgatgc gatgatccag ggcgcagacc cgaaagtatc tgactcccag     540
agcgatcagg ttgaacgttc cgcgtgtccg acctgcggtt cctgctccgg gatgtttacc     600
gctaactcaa tgaactgcct gaccgaagcg ctgggcctgt cgcagccggg caacggctcg     660
ctgctggcaa cccacgccga ccgtaagcag ctgttcctta tgctggtaa acgcattgtt     720 gaattgacca aacgttatta cgagcaaaac gacgaaagtg cactgccgcg taatatcgcc     780
agtaaggcgg cgtttgaaaa cgccatgacg ctggatatcg cgatgggtgg atcgactaac     840
accgtacttc acctgctggc ggcggcgcag gaagcggaaa tcgacttcac catgagtgat     900
atcgataagc tttcccgcaa ggttccacag ctgtgtaaag ttgcgccgag cacccagaaa     960
taccatatgg aagatgttca ccgtgctggt ggtgttatcg gtattctcgg cgaactggat    1020
cgcgcggggt tactgaaccg tgatgtgaaa aacgtacttg gcctgacgtt gccgcaaacg    1080
ctggaacaat acgacgttat gctgacccag gatgacgcgg taaaaaatat gttccgcgca    1140
ggtcctgcag gcattcgtac cacacaggca ttctcgcaag attgccgttg ggatacgctg    1200
```

-continued

```
gacgacgatc gcgccaatgg ctgtatccgc tcgctggaac acgcctacag caaagacggc    1260
ggcctggcgg tgctctacgg taactttgcg gaaaacggct gcatcgtgaa acggcaggc     1320 gtcgatgaca gcatcctcaa attcaccggc ccggcgaaag tgtacgaaag ccaggacgat    1380
gcggtagaag cgattctcgg cggtaaagtt gtcgccggag atgtggtagt aattcgctat    1440
gaaggcccga aggcggtcc ggggatgcag gaaatgctct acccaaccag cttcctgaaa     1500
tcaatgggtc tcggcaaagc ctgtgcgctg atcaccgacg tcgtttctc tggtggcacc     1560 tctggtcttt ccatcggcca cgtctcaccg gaagcggcaa gcggcggcag cattggcctg    1620
attgaagatg gtgacctgat cgctatcgac atcccgaacc gtggcattca gttacaggta    1680
agcgatgccg aactggcggc gcgtcgtgaa gcgcaggacg ctcgaggtga caaagcctgg    1740
acgccgaaaa atcgtgaacg tcaggtctcc tttgccctgc gtgcttatgc cagcctggca    1800
accagcgccg acaaaggcgc ggtgcgcgat aaatcgaaac tggggggtta a             1851
```

```
<210> SEQ ID NO 34
<211> LENGTH: 616
<212> TYPE: PRT
<213> ORGANISM: Escherichia coli

<400> SEQUENCE: 34
```

Met Pro Lys Tyr Arg Ser Ala Thr Thr Thr His Gly Arg Asn Met Ala
1               5                   10                  15

Gly Ala Arg Ala Leu Trp Arg Ala Thr Gly Met Thr Asp Ala Asp Phe
            20                  25                  30

Gly Lys Pro Ile Ile Ala Val Val Asn Ser Phe Thr Gln Phe Val Pro
        35                  40                  45

Gly His Val His Leu Arg Asp Leu Gly Lys Leu Val Ala Glu Gln Ile
    50                  55                  60

Glu Ala Ala Gly Gly Val Ala Lys Glu Phe Asn Thr Ile Ala Val Asp
65                  70                  75                  80

Asp Gly Ile Ala Met Gly His Gly Gly Met Leu Tyr Ser Leu Pro Ser
                85                  90                  95

Arg Glu Leu Ile Ala Asp Ser Val Glu Tyr Met Val Asn Ala His Cys
            100                 105                 110

Ala Asp Ala Met Val Cys Ile Ser Asn Cys Asp Lys Ile Thr Pro Gly
        115                 120                 125

Met Leu Met Ala Ser Leu Arg Leu Asn Ile Pro Val Ile Phe Val Ser
    130                 135                 140

Gly Gly Pro Met Glu Ala Gly Lys Thr Lys Leu Ser Asp Gln Ile Ile
145                 150                 155                 160

Lys Leu Asp Leu Val Asp Ala Met Ile Gln Gly Ala Asp Pro Lys Val
                165                 170                 175

Ser Asp Ser Gln Ser Asp Gln Val Glu Arg Ser Ala Cys Pro Thr Cys
            180                 185                 190

Gly Ser Cys Ser Gly Met Phe Thr Ala Asn Ser Met Asn Cys Leu Thr
        195                 200                 205

Glu Ala Leu Gly Leu Ser Gln Pro Gly Asn Gly Ser Leu Leu Ala Thr
    210                 215                 220

His Ala Asp Arg Lys Gln Leu Phe Leu Asn Ala Gly Lys Arg Ile Val
225                 230                 235                 240

Glu Leu Thr Lys Arg Tyr Tyr Glu Gln Asn Asp Glu Ser Ala Leu Pro
                245                 250                 255

Arg Asn Ile Ala Ser Lys Ala Ala Phe Glu Asn Ala Met Thr Leu Asp

```
                260              265              270
Ile Ala Met Gly Gly Ser Thr Asn Thr Val Leu His Leu Leu Ala Ala
            275              280              285

Ala Gln Glu Ala Glu Ile Asp Phe Thr Met Ser Asp Ile Asp Lys Leu
        290              295              300

Ser Arg Lys Val Pro Gln Leu Cys Lys Val Ala Pro Ser Thr Gln Lys
305              310              315              320

Tyr His Met Glu Asp Val His Arg Ala Gly Val Ile Gly Ile Leu
            325              330              335

Gly Glu Leu Asp Arg Ala Gly Leu Leu Asn Arg Asp Val Lys Asn Val
            340              345              350

Leu Gly Leu Thr Leu Pro Gln Thr Leu Glu Gln Tyr Asp Val Met Leu
            355              360              365

Thr Gln Asp Asp Ala Val Lys Asn Met Phe Arg Ala Gly Pro Ala Gly
        370              375              380

Ile Arg Thr Thr Gln Ala Phe Ser Gln Asp Cys Arg Trp Asp Thr Leu
385              390              395              400

Asp Asp Asp Arg Ala Asn Gly Cys Ile Arg Ser Leu Glu His Ala Tyr
                405              410              415

Ser Lys Asp Gly Gly Leu Ala Val Leu Tyr Gly Asn Phe Ala Glu Asn
            420              425              430

Gly Cys Ile Val Lys Thr Ala Gly Val Asp Asp Ser Ile Leu Lys Phe
            435              440              445

Thr Gly Pro Ala Lys Val Tyr Glu Ser Gln Asp Asp Ala Val Glu Ala
        450              455              460

Ile Leu Gly Gly Lys Val Val Ala Gly Asp Val Val Ile Arg Tyr
465              470              475              480

Glu Gly Pro Lys Gly Gly Pro Gly Met Gln Glu Met Leu Tyr Pro Thr
                485              490              495

Ser Phe Leu Lys Ser Met Gly Leu Gly Lys Ala Cys Ala Leu Ile Thr
            500              505              510

Asp Gly Arg Phe Ser Gly Gly Thr Ser Gly Leu Ser Ile Gly His Val
        515              520              525

Ser Pro Glu Ala Ala Ser Gly Gly Ser Ile Gly Leu Ile Glu Asp Gly
    530              535              540

Asp Leu Ile Ala Ile Asp Ile Pro Asn Arg Gly Ile Gln Leu Gln Val
545              550              555              560

Ser Asp Ala Glu Leu Ala Ala Arg Arg Glu Ala Gln Asp Ala Arg Gly
                565              570              575

Asp Lys Ala Trp Thr Pro Lys Asn Arg Glu Arg Gln Val Ser Phe Ala
            580              585              590

Leu Arg Ala Tyr Ala Ser Leu Ala Thr Ser Ala Asp Lys Gly Ala Val
            595              600              605

Arg Asp Lys Ser Lys Leu Gly Gly
        610              615

<210> SEQ ID NO 35
<211> LENGTH: 1662
<212> TYPE: DNA
<213> ORGANISM: Lactococcus lactis

<400> SEQUENCE: 35
tctagacata tgtatactgt gggggattac ctgctggatc gcctgcacga actggggatt    60
gaagaaattt tcggtgtgcc aggcgattat aacctgcagt cctggaccag gattatctcg   120
```

```
cacaaagata tgaagtgggt cggtaacgcc aacgaactga acgcgagcta tatggcagat    180
ggttatgccc gtaccaaaaa agctgctgcg tttctgacga ccttttggcgt tggcgaactg    240 agcgccgtca acggactggc aggaagctac gccgagaacc tgccagttgt cgaaattgtt    300
gggtcgccta cttctaaggt tcagaatgaa ggcaaatttg tgcaccatac tctggctgat    360
ggggatttta acatttttat gaaaatgcat gaaccggtta ctgcggcccg cacgctgctg    420
acagcagaga tgctacggt tgagatcgac cgcgtcctgt ctgcgctgct gaaagagcgc    480
aagccggtat atatcaatct gcctgtcgat gttgccgcag cgaaagccga aaagccgtcg    540
ctgccactga aaaagaaaa cagcacctcc aatacatcgg accaggaaat tctgaataaa    600
atccaggaat cactgaagaa tgcgaagaaa ccgatcgtca tcaccggaca tgagatcatc    660
tcttttggcc tggaaaaaac ggtcacgcag ttcatttcta agaccaaact gcctatcacc    720
accctgaact tcggcaaatc tagcgtcgat gaagcgctgc cgagttttct gggtatctat    780
aatggtaccc tgtccgaacc gaacctgaaa gaattcgtcg aaagcgcgga ctttatcctg    840
atgctgggcg tgaaactgac ggatagctcc acaggcgcat ttacccacca tctgaacgag    900
aataaaatga tttccctgaa tatcgacgaa ggcaaaatct ttaacgagcg catccagaac    960
ttcgattttg aatctctgat tagttcgctg ctggatctgt ccgaaattga gtataaaggt   1020
aaatatattg ataaaaaaca ggaggatttt gtgccgtcta atgcgctgct gagtcaggat   1080
cgtctgtggc aagccgtaga aaacctgaca cagtctaatg aaacgattgt tgcggaacag   1140
ggaacttcat ttttcggcgc ctcatccatt tttctgaaat ccaaaagcca tttcattggc   1200
caaccgctgt gggggagtat tggttatacc tttccggcgg cgctgggttc acagattgca   1260
gataaggaat cacgccatct gctgtttatt ggtgacggca gcctgcagct gactgtccag   1320
gaactggggc tggcgatccg tgaaaaaatc aatccgattt gctttatcat caataacgac   1380
ggctacaccg tcgaacgcga aattcatgga ccgaatcaaa gttacaatga catcccgatg   1440
tggaactata gcaaactgcc ggaatccttt ggcgcgacac aggatcgcgt ggtgagtaaa   1500
attgtgcgta cggaaaacga atttgtgtcg gttatgaaag aagcgcaggc tgacccgaat   1560
cgcatgtatt ggattgaact gatcctggca aaagaaggcg caccgaaagt tctgaaaaag   1620
atggggaaac tgtttgcgga gcaaaataaa agctaaggat cc                     1662
```

<210> SEQ ID NO 36
<211> LENGTH: 548
<212> TYPE: PRT
<213> ORGANISM: Lactococcus lactis

<400> SEQUENCE: 36

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

```
His Thr Leu Ala Asp Gly Asp Phe Lys His Phe Met Lys Met His Glu
            115                 120                 125

Pro Val Thr Ala Ala Arg Thr Leu Leu Thr Ala Glu Asn Ala Thr Val
        130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Lys Ala Glu Lys Pro
                165                 170                 175

Ser Leu Pro Leu Lys Lys Glu Asn Ser Thr Ser Asn Thr Ser Asp Gln
                180                 185                 190

Glu Ile Leu Asn Lys Ile Gln Glu Ser Leu Lys Asn Ala Lys Lys Pro
            195                 200                 205

Ile Val Ile Thr Gly His Glu Ile Ile Ser Phe Gly Leu Glu Lys Thr
            210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
                260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
        290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
                340                 345                 350

Leu Leu Ser Gln Asp Arg Leu Trp Gln Ala Val Glu Asn Leu Thr Gln
                355                 360                 365

Ser Asn Glu Thr Ile Val Ala Glu Gln Gly Thr Ser Phe Phe Gly Ala
        370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
                420                 425                 430

Gln Leu Thr Val Gln Glu Leu Gly Leu Ala Ile Arg Glu Lys Ile Asn
            435                 440                 445

Pro Ile Cys Phe Ile Ile Asn Asn Asp Gly Tyr Thr Val Glu Arg Glu
            450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
                500                 505                 510

Gln Ala Asp Pro Asn Arg Met Tyr Trp Ile Glu Leu Ile Leu Ala Lys
            515                 520                 525

Glu Gly Ala Pro Lys Val Leu Lys Lys Met Gly Lys Leu Phe Ala Glu
```

Gln Asn Lys Ser
545

<210> SEQ ID NO 37
<211> LENGTH: 1164
<212> TYPE: DNA
<213> ORGANISM: Escherichia coli

<400> SEQUENCE: 37

| | | | | | |
|---|---|---|---|---|---|
| atgaacaact | ttaatctgca | caccccaacc | cgcattctgt | ttggtaaagg cgcaatcgct | 60 |
| ggtttacgcg | aacaaattcc | tcacgatgct | cgcgtattga | ttacctacgg cggcggcagc | 120 |
| gtgaaaaaaa | ccggcgttct | cgatcaagtt | ctggatgccc | tgaaaggcat ggacgtgctg | 180 |
| gaatttggcg | gtattgagcc | aaacccggct | tatgaaacgc | tgatgaacgc cgtgaaactg | 240 |
| gttcgcgaac | agaaagtgac | tttcctgctg | gcggttggcg | gcggttctgt actggacggc | 300 |
| accaaattta | tcgccgcagc | ggctaactat | ccggaaaata | tcgatccgtg cacattctg | 360 |
| caaacgggcg | taaagagat | taaaagcgcc | atcccgatgg | gctgtgtgct gacgctgcca | 420 |
| gcaaccggtt | cagaatccaa | cgcaggcgcg | gtgatctccc | gtaaaaccac aggcgacaag | 480 |
| caggcgttcc | attctgccca | tgttcagccg | gtatttgccg | tgctcgatcc ggtttatacc | 540 |
| tacaccctgc | cgccgcgtca | ggtggctaac | ggcgtagtgg | acgcctttgt acacaccgtg | 600 |
| gaacagtatg | ttaccaaacc | ggttgatgcc | aaaattcagg | accgtttcgc agaaggcatt | 660 |
| ttgctgacgc | taatcgaaga | tggtccgaaa | gccctgaaag | agccagaaaa ctacgatgtg | 720 |
| cgcgccaacg | tcatgtgggc | ggcgactcag | gcgctgaacg | gtttgattgg cgctggcgta | 780 |
| ccgcaggact | gggcaacgca | tatgctgggc | acgaactga | ctgcgatgca cggtctggat | 840 |
| cacgcgcaaa | cactggctat | cgtcctgcct | gcactgtgga | tgaaaaacg cgataccaag | 900 |
| cgcgctaagc | tgctgcaata | tgctgaacgc | gtctggaaca | tcactgaagg ttccgatgat | 960 |
| gagcgtattg | acgccgcgat | tgccgcaacc | cgcaatttct | ttgagcaatt aggcgtgccg | 1020 |
| acccacctct | ccgactacgg | tctggacggc | agctccatcc | cggctttgct gaaaaaactg | 1080 |
| gaagagcacg | gcatgaccca | actgggcgaa | aatcatgaca | ttacgttgga tgtcagccgc | 1140 |
| cgtatatacg | aagccgcccg | ctaa | | | 1164 |

<210> SEQ ID NO 38
<211> LENGTH: 387
<212> TYPE: PRT
<213> ORGANISM: Escherichia coli

<400> SEQUENCE: 38

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Ala Asn Tyr Pro Glu

Asn Ile Asp Pro Trp His Ile Leu Gln Thr Gly Gly Lys Glu Ile Lys
            115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
            195                 200                 205

Asp Ala Lys Ile Gln Asp Arg Phe Ala Glu Gly Ile Leu Leu Thr Leu
            210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
            275                 280                 285

Leu Pro Ala Leu Trp Asn Glu Lys Arg Asp Thr Lys Arg Ala Lys Leu
            290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
            355                 360                 365

Gly Glu Asn His Asp Ile Thr Leu Asp Val Ser Arg Arg Ile Tyr Glu
370                 375                 380

Ala Ala Arg
385

<210> SEQ ID NO 39
<211> LENGTH: 1197
<212> TYPE: DNA
<213> ORGANISM: Saccharomyces cerevisiae

<400> SEQUENCE: 39
atgtctcaga acgtttacat tgtatcgact gccagaaccc caattggttc attccagggt      60
tctctatcct ccaagacagc agtggaattg ggtgctgttg ctttaaaagg cgccttggct     120
aaggttccag aattggatgc atccaaggat tttgacgaaa ttattttggg taacgttctt     180
tctgccaatt tgggccaagc tccggccaga caagttgctt tggctgccgg tttgagtaat     240
catatcgttg caagcacagt taacaaggtc tgtgcatccg ctatgaaggc aatcattttg     300
ggtgctcaat ccatcaaatg tggtaatgct gatgttgtcg tagctggtgg ttgtgaatct     360
atgactaacg caccatacta catgccagca gcccgtgcgg gtgccaaatt tggccaaact     420
gttcttgttg atggtgtcga agagatgggt tgaacgatg cgtacgatgg tctagccatg     480

```
ggtgtacacg cagaaaagtg tgcccgtgat tgggatatta ctagagaaca acaagacaat    540
tttgccatcg aatcctacca aaaatctcaa aaatctcaaa aggaaggtaa attcgacaat    600
gaaattgtac ctgttaccat taagggattt agaggtaagc ctgatactca agtcacgaag    660
gacgaggaac ctgctagatt acacgttgaa aaattgagat ctgcaaggac tgttttccaa    720
aaagaaaacg gtactgttac tgccgctaac gcttctccaa tcaacgatgg tgctgcagcc    780
gtcatcttgg tttccgaaaa agttttgaag gaaaagaatt tgaagccttt ggctattatc    840
aaaggttggg gtgaggccgc tcatcaacca gctgatttta catgggctcc atctcttgca    900
gttccaaagg ctttgaaaca tgctggcatc gaagacatca attctgttga ttactttgaa    960
ttcaatgaag cctttcggt tgtcggtttg gtgaacacta agattttgaa gctagaccca   1020
tctaaggtta atgtatatgg tggtgctgtt gctctaggtc acccattggg ttgttctggt   1080
gctagagtgg ttgttacact gctatccatc ttacagcaag aaggaggtaa gatcggtgtt   1140
gccgccattt gtaatggtgg tggtggtgct tcctctattg tcattgaaaa gatatga      1197
```

<210> SEQ ID NO 40
<211> LENGTH: 398
<212> TYPE: PRT
<213> ORGANISM: Saccharomyces cerevisiae

<400> SEQUENCE: 40

```
Met Ser Gln Asn Val Tyr Ile Val Ser Thr Ala Arg Thr Pro Ile Gly
1               5                   10                  15

Ser Phe Gln Gly Ser Leu Ser Ser Lys Thr Ala Val Glu Leu Gly Ala
            20                  25                  30

Val Ala Leu Lys Gly Ala Leu Ala Lys Val Pro Glu Leu Asp Ala Ser
        35                  40                  45

Lys Asp Phe Asp Glu Ile Ile Phe Gly Asn Val Leu Ser Ala Asn Leu
    50                  55                  60

Gly Gln Ala Pro Ala Arg Gln Val Ala Leu Ala Ala Gly Leu Ser Asn
65                  70                  75                  80

His Ile Val Ala Ser Thr Val Asn Lys Val Cys Ala Ser Ala Met Lys
                85                  90                  95

Ala Ile Ile Leu Gly Ala Gln Ser Ile Lys Cys Gly Asn Ala Asp Val
            100                 105                 110

Val Val Ala Gly Gly Cys Glu Ser Met Thr Asn Ala Pro Tyr Tyr Met
        115                 120                 125

Pro Ala Ala Arg Ala Gly Ala Lys Phe Gly Gln Thr Val Leu Val Asp
    130                 135                 140

Gly Val Glu Arg Asp Gly Leu Asn Asp Ala Tyr Asp Gly Leu Ala Met
145                 150                 155                 160

Gly Val His Ala Glu Lys Cys Ala Arg Asp Trp Ile Thr Arg Glu
                165                 170                 175

Gln Gln Asp Asn Phe Ala Ile Glu Ser Tyr Gln Lys Ser Gln Lys Ser
            180                 185                 190

Gln Lys Glu Gly Lys Phe Asp Asn Glu Ile Val Pro Val Thr Ile Lys
        195                 200                 205

Gly Phe Arg Gly Lys Pro Asp Thr Gln Val Thr Lys Asp Glu Glu Pro
    210                 215                 220

Ala Arg Leu His Val Glu Lys Leu Arg Ser Ala Arg Thr Val Phe Gln
225                 230                 235                 240

Lys Glu Asn Gly Thr Val Thr Ala Ala Asn Ala Ser Pro Ile Asn Asp
                245                 250                 255
```

```
Gly Ala Ala Ala Val Ile Leu Val Ser Glu Lys Val Leu Lys Glu Lys
                260                 265                 270

Asn Leu Lys Pro Leu Ala Ile Ile Lys Gly Trp Gly Glu Ala Ala His
            275                 280                 285

Gln Pro Ala Asp Phe Thr Trp Ala Pro Ser Leu Ala Val Pro Lys Ala
        290                 295                 300

Leu Lys His Ala Gly Ile Glu Asp Ile Asn Ser Val Asp Tyr Phe Glu
305                 310                 315                 320

Phe Asn Glu Ala Phe Ser Val Val Gly Leu Val Asn Thr Lys Ile Leu
                325                 330                 335

Lys Leu Asp Pro Ser Lys Val Asn Val Tyr Gly Gly Ala Val Ala Leu
            340                 345                 350

Gly His Pro Leu Gly Cys Ser Gly Ala Arg Val Val Thr Leu Leu
        355                 360                 365

Ser Ile Leu Gln Gln Glu Gly Gly Lys Ile Gly Val Ala Ala Ile Cys
370                 375                 380

Asn Gly Gly Gly Gly Ala Ser Ser Ile Val Ile Glu Lys Ile
385                 390                 395
```

<210> SEQ ID NO 41
<211> LENGTH: 1716
<212> TYPE: DNA
<213> ORGANISM: Bacillus subtilis

<400> SEQUENCE: 41

```
atgttgacaa aagcaacaaa agaacaaaaa tcccttgtga aaaacagagg ggcggagctt      60
gttgttgatt gcttagtgga gcaaggtgtc acacatgtat ttggcattcc aggtgcaaaa     120
attgatgcgg tatttgacgc tttacaagat aaaggacctg aaattatcgt tgcccggcac     180
gaacaaaacg cagcattcat ggcccaagca gtcggccgtt taactggaaa accgggagtc     240
gtgttagtca catcaggacc gggtgcctct aacttggcaa caggcctgct gacagcgaac     300
actgaaggag accctgtcgt tgcgcttgct ggaaacgtga tccgtgcaga tcgtttaaaa     360
cggacacatc aatctttgga taatgcggcg ctattccagc cgattacaaa atacagtgta     420
gaagttcaag atgtaaaaaa tataccggaa gctgttacaa atgcatttag gatagcgtca     480
gcagggcagg ctggggccgc ttttgtgagc tttccgcaag atgttgtgaa tgaagtcaca     540
aatacgaaaa acgtgcgtgc tgttcagcg ccaaaactcg gtcctgcagc agatgatgca     600
atcagtgcgg ccatagcaaa aatccaaaca gcaaaacttc ctgtcgtttt ggtcggcatg     660
aaaggcggaa gaccggaagc aattaaagcg gttcgcaagc tttgaaaaa ggttcagctt     720
ccatttgttg aaacatatca agctgccggt acccttcta gagatttaga ggatcaatat     780
tttggccgta tcggtttgtt ccgcaaccag cctggcgatt tactgctaga gcaggcagat     840
gttgttctga cgatcggcta tgacccgatt gaatatgatc cgaaattctg gaatatcaat     900
ggagaccgga caattatcca tttagacgag attatcgctg acattgatca tgcttaccag     960
cctgatcttg aattgatcgg tgacattccg tccacgatca atcatatcga acacgatgct    1020
gtgaaagtgg aatttgcaga gcgtgagcag aaaatccttt ctgatttaaa acaatatatg    1080
catgaaggtg agcaggtgcc tgcagattgg aaatcagaca gagcgcaccc tcttgaaatc    1140
gttaaagagt tgcgtaatgc agtcgatgat catgttacga taacttgcga tatcggttcg    1200
cacgccattt ggatgtcacg ttatttccgc agctacgagc cgttaacatt aatgatcagt    1260
aacggtatgc aaacactcgg cgttgcgctt ccttgggcaa tcggcgcttc attggtgaaa    1320
ccgggagaaa aagtggtttc tgtctctggt gacggcggtt tcttattctc agcaatggaa    1380
```

-continued

```
ttagagacag cagttcgact aaaagcacca attgtacaca ttgtatggaa cgacagcaca    1440
tatgacatgg ttgcattcca gcaattgaaa aaatataacc gtacatctgc ggtcgatttc    1500
ggaaatatcg atatcgtgaa atatgcggaa agcttcggag caactggctt gcgcgtagaa    1560
tcaccagacc agctggcaga tgttctgcgt caaggcatga acgctgaagg tcctgtcatc    1620
atcgatgtcc cggttgacta cagtgataac attaatttag caagtgacaa gcttccgaaa    1680
gaattcgggg aactcatgaa aacgaaagct ctctag                              1716
```

<210> SEQ ID NO 42
<211> LENGTH: 571
<212> TYPE: PRT
<213> ORGANISM: Bacillus subtilis

<400> SEQUENCE: 42

```
Met Leu Thr Lys Ala Thr Lys Glu Gln Lys Ser Leu Val Lys Asn Arg
1               5                   10                  15

Gly Ala Glu Leu Val Val Asp Cys Leu Val Gln Gly Val Thr His
            20                  25                  30

Val Phe Gly Ile Pro Gly Ala Lys Ile Asp Ala Val Phe Asp Ala Leu
        35                  40                  45

Gln Asp Lys Gly Pro Glu Ile Ile Val Ala Arg His Glu Gln Asn Ala
    50                  55                  60

Ala Phe Met Ala Gln Ala Val Gly Arg Leu Thr Gly Lys Pro Gly Val
65                  70                  75                  80

Val Leu Val Thr Ser Gly Pro Gly Ala Ser Asn Leu Ala Thr Gly Leu
                85                  90                  95

Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
        115                 120                 125

Ala Ala Leu Phe Gln Pro Ile Thr Lys Tyr Ser Val Glu Val Gln Asp
    130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Ala Pro Lys
            180                 185                 190

Leu Gly Pro Ala Ala Asp Asp Ala Ile Ser Ala Ala Ile Ala Lys Ile
        195                 200                 205

Gln Thr Ala Lys Leu Pro Val Val Leu Val Gly Met Lys Gly Gly Arg
    210                 215                 220

Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Ser Arg Asp Leu
                245                 250                 255

Glu Asp Gln Tyr Phe Gly Arg Ile Gly Leu Phe Arg Asn Gln Pro Gly
            260                 265                 270

Asp Leu Leu Leu Glu Gln Ala Asp Val Val Leu Thr Ile Gly Tyr Asp
        275                 280                 285

Pro Ile Glu Tyr Asp Pro Lys Phe Trp Asn Ile Asn Gly Asp Arg Thr
    290                 295                 300

Ile Ile His Leu Asp Glu Ile Ile Ala Asp Ile Asp His Ala Tyr Gln
305                 310                 315                 320
```

```
Pro Asp Leu Glu Leu Ile Gly Asp Ile Pro Ser Thr Ile Asn His Ile
            325                 330                 335

Glu His Asp Ala Val Lys Val Glu Phe Ala Glu Arg Glu Gln Lys Ile
            340                 345                 350

Leu Ser Asp Leu Lys Gln Tyr Met His Glu Gly Glu Gln Val Pro Ala
            355                 360                 365

Asp Trp Lys Ser Asp Arg Ala His Pro Leu Glu Ile Val Lys Glu Leu
            370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
                405                 410                 415

Leu Met Ile Ser Asn Gly Met Gln Thr Leu Gly Val Ala Leu Pro Trp
                420                 425                 430

Ala Ile Gly Ala Ser Leu Val Lys Pro Gly Glu Lys Val Val Ser Val
                435                 440                 445

Ser Gly Asp Gly Gly Phe Leu Phe Ser Ala Met Glu Leu Glu Thr Ala
            450                 455                 460

Val Arg Leu Lys Ala Pro Ile Val His Ile Val Trp Asn Asp Ser Thr
465                 470                 475                 480

Tyr Asp Met Val Ala Phe Gln Gln Leu Lys Lys Tyr Asn Arg Thr Ser
                485                 490                 495

Ala Val Asp Phe Gly Asn Ile Asp Ile Val Lys Tyr Ala Glu Ser Phe
                500                 505                 510

Gly Ala Thr Gly Leu Arg Val Glu Ser Pro Asp Gln Leu Ala Asp Val
            515                 520                 525

Leu Arg Gln Gly Met Asn Ala Glu Gly Pro Val Ile Ile Asp Val Pro
            530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
                565                 570

<210> SEQ ID NO 43
<211> LENGTH: 1188
<212> TYPE: DNA
<213> ORGANISM: Saccharomyces cerevisiae

<400> SEQUENCE: 43
atgttgagaa ctcaagccgc cagattgatc tgcaactccc gtgtcatcac tgctaagaga      60
acctttgctt tggccaccccg tgctgctgct tacagcagac cagctgcccg tttcgttaag    120
ccaatgatca ctacccgtgg tttgaagcaa atcaacttcg gtggtactgt tgaaaccgtc    180
tacgaaagag ctgactggcc aagagaaaag ttgttggact acttcaagaa cgacactttt    240
gctttgatcg gttacggttc ccaaggttac ggtcaaggtt tgaacttgag agacaacggt    300
ttgaacgtta tcattggtgt ccgtaaagat ggtgcttctt ggaaggctgc catcgaagac    360
ggttgggttc aggcaagaa cttgttcact gttgaagatg ctatcaagag aggtagttac    420
gttatgaact gttgtccga tgccgctcaa tcagaaacct ggcctgctat caagccattg    480
ttgaccaagg taagactttt gtacttctcc cacggtttct ccccagtctt caaggacttg    540
actcacgttg aaccaccaaa ggacttagat gttatcttgg ttgctccaaa gggttccggt    600
agaactgtca gatctttgtt caaggaaggt cgtggtatta actcttctta cgccgtctgg    660
aacgatgtca ccggtaaggc tcacgaaaag gcccaagctt tggccgttgc cattggttcc    720
```

```
ggttacgttt accaaaccac tttcgaaaga gaagtcaact ctgacttgta cggtgaaaga    780
ggttgtttaa tgggtggtat ccacggtatg ttcttggctc aatacgacgt cttgagagaa    840
aacggtcact ccccatctga agctttcaac gaaaccgtcg aagaagctac ccaatctcta    900
tacccattga tcggtaagta cggtatggat tacatgtacg atgcttgttc caccaccgcc    960
agaagaggtg ctttggactg gtacccaatc ttcaagaatg ctttgaagcc tgttttccaa   1020
gacttgtacg aatctaccaa gaacggtacc gaaaccaaga gatctttgga attcaactct   1080
caacctgact acagagaaaa gctagaaaag gaattagaca ccatcagaaa catggaaatc   1140
tggaaggttg gtaaggaagt cagaaagttg agaccagaaa accaataa               1188
```

<210> SEQ ID NO 44
<211> LENGTH: 395
<212> TYPE: PRT
<213> ORGANISM: Saccharomyces cerevisiae

<400> SEQUENCE: 44

```
Met Leu Arg Thr Gln Ala Ala Arg Leu Ile Cys Asn Ser Arg Val Ile
1               5                   10                  15

Thr Ala Lys Arg Thr Phe Ala Leu Ala Thr Arg Ala Ala Ala Tyr Ser
            20                  25                  30

Arg Pro Ala Ala Arg Phe Val Lys Pro Met Ile Thr Thr Arg Gly Leu
        35                  40                  45

Lys Gln Ile Asn Phe Gly Gly Thr Val Glu Thr Val Tyr Glu Arg Ala
    50                  55                  60

Asp Trp Pro Arg Glu Lys Leu Leu Asp Tyr Phe Lys Asn Asp Thr Phe
65                  70                  75                  80

Ala Leu Ile Gly Tyr Gly Ser Gln Gly Tyr Gly Gln Gly Leu Asn Leu
                85                  90                  95

Arg Asp Asn Gly Leu Asn Val Ile Ile Gly Val Arg Lys Asp Gly Ala
            100                 105                 110

Ser Trp Lys Ala Ala Ile Glu Asp Gly Trp Val Pro Gly Lys Asn Leu
        115                 120                 125

Phe Thr Val Glu Asp Ala Ile Lys Arg Gly Ser Tyr Val Met Asn Leu
    130                 135                 140

Leu Ser Asp Ala Ala Gln Ser Glu Thr Trp Pro Ala Ile Lys Pro Leu
145                 150                 155                 160

Leu Thr Lys Gly Lys Thr Leu Tyr Phe Ser His Gly Phe Ser Pro Val
                165                 170                 175

Phe Lys Asp Leu Thr His Val Glu Pro Pro Lys Asp Leu Asp Val Ile
            180                 185                 190

Leu Val Ala Pro Lys Gly Ser Gly Arg Thr Val Arg Ser Leu Phe Lys
        195                 200                 205

Glu Gly Arg Gly Ile Asn Ser Ser Tyr Ala Val Trp Asn Asp Val Thr
    210                 215                 220

Gly Lys Ala His Glu Lys Ala Gln Ala Leu Ala Val Ala Ile Gly Ser
225                 230                 235                 240

Gly Tyr Val Tyr Gln Thr Thr Phe Glu Arg Glu Val Asn Ser Asp Leu
                245                 250                 255

Tyr Gly Glu Arg Gly Cys Leu Met Gly Gly Ile His Gly Met Phe Leu
            260                 265                 270

Ala Gln Tyr Asp Val Leu Arg Glu Asn Gly His Ser Pro Ser Glu Ala
        275                 280                 285

Phe Asn Glu Thr Val Glu Glu Ala Thr Gln Ser Leu Tyr Pro Leu Ile
```

```
            290                 295                 300
Gly Lys Tyr Gly Met Asp Tyr Met Tyr Asp Ala Cys Ser Thr Thr Ala
305                 310                 315                 320

Arg Arg Gly Ala Leu Asp Trp Tyr Pro Ile Phe Lys Asn Ala Leu Lys
            325                 330                 335

Pro Val Phe Gln Asp Leu Tyr Glu Ser Thr Lys Asn Gly Thr Glu Thr
            340                 345                 350

Lys Arg Ser Leu Glu Phe Asn Ser Gln Pro Asp Tyr Arg Glu Lys Leu
            355                 360                 365

Glu Lys Glu Leu Asp Thr Ile Arg Asn Met Glu Ile Trp Lys Val Gly
            370                 375                 380

Lys Glu Val Arg Lys Leu Arg Pro Glu Asn Gln
385                 390                 395

<210> SEQ ID NO 45
<211> LENGTH: 1029
<212> TYPE: DNA
<213> ORGANISM: Bacillus subtilis

<400> SEQUENCE: 45
atggtaaaag tatattataa cggtgatatc aaagagaacg tattggctgg aaaaacagta      60
gcggttatcg ggtacggttc gcaaggccac gcacatgccc tgaaccttaa agaaagcgga     120
gtagacgtga tcgtcggtgt tagacaagga aaatctttca ctcaagccca agaagacgga     180
cataaagtat tttcagtaaa agaagcggca gcccaagccg aaatcatcat ggttctgctt     240
ccggatgagc agcagcaaaa agtatacgaa gctgaaatca agatgaatt gacagcagga     300 aaatcattag tattcgctca tggatttaac gtgcatttcc atcaaattgt tcctccggcg     360
gatgtagatg tattcttagt ggcccctaaa ggcccgggac acttggtaag aagaacatat     420
gagcaaggag ctggcgtacc tgcattgttc gcaatctatc aagatgtgac tggagaagca     480
agagacaaag ccctcgctta tgctaaagga atcggcggcg caagagcggg cgtattagaa     540
acgacattta agaagaaac agaaacagat ttgttcggtg agcaagcagt tctttgcggc     600
ggattaagcg cgcttgtcaa agccggattt gaaaccttaa ctgaagcagg ttatcagcct     660
gaacttgcat acttcgagtg tcttcatgag ctgaaattaa tcgtagacct tatgtacgaa     720
gaaggacttg caggaatgag atattcaatc tctgacacag cacagtgggg agatttcgta     780
tcaggccctc gcgttgtgga cgccaaagta aaagaatcta tgaaagaagt attaaaagat     840
atccaaaacg gtacattcgc aaaagagtgg atcgtcgaaa accaagtaaa ccgtcctcgt     900
ttcaacgcta tcaatgcaag cgagaacgaa catcaaatcg aagtagtggg aagaaagctt     960
cgtgaaatga tgccgtttgt gaaacaaggc aagaagaagg aagcggtggt ctccgttgcg    1020
caaaattaa                                                            1029

<210> SEQ ID NO 46
<211> LENGTH: 342
<212> TYPE: PRT
<213> ORGANISM: Bacillus subtilis

<400> SEQUENCE: 46

Met Val Lys Val Tyr Tyr Asn Gly Asp Ile Lys Glu Asn Val Leu Ala
1               5                   10                  15

Gly Lys Thr Val Ala Val Ile Gly Tyr Gly Ser Gln Gly His Ala His
            20                  25                  30

Ala Leu Asn Leu Lys Glu Ser Gly Val Asp Val Ile Val Gly Val Arg
        35                  40                  45
```

```
Gln Gly Lys Ser Phe Thr Gln Ala Gln Glu Asp Gly His Lys Val Phe
    50                  55                  60

Ser Val Lys Glu Ala Ala Gln Ala Glu Ile Ile Met Val Leu Leu
65                  70                  75                  80

Pro Asp Glu Gln Gln Lys Val Tyr Glu Ala Glu Ile Lys Asp Glu
                85                  90                  95

Leu Thr Ala Gly Lys Ser Leu Val Phe Ala His Gly Phe Asn Val His
            100                 105                 110

Phe His Gln Ile Val Pro Pro Ala Asp Val Asp Val Phe Leu Val Ala
            115                 120                 125

Pro Lys Gly Pro Gly His Leu Val Arg Arg Thr Tyr Glu Gln Gly Ala
130                 135                 140

Gly Val Pro Ala Leu Phe Ala Ile Tyr Gln Asp Val Thr Gly Glu Ala
145                 150                 155                 160

Arg Asp Lys Ala Leu Ala Tyr Ala Lys Gly Ile Gly Gly Ala Arg Ala
                165                 170                 175

Gly Val Leu Glu Thr Thr Phe Lys Glu Thr Glu Thr Asp Leu Phe
            180                 185                 190

Gly Glu Gln Ala Val Leu Cys Gly Gly Leu Ser Ala Leu Val Lys Ala
            195                 200                 205

Gly Phe Glu Thr Leu Thr Glu Ala Gly Tyr Gln Pro Glu Leu Ala Tyr
210                 215                 220

Phe Glu Cys Leu His Glu Leu Lys Leu Ile Val Asp Leu Met Tyr Glu
225                 230                 235                 240

Glu Gly Leu Ala Gly Met Arg Tyr Ser Ile Ser Asp Thr Ala Gln Trp
                245                 250                 255

Gly Asp Phe Val Ser Gly Pro Arg Val Val Asp Ala Lys Val Lys Glu
            260                 265                 270

Ser Met Lys Glu Val Leu Lys Asp Ile Gln Asn Gly Thr Phe Ala Lys
            275                 280                 285

Glu Trp Ile Val Glu Asn Gln Val Asn Arg Pro Arg Phe Asn Ala Ile
290                 295                 300

Asn Ala Ser Glu Asn Glu His Gln Ile Glu Val Val Gly Arg Lys Leu
305                 310                 315                 320

Arg Glu Met Met Pro Phe Val Lys Gln Gly Lys Lys Lys Glu Ala Val
                325                 330                 335

Val Ser Val Ala Gln Asn
            340

<210> SEQ ID NO 47
<211> LENGTH: 1758
<212> TYPE: DNA
<213> ORGANISM: Saccharomyces cerevisiae

<400> SEQUENCE: 47
atgggcttgt taacgaaagt tgctacatct agacaattct ctacaacgag atgcgttgca      60
aagaagctca acaagtactc gtatatcatc actgaaccta agggccaagg tgcgtcccag     120
gccatgcttt atgccaccgg tttcaagaag gaagatttca agaagcctca agtcggggtt     180
ggttcctgtt ggtggtccgg taacccatgt aacatgcatc tattggactt gaataacaga     240
tgttctcaat ccattgaaaa agcgggtttg aaagctatgc agttcaacac catcggtgtt     300
tcagacggta tctctatggg tactaaaggt atgagatact cgttacaaag tagagaaatc     360
attgcagact cctttgaaac catcatgatg gcacaacact acgatgctaa catcgccatc     420
```

```
ccatcatgtg acaaaaacat gcccggtgtc atgatggcca tgggtagaca taacagacct    480
tccatcatgg tatatggtgg tactatcttg cccggtcatc aacatgtggt tcttcgaag      540
atctctaaaa acatcgatat cgtctctgcg ttccaatcct acggtgaata tatttccaag    600
caattcactg aagaagaaag agaagatgtt gtggaacatg catgcccagg tcctggttct    660
tgtggtggta tgtatactgc aacacaatg gcttctgccg ctgaagtgct aggtttgacc     720
attccaaact cctcttcctt cccagccgtt tccaaggaga gttagctga gtgtgacaac     780
attggtgaat acatcaagaa gacaatggaa ttgggtattt acctcgtga tatcctcaca    840
aaagaggctt tgaaaacgc cattacttat gtcgttgcaa ccggtgggtc cactaatgct    900
gttttgcatt tggtggctgt tgctcactct gcgggtgtca agttgtcacc agatgatttc    960
caaagaatca gtgatactac accattgatc ggtgacttca aaccttctgg taaatacgtc   1020
atggccgatt tgattaacgt tggtggtacc caatctgtga ttaagtatct atatgaaaac   1080
aacatgttgc acggtaacac aatgactgtt accggtgaca ctttggcaga acgtgcaaag   1140
aaagcaccaa gcctacctga aggacaagag attattaagc cactctccca cccaatcaag   1200
gccaacggtc acttgcaaat tctgtacggt tcattggcac caggtggagc tgtgggtaaa   1260
attaccggta aggaaggtac ttacttcaag ggtagagcac gtgtgttcga agaggaaggt   1320
gcctttattg aagccttgga aagaggtgaa atcaagaagg gtgaaaaaac cgttgttgtt   1380
atcagatatg aaggtccaag aggtgcacca ggtatgcctg aaatgctaaa gccttcctct   1440
gctctgatgg gttacggttt gggtaaagat gttgcattgt tgactgatgg tagattctct   1500
ggtggttctc acgggttctt aatcggccac attgttcccg aagccgctga aggtggtcct   1560
atcgggttgg tcagagacgg cgatgagatt atcattgatg ctgataataa caagattgac   1620
ctattagtct ctgataagga aatggctcaa cgtaaacaaa gttgggttgc acctccacct   1680
cgttacacaa gaggtactct atccaagtat gctaagttgg tttccaacgc ttccaacggt   1740
tgtgttttag atgcttga                                                  1758

<210> SEQ ID NO 48
<211> LENGTH: 585
<212> TYPE: PRT
<213> ORGANISM: Saccharomyces cerevisiae

<400> SEQUENCE: 48

Met Gly Leu Leu Thr Lys Val Ala Thr Ser Arg Gln Phe Ser Thr Thr
1               5                   10                  15

Arg Cys Val Ala Lys Lys Leu Asn Lys Tyr Ser Tyr Ile Ile Thr Glu
                20                  25                  30

Pro Lys Gly Gln Gly Ala Ser Gln Ala Met Leu Tyr Ala Thr Gly Phe
            35                  40                  45

Lys Lys Glu Asp Phe Lys Lys Pro Gln Val Gly Val Gly Ser Cys Trp
        50                  55                  60

Trp Ser Gly Asn Pro Cys Asn Met His Leu Leu Asp Leu Asn Asn Arg
65                  70                  75                  80

Cys Ser Gln Ser Ile Glu Lys Ala Gly Leu Lys Ala Met Gln Phe Asn
                85                  90                  95

Thr Ile Gly Val Ser Asp Gly Ile Ser Met Gly Thr Lys Gly Met Arg
            100                 105                 110

Tyr Ser Leu Gln Ser Arg Glu Ile Ile Ala Asp Ser Phe Glu Thr Ile
        115                 120                 125

Met Met Ala Gln His Tyr Asp Ala Asn Ile Ala Ile Pro Ser Cys Asp
    130                 135                 140
```

-continued

```
Lys Asn Met Pro Gly Val Met Ala Met Gly Arg His Asn Arg Pro
145                 150                 155                 160

Ser Ile Met Val Tyr Gly Gly Thr Ile Leu Pro Gly His Pro Thr Cys
                165                 170                 175

Gly Ser Ser Lys Ile Ser Lys Asn Ile Asp Ile Val Ser Ala Phe Gln
            180                 185                 190

Ser Tyr Gly Glu Tyr Ile Ser Lys Gln Phe Thr Glu Glu Arg Glu
        195                 200                 205

Asp Val Val Glu His Ala Cys Pro Gly Pro Gly Ser Cys Gly Gly Met
    210                 215                 220

Tyr Thr Ala Asn Thr Met Ala Ser Ala Ala Glu Val Leu Gly Leu Thr
225                 230                 235                 240

Ile Pro Asn Ser Ser Phe Pro Ala Val Ser Lys Glu Lys Leu Ala
                245                 250                 255

Glu Cys Asp Asn Ile Gly Glu Tyr Ile Lys Lys Thr Met Glu Leu Gly
            260                 265                 270

Ile Leu Pro Arg Asp Ile Leu Thr Lys Glu Ala Phe Glu Asn Ala Ile
        275                 280                 285

Thr Tyr Val Val Ala Thr Gly Gly Ser Thr Asn Ala Val Leu His Leu
    290                 295                 300

Val Ala Val Ala His Ser Ala Gly Val Lys Leu Ser Pro Asp Phe
305                 310                 315                 320

Gln Arg Ile Ser Asp Thr Thr Pro Leu Ile Gly Asp Phe Lys Pro Ser
                325                 330                 335

Gly Lys Tyr Val Met Ala Asp Leu Ile Asn Val Gly Gly Thr Gln Ser
            340                 345                 350

Val Ile Lys Tyr Leu Tyr Glu Asn Asn Met Leu His Gly Asn Thr Met
        355                 360                 365

Thr Val Thr Gly Asp Thr Leu Ala Glu Arg Ala Lys Lys Ala Pro Ser
    370                 375                 380

Leu Pro Glu Gly Gln Glu Ile Ile Lys Pro Leu Ser His Pro Ile Lys
385                 390                 395                 400

Ala Asn Gly His Leu Gln Ile Leu Tyr Gly Ser Leu Ala Pro Gly Gly
                405                 410                 415

Ala Val Gly Lys Ile Thr Gly Lys Glu Gly Thr Tyr Phe Lys Gly Arg
            420                 425                 430

Ala Arg Val Phe Glu Glu Gly Ala Phe Ile Glu Ala Leu Glu Arg
        435                 440                 445

Gly Glu Ile Lys Lys Gly Glu Lys Thr Val Val Ile Arg Tyr Glu
    450                 455                 460

Gly Pro Arg Gly Ala Pro Gly Met Pro Glu Met Leu Lys Pro Ser Ser
465                 470                 475                 480

Ala Leu Met Gly Tyr Gly Leu Gly Lys Asp Val Ala Leu Leu Thr Asp
                485                 490                 495

Gly Arg Phe Ser Gly Gly Ser His Gly Phe Leu Ile Gly His Ile Val
            500                 505                 510

Pro Glu Ala Ala Glu Gly Gly Pro Ile Gly Leu Val Arg Asp Gly Asp
        515                 520                 525

Glu Ile Ile Ile Asp Ala Asp Asn Asn Lys Ile Asp Leu Leu Val Ser
    530                 535                 540

Asp Lys Glu Met Ala Gln Arg Lys Gln Ser Trp Val Ala Pro Pro
545                 550                 555                 560

Arg Tyr Thr Arg Gly Thr Leu Ser Lys Tyr Ala Lys Leu Val Ser Asn
```

Ala Ser Asn Gly Cys Val Leu Asp Ala
    580              585

<210> SEQ ID NO 49
<211> LENGTH: 4536
<212> TYPE: DNA
<213> ORGANISM: Saccharomyces cerevisiae

<400> SEQUENCE: 49

| | | | | |
|---|---|---|---|---|
| atgcccgagg | ccaagcttaa | caataacgtc | aacgacgtta | ctagctactc | ctccgcgtct | 60 |
| tcttctactg | aaaacgctgc | tgatctacac | aattataatg | ggttcgatga | gcatacagaa | 120 |
| gctcgaatcc | aaaaactggc | aaggactctg | accgcacaga | gtatgcaaaa | ctccactcaa | 180 |
| tcggcaccca | acaaaagtga | tgctcagtct | atattttcta | gcggtgtgga | aggtgtaaac | 240 |
| ccgatattct | ctgatcctga | agctccaggc | tatgacccaa | aattggaccc | caactccgaa | 300 |
| aattttttcta | gtgccgcctg | ggttaagaat | atggctcacc | taagtgcggc | agaccctgac | 360 |
| tttttataagc | cttattcctt | aggttgcgct | tggaagaact | taagtgcttc | tggtgcttcc | 420 |
| gcagatgtcg | cctatcagtc | aactgtggtt | aatattccat | acaaaatcct | aaaaagtggg | 480 |
| ctgagaaagt | ttcaacgttc | taaagaaacc | aatactttcc | aaatcttgaa | accaatggat | 540 |
| ggttgcctaa | acccaggtga | attgctagtc | gttttaggta | gaccaggctc | tggctgtact | 600 |
| actttattaa | aatccatctc | ttcaaatact | catggttttg | atcttggtgc | agatactaaa | 660 |
| atttcttaca | gcggctactc | aggtgatgat | attaagaaac | attttcgtgg | tgaagttgtt | 720 |
| tacaacgcag | aagctgatgt | acatctgcct | catttaacag | tcttcgaaac | tttggttaca | 780 |
| gtagcgaggt | tgaaaacccc | acagaaccgt | atcaagggtg | tcgataggga | agttatgcg | 840 |
| aatcatttgg | cggaagtagc | aatggcaacg | tacggtttat | cgcatacaag | gaatacaaaa | 900 |
| gttggtaacg | acatcgtcag | aggtgttttcc | ggtggtgaaa | ggaagcgtgt | ctccattgct | 960 |
| gaagtctcca | tctgtggatc | caaatttcaa | tgctgggata | atgctacaag | gggtttggat | 1020 |
| tccgctaccg | ctttggaatt | tattcgtgcc | ttaaagactc | aagctgatat | ttccaataca | 1080 |
| tctgccacag | tggccatcta | tcaatgttct | caagatgcgt | acgacttgtt | caataaagtc | 1140 |
| tgtgttttgg | atgatggtta | tcagatctac | tatggccccg | ccgataaggc | caagaagtac | 1200 |
| tttgaagata | tgggggtatgt | tgtccaagc | agacaaacca | ccgcagatt | tttgacctca | 1260 |
| gttacaagtc | cctctgagag | aaccctgaac | aaagatatgc | taaaaaaagg | tattcatata | 1320 |
| ccacagaccc | cgaaggaaat | gaacgattac | tgggtaaaat | ctccaaatta | caaagagcta | 1380 |
| atgaaagaag | tcgaccaacg | attattgaat | gacgatgaag | caagccgtga | agctattaag | 1440 |
| gaagcccaca | ttgctaagca | gtccaagaga | gcaagacctt | cctctcctta | tactgtcagc | 1500 |
| tacatgatgc | aagttaaata | cctattaatc | agaaatatgt | ggagactgcg | aaataatatc | 1560 |
| gggtttacat | tatttatgat | tttgggtaac | tgtagtatgg | ctttaatctt | gggttcaatg | 1620 |
| ttttttcaaga | tcatgaaaaa | gggtgatact | tctacattct | atttccgtgg | ttctgctatg | 1680 |
| ttttttgcaa | ttctattcaa | tgcatttttct | tctctgttag | aaatcttttc | gttatatgag | 1740 |
| gccagaccaa | tcactgaaaa | acatagaaca | tattcgttat | accatccaag | tgctgacgct | 1800 |
| tttgcatcag | ttctatcaga | aatacccctca | aagttaatca | tcgctgtttg | cttcaatata | 1860 |
| atcttctatt | tcttagtaga | ctttagaaga | aatggtggtg | tattctttttt | ctacttatta | 1920 |
| ataaacattg | tcgcggtttt | ctccatgtct | cacttgttta | gatgtgttgg | ttccttaaca | 1980 |
| aagacattgt | cagaagctat | ggttcccgct | tctatgttat | tgttggctct | atccatgtat | 2040 |

```
accggttttg ctattcctaa gaagaagatc ctacgttggt ctaaatggat ttggtatatc    2100
aatccgttgg cttacttatt cgaatctttg ttaattaacg agtttcatgg tataaaattc    2160
ccctgcgctg aatatgttcc tcgtggtcct gcgtatgcaa acatttctag tacagaatct    2220
gtttgtaccg tggttggagc tgttccaggc caagactatg ttctgggtga tgatttcatt    2280
agaggaactt atcaatacta ccacaaagac aaatggcgtg gtttcggtat tggtatggct    2340
tatgtcgtct tcttttttctt tgtctatcta ttcttatgtg aatacaacga gggtgctaaa    2400
caaaaaggtg aaatattagt tttcccacgc agtatagtta aaagaatgaa gaaaagaggt    2460
gtactaactg aaaagaatgc aaatgacccc gaaaacgttg gggaacgtag tgacttatcc    2520
agcgatagga aaatgctaca agaaagctct gaagaggaat ccgatactta cggagaaatt    2580
ggtttatcca agtcagaggc tatatttcac tggagaaacc tttgttacga agttcagatt    2640
aaggccgaaa caagacgtat tttgaacaat gttgatggtt gggttaaacc aggtacttta    2700
acagctttaa tgggtgcttc aggtgctggt aaaaccacac ttctggattg tttggccgaa    2760
agggttacca tgggtgttat aactggtgat atcttggtca atggtattcc ccgtgataaa    2820
tctttcccaa gatccattgg ttattgtcag caacaagatt tgcatttgaa aactgccact    2880
gtgagggagt cattgagatt ttctgcttac ctacgtcaac cagctgaagt ttccattgaa    2940
gaaaagaaca gatatgttga agaagttatt aaaattcttg aaatggaaaa atatgctgat    3000
gctgttgttg gtgttgctgg tgaaggttta acgttgaac aaagaaaaag attaaccatt    3060
ggtgttgaat taactgccaa accaaaactg ttggtctttt tagatgaacc tacttctggt    3120
ttggattctc aaactgcttg gtctatttgt cagctaatga aaagttggc aaatcatggt    3180 caagcaattc tatgtactat tcaccaaccc tctgctattt tgatgcaaga attcgatcgt    3240
ttactattta tgcaacgtgg tggtaagact gtctactttg gcgacttggg cgaaggttgt    3300
aaaactatga tcgattattt tgaaagccat ggtgctcata atgccctgc tgacgccaac    3360 ccagctgaat ggatgctaga agttgttggt gcagctccag gctctcatgc aaatcaagat    3420
tattacgaag tttggaggaa ttctgaagag tacagggccg ttcaatctga attagattgg    3480
atggaaagag aattaccaaa gaaaggttcg ataactgcag ctgaggacaa acacgaattt    3540
tcacaatcaa ttatttatca aacaaaattg gtcagtattc gtctattcca gcaatattgg    3600
agatctccag attatttatg gtcgaagttt atttttaacta ttttcaatca attgttcatc    3660
ggtttcactt tcttcaaagc aggaacctcg ctacagggtt tacaaaatca aatgttggct    3720
gtgttcatgt ttacggttat tttcaatcct attctacaac aatacctacc atcttttgtc    3780
cagcaaagag atttgtatga ggccagggaa cgcccctcaa ggactttttc ttggatttca    3840
tttatcttcg ctcaaatatt cgtggaagtt ccatggaata tattggcagg tactattgct    3900
tattttatct actattatcc aattggattt tactccaacg cgtctgcagc tggccagttg    3960
catgaaaggg gtgctttatt ttggttgttc tcttgtgctt tctacgttta tgttggttct    4020
atgggtctgc ttgtcatttc attcaaccaa gttgcagaaa gtgcagctaa cttagcctct    4080
ttgttgttta caatgtcttt gtcttttttgt ggtgttatga ctaccccaag tgccatgcct    4140
agattttgga tattcatgta cagggtttca cctttgactt atttcattca ggctctgttg    4200
gctgttggtg ttgctaacgt agacgtcaaa tgcgctgatt acgaattgct agaattcaca    4260
ccaccatccg gtatgacatg tgggcagtac atggaaccat atttacaact agcaaagact    4320
ggttacttaa ctgatgaaaa tgccactgac acctgtagtt tctgtcaaat atctacaacc    4380
aatgattact tagctaatgt caattctttc tacagtgaga gatggagaaa ttatggtatc    4440
```

```
ttcatctgtt atattgcatt caattatatc gctggtgtct ttttctactg gttagcaaga    4500
gtgcctaaaa agaacggtaa actctccaag aaataa                              4536
```

<210> SEQ ID NO 50
<211> LENGTH: 1511
<212> TYPE: PRT
<213> ORGANISM: Saccharomyces cerevisiae

<400> SEQUENCE: 50

```
Met Pro Glu Ala Lys Leu Asn Asn Val Asn Asp Val Thr Ser Tyr
1               5                   10                  15

Ser Ser Ala Ser Ser Ser Thr Glu Asn Ala Ala Asp Leu His Asn Tyr
                20                  25                  30

Asn Gly Phe Asp Glu His Thr Glu Ala Arg Ile Gln Lys Leu Ala Arg
            35                  40                  45

Thr Leu Thr Ala Gln Ser Met Gln Asn Ser Thr Gln Ser Ala Pro Asn
        50                  55                  60

Lys Ser Asp Ala Gln Ser Ile Phe Ser Ser Gly Val Glu Gly Val Asn
65                  70                  75                  80

Pro Ile Phe Ser Asp Pro Glu Ala Pro Gly Tyr Asp Pro Lys Leu Asp
                85                  90                  95

Pro Asn Ser Glu Asn Phe Ser Ser Ala Ala Trp Val Lys Asn Met Ala
            100                 105                 110

His Leu Ser Ala Ala Asp Pro Asp Phe Tyr Lys Pro Tyr Ser Leu Gly
        115                 120                 125

Cys Ala Trp Lys Asn Leu Ser Ala Ser Gly Ala Ser Ala Asp Val Ala
    130                 135                 140

Tyr Gln Ser Thr Val Val Asn Ile Pro Tyr Lys Ile Leu Lys Ser Gly
145                 150                 155                 160

Leu Arg Lys Phe Gln Arg Ser Lys Glu Thr Asn Thr Phe Gln Ile Leu
                165                 170                 175

Lys Pro Met Asp Gly Cys Leu Asn Pro Gly Glu Leu Leu Val Val Leu
            180                 185                 190

Gly Arg Pro Gly Ser Gly Cys Thr Thr Leu Leu Lys Ser Ile Ser Ser
        195                 200                 205

Asn Thr His Gly Phe Asp Leu Gly Ala Asp Thr Lys Ile Ser Tyr Ser
    210                 215                 220

Gly Tyr Ser Gly Asp Asp Ile Lys Lys His Phe Arg Gly Glu Val Val
225                 230                 235                 240

Tyr Asn Ala Glu Ala Asp Val His Leu Pro His Leu Thr Val Phe Glu
                245                 250                 255

Thr Leu Val Thr Val Ala Arg Leu Lys Thr Pro Gln Asn Arg Ile Lys
            260                 265                 270

Gly Val Asp Arg Glu Ser Tyr Ala Asn His Leu Ala Glu Val Ala Met
        275                 280                 285

Ala Thr Tyr Gly Leu Ser His Thr Arg Asn Thr Lys Val Gly Asn Asp
    290                 295                 300

Ile Val Arg Gly Val Ser Gly Gly Glu Arg Lys Arg Val Ser Ile Ala
305                 310                 315                 320

Glu Val Ser Ile Cys Gly Ser Lys Phe Gln Cys Trp Asp Asn Ala Thr
                325                 330                 335

Arg Gly Leu Asp Ser Ala Thr Ala Leu Glu Phe Ile Arg Ala Leu Lys
            340                 345                 350

Thr Gln Ala Asp Ile Ser Asn Thr Ser Ala Thr Val Ala Ile Tyr Gln
```

-continued

|     | 355 |     |     |     | 360 |     |     |     | 365 |     |     |
| --- | --- | --- | --- | --- | --- | --- | --- | --- | --- | --- | --- |

Cys Ser Gln Asp Ala Tyr Asp Leu Phe Asn Lys Val Cys Val Leu Asp
370                     375                     380

Asp Gly Tyr Gln Ile Tyr Tyr Gly Pro Ala Asp Lys Ala Lys Lys Tyr
385                     390                     395                     400

Phe Glu Asp Met Gly Tyr Val Cys Pro Ser Arg Gln Thr Thr Ala Asp
                        405                     410                     415

Phe Leu Thr Ser Val Thr Ser Pro Ser Glu Arg Thr Leu Asn Lys Asp
                420                     425                     430

Met Leu Lys Lys Gly Ile His Ile Pro Gln Thr Pro Lys Glu Met Asn
                435                     440                     445

Asp Tyr Trp Val Lys Ser Pro Asn Tyr Lys Glu Leu Met Lys Glu Val
450                     455                     460

Asp Gln Arg Leu Leu Asn Asp Asp Glu Ala Ser Arg Glu Ala Ile Lys
465                     470                     475                     480

Glu Ala His Ile Ala Lys Gln Ser Lys Arg Ala Arg Pro Ser Ser Pro
                485                     490                     495

Tyr Thr Val Ser Tyr Met Met Gln Val Lys Tyr Leu Leu Ile Arg Asn
                500                     505                     510

Met Trp Arg Leu Arg Asn Asn Ile Gly Phe Thr Leu Phe Met Ile Leu
                515                     520                     525

Gly Asn Cys Ser Met Ala Leu Ile Leu Gly Ser Met Phe Phe Lys Ile
530                     535                     540

Met Lys Lys Gly Asp Thr Ser Thr Phe Tyr Phe Arg Gly Ser Ala Met
545                     550                     555                     560

Phe Phe Ala Ile Leu Phe Asn Ala Phe Ser Ser Leu Leu Glu Ile Phe
                565                     570                     575

Ser Leu Tyr Glu Ala Arg Pro Ile Thr Glu Lys His Arg Thr Tyr Ser
                580                     585                     590

Leu Tyr His Pro Ser Ala Asp Ala Phe Ala Ser Val Leu Ser Glu Ile
                595                     600                     605

Pro Ser Lys Leu Ile Ile Ala Val Cys Phe Asn Ile Ile Phe Tyr Phe
610                     615                     620

Leu Val Asp Phe Arg Arg Asn Gly Gly Val Phe Phe Phe Tyr Leu Leu
625                     630                     635                     640

Ile Asn Ile Val Ala Val Phe Ser Met Ser His Leu Phe Arg Cys Val
                645                     650                     655

Gly Ser Leu Thr Lys Thr Leu Ser Glu Ala Met Val Pro Ala Ser Met
                660                     665                     670

Leu Leu Leu Ala Leu Ser Met Tyr Thr Gly Phe Ala Ile Pro Lys Lys
                675                     680                     685

Lys Ile Leu Arg Trp Ser Lys Trp Ile Trp Tyr Ile Asn Pro Leu Ala
                690                     695                     700

Tyr Leu Phe Glu Ser Leu Leu Ile Asn Glu Phe His Gly Ile Lys Phe
705                     710                     715                     720

Pro Cys Ala Glu Tyr Val Pro Arg Gly Pro Ala Tyr Ala Asn Ile Ser
                725                     730                     735

Ser Thr Glu Ser Val Cys Thr Val Val Gly Ala Val Pro Gly Gln Asp
                740                     745                     750

Tyr Val Leu Gly Asp Asp Phe Ile Arg Gly Thr Tyr Gln Tyr Tyr His
                755                     760                     765

Lys Asp Lys Trp Arg Gly Phe Gly Ile Gly Met Ala Tyr Val Val Phe
770                     775                     780

-continued

Phe Phe Phe Val Tyr Leu Phe Leu Cys Glu Tyr Asn Glu Gly Ala Lys
785                 790                 795                 800

Gln Lys Gly Glu Ile Leu Val Phe Pro Arg Ser Ile Val Lys Arg Met
        805                 810                 815

Lys Lys Arg Gly Val Leu Thr Glu Lys Asn Ala Asn Asp Pro Glu Asn
            820                 825                 830

Val Gly Glu Arg Ser Asp Leu Ser Ser Asp Arg Lys Met Leu Gln Glu
                835                 840                 845

Ser Ser Glu Glu Glu Ser Asp Thr Tyr Gly Glu Ile Gly Leu Ser Lys
850                 855                 860

Ser Glu Ala Ile Phe His Trp Arg Asn Leu Cys Tyr Glu Val Gln Ile
865                 870                 875                 880

Lys Ala Glu Thr Arg Arg Ile Leu Asn Asn Val Asp Gly Trp Val Lys
                885                 890                 895

Pro Gly Thr Leu Thr Ala Leu Met Gly Ala Ser Gly Ala Gly Lys Thr
                900                 905                 910

Thr Leu Leu Asp Cys Leu Ala Glu Arg Val Thr Met Gly Val Ile Thr
            915                 920                 925

Gly Asp Ile Leu Val Asn Gly Ile Pro Arg Asp Lys Ser Phe Pro Arg
930                 935                 940

Ser Ile Gly Tyr Cys Gln Gln Asp Leu His Leu Lys Thr Ala Thr
945                 950                 955                 960

Val Arg Glu Ser Leu Arg Phe Ser Ala Tyr Leu Arg Gln Pro Ala Glu
                965                 970                 975

Val Ser Ile Glu Glu Lys Asn Arg Tyr Val Glu Glu Val Ile Lys Ile
                980                 985                 990

Leu Glu Met Glu Lys Tyr Ala Asp Ala Val Val Gly Val Ala Gly Glu
            995                 1000                1005

Gly Leu Asn Val Glu Gln Arg Lys Arg Leu Thr Ile Gly Val Glu
    1010                1015                1020

Leu Thr Ala Lys Pro Lys Leu Leu Val Phe Leu Asp Glu Pro Thr
    1025                1030                1035

Ser Gly Leu Asp Ser Gln Thr Ala Trp Ser Ile Cys Gln Leu Met
    1040                1045                1050

Lys Lys Leu Ala Asn His Gly Gln Ala Ile Leu Cys Thr Ile His
    1055                1060                1065

Gln Pro Ser Ala Ile Leu Gln Glu Phe Asp Arg Leu Leu Phe
    1070                1075                1080

Met Gln Arg Gly Gly Lys Thr Val Tyr Phe Gly Asp Leu Gly Glu
    1085                1090                1095

Gly Cys Lys Thr Met Ile Asp Tyr Phe Glu Ser His Gly Ala His
    1100                1105                1110

Lys Cys Pro Ala Asp Ala Asn Pro Ala Glu Trp Met Leu Glu Val
    1115                1120                1125

Val Gly Ala Ala Pro Gly Ser His Ala Asn Gln Asp Tyr Tyr Glu
    1130                1135                1140

Val Trp Arg Asn Ser Glu Glu Tyr Arg Ala Val Gln Ser Glu Leu
    1145                1150                1155

Asp Trp Met Glu Arg Glu Leu Pro Lys Lys Gly Ser Ile Thr Ala
    1160                1165                1170

Ala Glu Asp Lys His Glu Phe Ser Gln Ser Ile Ile Tyr Gln Thr
    1175                1180                1185

Lys Leu Val Ser Ile Arg Leu Phe Gln Gln Tyr Trp Arg Ser Pro
    1190                1195                1200

```
Asp Tyr Leu Trp Ser Lys Phe Ile Leu Thr Ile Phe Asn Gln Leu
    1205                1210                1215

Phe Ile Gly Phe Thr Phe Pro Lys Ala Gly Thr Ser Leu Gln Gly
    1220                1225                1230

Leu Gln Asn Gln Met Leu Ala Val Phe Met Phe Thr Val Ile Phe
    1235                1240                1245

Asn Pro Ile Leu Gln Gln Tyr Leu Pro Ser Phe Gln Gln Arg
    1250                1255                1260

Asp Leu Tyr Glu Ala Arg Glu Arg Pro Ser Arg Thr Phe Ser Trp
    1265                1270                1275

Ile Ser Phe Ile Phe Ala Gln Ile Phe Val Glu Val Pro Trp Asn
    1280                1285                1290

Ile Leu Ala Gly Thr Ile Ala Tyr Phe Ile Tyr Tyr Tyr Pro Ile
    1295                1300                1305

Gly Phe Tyr Ser Asn Ala Ser Ala Ala Gly Gln Leu His Glu Arg
    1310                1315                1320

Gly Ala Leu Phe Trp Leu Phe Ser Cys Ala Phe Tyr Val Tyr Val
    1325                1330                1335

Gly Ser Met Gly Leu Leu Val Ile Ser Phe Asn Gln Val Ala Glu
    1340                1345                1350

Ser Ala Ala Asn Leu Ala Ser Leu Leu Phe Thr Met Ser Leu Ser
    1355                1360                1365

Phe Cys Gly Val Met Thr Thr Pro Ser Ala Met Pro Arg Phe Trp
    1370                1375                1380

Ile Phe Met Tyr Arg Val Ser Pro Leu Thr Tyr Phe Ile Gln Ala
    1385                1390                1395

Leu Leu Ala Val Gly Val Ala Asn Val Asp Val Lys Cys Ala Asp
    1400                1405                1410

Tyr Glu Leu Leu Glu Phe Thr Pro Pro Ser Gly Met Thr Cys Gly
    1415                1420                1425

Gln Tyr Met Glu Pro Tyr Leu Gln Leu Ala Lys Thr Gly Tyr Leu
    1430                1435                1440

Thr Asp Glu Asn Ala Thr Asp Thr Cys Ser Phe Cys Gln Ile Ser
    1445                1450                1455

Thr Thr Asn Asp Tyr Leu Ala Asn Val Asn Ser Phe Tyr Ser Glu
    1460                1465                1470

Arg Trp Arg Asn Tyr Gly Ile Phe Ile Cys Tyr Ile Ala Phe Asn
    1475                1480                1485

Tyr Ile Ala Gly Val Phe Phe Tyr Trp Leu Ala Arg Val Pro Lys
    1490                1495                1500

Lys Asn Gly Lys Leu Ser Lys Lys
    1505                1510

<210> SEQ ID NO 51
<211> LENGTH: 4506
<212> TYPE: DNA
<213> ORGANISM: Candida albicans

<400> SEQUENCE: 51
atgtcagatt ctaagatgtc gtcgcaagat gaatctaaat tagaaaaggc aattagtcaa     60
gactcttctt cagaaaacca ttccattaat gaataccacg ggtttgatgc ccatacaagt    120 gaaacattc agaatttagc cagaactttc actcatgatt ctttcaaaga tgactcgtca     180
gcaggtttat tgaaatactt aacccatatg tcagaagtgc ccggggtcaa tccatatgaa    240
```

```
catgaagaaa taaataatga ccaattgaat cccgattcag aaaatttcaa tgccaaattt      300
tgggttaaaa atttaagaaa attgtttgaa tcagatcctg aatattataa accttcgaaa      360
ttgggaattg gatatagaaa tttaagagca tatggtgttg ctaatgattc tgattatcaa      420
ccaactgtta ctaacgcact ttggaaatta gccacagaag gtttcagaca tttccaaaaa      480
gatgatgact caagatattt tgatattttg aaatcaatgg atgccattat gagaccaggt      540
gaacttactg ttgttttggg gagacccggt gctggttgtt ccacattgtt aaagaccatt      600
gctgttaaca cttatggttt ccacattggt aaagaatccc aaattactta tgatgggtta      660
tccccacatg atattgaacg tcattaccgt ggtgatgtta tttattctgc tgaaaccgat      720
gttcatttcc ctcatttgag tgttggtgat actttggaat tgccgctag attaagaact      780 ccacaaaaca gaggtgaagg tatcgacaga gaaacttatg ctaaacacat ggctagtgtt      840
tatatggcaa cctatgggtt atcacacaca agaaatacta atgttggtaa cgatttcgtc      900
cgtggtgttt ccggtggtga aggaaaaga gtgtcaattg ctgaagcttc tttgagtggt      960
gctaatatcc aatgttggga taatgccact agagggttag attctgctac tgctttggaa     1020
ttcattagag ctttgaaaac ttcagcagtc attttagata ccaccccttt aattgctatt     1080
tatcaatgtt ctcaagatgc ctatgattta tttgataaag ttgttgtctt gtatgaaggt     1140
tatcaaattt tctttggtaa agccaccaag gctaaagaat attttgaaaa gatgggttgg     1200
aaatgtcctc aaagacaaac tactgctgat ttcttgactt ccttaaccaa tccagctgaa     1260
agagaaccat taccaggtta tgaagataaa gtgccaagaa ctgctcaaga atttgaaaca     1320
tattggaaaa attctcccga atatgctgaa ttaactaagg aaattgatga atattttgtt     1380
gaatgtgaac gatccaacac cagggaaact tatcgtgaat ctcatgttgc caaacaatcc     1440
aacaatacaa gaccagcatc tccatatact gtatcattct tcatgcaagt gaggtatggt     1500
gttgcgagaa atttccttcg tatgaaaggt gatccgtcga ttcctatatt ttccgttttc     1560
ggtcaacttg taatgggtct catattgtcg tcggtgttct ataatcttag tcaaaccact     1620
ggatcgtttt attatagagg tgctgccatg ttctttgctg ttttgtttaa tgccttttca     1680
tcacttttgg aaatcatgtc actttttcgaa gccagaccaa ttgtcgagaa acataaaaaa     1740
tatgcccttt atcgtccttc agctgatgcc ttggccagta ttattagtga attacctgtc     1800
aaattagcca tgtcaatgtc atttaatttt gtgttttatt ttatggttaa tttagaaga      1860 aatccaggta gattcttttt ctattggtta atgtgtattt ggtgtacatt tgttatgtcc     1920
catttgttta gatccattgg tgctgtttca acatctattt ctggtgccat gactcctgct     1980
accgtgttgt tattggctat ggttatttat actgggttcg ttatcccaac tccaagtatg     2040
ttgggttggt ctcgatggat taattatatt aaccctgttg gttatgtgtt tgaatccctt     2100
atggttaatg aattccacgg tcgtgaattc caatgtgctc aatatgttcc aagtggtcca     2160
ggttatgaaa atatatcacg ttcaaatcaa gtgtgtactg cagtggggtc tgttccaggt     2220
aatgaaatgg ttagtggtac caattatttg gctggtgctt atcaatatta caattctcat     2280
aaatggagaa acttgggtat taccattgga tttgccgtat tcttttttggc catttatatt     2340 gctttaactg aattcaataa aggtgctatg caaaaggggg aaattgtttt gttcctcaaa     2400
gggtcattga aaaacataa aagaaaaact gctgcttcca acaaaggtga tattgaagct     2460
ggtcctgttg ctggcaaact tgattatcaa gatgaagctg aagctgttaa taatgaaaaa     2520
ttcactgaaa agggtagtac tggaagtgtt gatttcccag aaaaccgtga atatttttc      2580 tggagagatt tgacttatca agttaaaatc aagaaagaag atcgtgttat tttagatcat     2640
```

```
gttgatggat gggtcaaacc aggtcaaatt actgcattga tgggagcatc tggtgctggt    2700
aagactacat tattgaattg tttatctgaa agagtcacta ctggtattat tactgatggt    2760
gaaagattgg ttaatggcca tgccttagat tcttcattcc aaagatcaat tggttatgtc    2820
caacaacaag acgttcattt ggaaaccact actgttagag aagcattaca attttctgct    2880
tatttgagac aatccaacaa gatttctaaa aaggagaaag atgattatgt cgattatgtt    2940
attgatttat tggaaatgac tgattatgct gatgccctag ttggtgtcgc tggtgaaggt    3000
ttgaatgttg aacaaagaaa aagattgacc attggggttg aattagttgc caaacctaaa    3060
ttgttgttat tcttagatga accagcttca gggttagatt ctcaaactgc ctggtcgatt    3120
tgtaaattga tgagaaagtt agctgatcat ggtcaagcca ttttgtgtac tatccatcaa    3180
ccatcagcac ttattatggc tgagtttgat agacttttat ttttacaaaa aggtggaaga    3240
acggcttatt ttggtgaatt aggtgagaac tgtcaaacca tgatcaatta ttttgaaaaa    3300
tatggtgctg atccatgtcc taaggaagca aatccagcag aatggatgtt acaagttgtt    3360
ggtgctgcac caggttcaca tgccaaacaa gattattttg aagtttggag aaattctagt    3420
gaatatcaag ctgttagaga agaaattaat agaatggaag ctgaattatc taaattacca    3480
agagataatg atccagaagc gcttttgaaa tatgctgcac cactttggaa acaatactta    3540
ttggtcagtt ggagaactat tgttcaagat tggagatcac caggatatat ttattctaaa    3600 atcttttttgg ttgtttcagc agctttattt aatggatttt cattttcaa agctaaaaat    3660 aacatgcaag gttacaaaaa tcaaatgttt tcggtgttta tgttttcat tccattcaat    3720 actttggtgc aacaaatgtt accatacttt gtgaagcaac gtgatgttta tgaagtgaga    3780
gaagctccat caagaacatt cagttggttt gcatttattg ccggtcaaat tacatcagaa    3840
attccttatc aagttgccgt tggtaccata gcattttct gttggtatta tccattagga    3900
ttgtataata atgctacacc aactgattct gtcaatcctc gaggtgtttt aatgtggatg    3960
cttgttactg cattttatgt ttacacagca accatgggtc aattatgtat gtctttcagt    4020
gaattagctg ataatgctgc caatttggct acattgttat ttactatgtg tttgaatttc    4080
tgtggtgttt tagctggtcc tgatgtatta ccaggatttt ggattttcat gtacagatgt    4140
aatccattca cttatttggt tcaagctatg ctttctactg gattagctaa cacttttgtt    4200
aaatgtgctg aacgtgaata tgtttcagtt aaaccaccaa atggtgaatc ttgttctact    4260
tatttggatc catacattaa atttgctggt gggtattttg aaactagaaa tgatggatct    4320
tgtgcattct gtcaaatgag ttccaccaat actttcttga aatcagttaa ttcattatac    4380
agtgaaagat ggagaaattt cggtatttc attgctttca ttgctattaa tatcattctt    4440
acggtgatct tttattggtt agctagagtt ccaaagggta acagagagaa aaaaaataag    4500
aaataa                                                              4506
```

<210> SEQ ID NO 52
<211> LENGTH: 1501
<212> TYPE: PRT
<213> ORGANISM: Candida albicans

<400> SEQUENCE: 52

Met Ser Asp Ser Lys Met Ser Ser Gln Asp Glu Ser Lys Leu Glu Lys
1               5                   10                  15

Ala Ile Ser Gln Asp Ser Ser Ser Glu Asn His Ser Ile Asn Glu Tyr
                20                  25                  30

His Gly Phe Asp Ala His Thr Ser Glu Asn Ile Gln Asn Leu Ala Arg
            35                  40                  45

```
Thr Phe Thr His Asp Ser Phe Lys Asp Asp Ser Ala Gly Leu Leu
    50                  55                  60

Lys Tyr Leu Thr His Met Ser Glu Val Pro Gly Val Asn Pro Tyr Glu
65                  70                  75                  80

His Glu Glu Ile Asn Asn Asp Gln Leu Asn Pro Asp Ser Glu Asn Phe
                85                  90                  95

Asn Ala Lys Phe Trp Val Lys Asn Leu Arg Lys Leu Phe Glu Ser Asp
            100                 105                 110

Pro Glu Tyr Tyr Lys Pro Ser Lys Leu Gly Ile Gly Tyr Arg Asn Leu
            115                 120                 125

Arg Ala Tyr Gly Val Ala Asn Asp Ser Asp Tyr Gln Pro Thr Val Thr
130                 135                 140

Asn Ala Leu Trp Lys Leu Ala Thr Glu Gly Phe Arg His Phe Gln Lys
145                 150                 155                 160

Asp Asp Asp Ser Arg Tyr Phe Asp Ile Leu Lys Ser Met Asp Ala Ile
                165                 170                 175

Met Arg Pro Gly Glu Leu Thr Val Val Leu Gly Arg Pro Gly Ala Gly
            180                 185                 190

Cys Ser Thr Leu Leu Lys Thr Ile Ala Val Asn Thr Tyr Gly Phe His
            195                 200                 205

Ile Gly Lys Glu Ser Gln Ile Thr Tyr Asp Gly Leu Ser Pro His Asp
210                 215                 220

Ile Glu Arg His Tyr Arg Gly Asp Val Ile Tyr Ser Ala Glu Thr Asp
225                 230                 235                 240

Val His Phe Pro His Leu Ser Val Gly Asp Thr Leu Glu Phe Ala Ala
                245                 250                 255

Arg Leu Arg Thr Pro Gln Asn Arg Gly Glu Gly Ile Asp Arg Glu Thr
            260                 265                 270

Tyr Ala Lys His Met Ala Ser Val Tyr Met Ala Thr Tyr Gly Leu Ser
            275                 280                 285

His Thr Arg Asn Thr Asn Val Gly Asn Asp Phe Val Arg Gly Val Ser
    290                 295                 300

Gly Gly Glu Arg Lys Arg Val Ser Ile Ala Glu Ala Ser Leu Ser Gly
305                 310                 315                 320

Ala Asn Ile Gln Cys Trp Asp Asn Ala Thr Arg Gly Leu Asp Ser Ala
                325                 330                 335

Thr Ala Leu Glu Phe Ile Arg Ala Leu Lys Thr Ser Ala Val Ile Leu
            340                 345                 350

Asp Thr Thr Pro Leu Ile Ala Ile Tyr Gln Cys Ser Gln Asp Ala Tyr
            355                 360                 365

Asp Leu Phe Asp Lys Val Val Val Leu Tyr Glu Gly Tyr Gln Ile Phe
    370                 375                 380

Phe Gly Lys Ala Thr Lys Ala Lys Glu Tyr Phe Glu Lys Met Gly Trp
385                 390                 395                 400

Lys Cys Pro Gln Arg Gln Thr Thr Ala Asp Phe Leu Thr Ser Leu Thr
                405                 410                 415

Asn Pro Ala Glu Arg Glu Pro Leu Pro Gly Tyr Glu Asp Lys Val Pro
            420                 425                 430

Arg Thr Ala Gln Glu Phe Glu Tyr Trp Lys Asn Ser Pro Glu Tyr
            435                 440                 445

Ala Glu Leu Thr Lys Glu Ile Asp Glu Tyr Phe Val Glu Cys Glu Arg
    450                 455                 460

Ser Asn Thr Arg Glu Thr Tyr Arg Glu Ser His Val Ala Lys Gln Ser
```

-continued

```
            465                 470                 475                 480
Asn Asn Thr Arg Pro Ala Ser Pro Tyr Thr Val Ser Phe Phe Met Gln
                        485                 490                 495
Val Arg Tyr Gly Val Ala Arg Asn Phe Leu Arg Met Lys Gly Asp Pro
            500                 505                 510
Ser Ile Pro Ile Phe Ser Val Phe Gly Gln Leu Val Met Gly Leu Ile
            515                 520                 525
Leu Ser Ser Val Phe Tyr Asn Leu Ser Gln Thr Thr Gly Ser Phe Tyr
            530                 535                 540
Tyr Arg Gly Ala Ala Met Phe Phe Ala Val Leu Phe Asn Ala Phe Ser
545                 550                 555                 560
Ser Leu Leu Glu Ile Met Ser Leu Phe Glu Ala Arg Pro Ile Val Glu
                565                 570                 575
Lys His Lys Lys Tyr Ala Leu Tyr Arg Pro Ser Ala Asp Ala Leu Ala
                580                 585                 590
Ser Ile Ile Ser Glu Leu Pro Val Lys Leu Ala Met Ser Met Ser Phe
            595                 600                 605
Asn Phe Val Phe Tyr Phe Met Val Asn Phe Arg Arg Asn Pro Gly Arg
            610                 615                 620
Phe Phe Phe Tyr Trp Leu Met Cys Ile Trp Cys Thr Phe Val Met Ser
625                 630                 635                 640
His Leu Phe Arg Ser Ile Gly Ala Val Ser Thr Ser Ile Ser Gly Ala
                645                 650                 655
Met Thr Pro Ala Thr Val Leu Leu Leu Ala Met Val Ile Tyr Thr Gly
                660                 665                 670
Phe Val Ile Pro Thr Pro Ser Met Leu Gly Trp Ser Arg Trp Ile Asn
            675                 680                 685
Tyr Ile Asn Pro Val Gly Tyr Val Phe Glu Ser Leu Met Val Asn Glu
            690                 695                 700
Phe His Gly Arg Glu Phe Gln Cys Ala Gln Tyr Val Pro Ser Gly Pro
705                 710                 715                 720
Gly Tyr Glu Asn Ile Ser Arg Ser Asn Gln Val Cys Thr Ala Val Gly
                725                 730                 735
Ser Val Pro Gly Asn Glu Met Val Ser Gly Thr Asn Tyr Leu Ala Gly
            740                 745                 750
Ala Tyr Gln Tyr Tyr Asn Ser His Lys Trp Arg Asn Leu Gly Ile Thr
            755                 760                 765
Ile Gly Phe Ala Val Phe Phe Leu Ala Ile Tyr Ile Ala Leu Thr Glu
        770                 775                 780
Phe Asn Lys Gly Ala Met Gln Lys Gly Glu Ile Val Leu Phe Leu Lys
785                 790                 795                 800
Gly Ser Leu Lys Lys His Lys Arg Lys Thr Ala Ala Ser Asn Lys Gly
                805                 810                 815
Asp Ile Glu Ala Gly Pro Val Ala Gly Lys Leu Asp Tyr Gln Asp Glu
            820                 825                 830
Ala Glu Ala Val Asn Asn Glu Lys Phe Thr Glu Lys Gly Ser Thr Gly
            835                 840                 845
Ser Val Asp Phe Pro Glu Asn Arg Glu Ile Phe Phe Trp Arg Asp Leu
            850                 855                 860
Thr Tyr Gln Val Lys Ile Lys Lys Glu Asp Arg Val Ile Leu Asp His
865                 870                 875                 880
Val Asp Gly Trp Val Lys Pro Gly Gln Ile Thr Ala Leu Met Gly Ala
                885                 890                 895
```

-continued

Ser Gly Ala Gly Lys Thr Thr Leu Leu Asn Cys Leu Ser Glu Arg Val
                900                 905                 910

Thr Thr Gly Ile Ile Thr Asp Gly Glu Arg Leu Val Asn Gly His Ala
                915                 920                 925

Leu Asp Ser Ser Phe Gln Arg Ser Ile Gly Tyr Val Gln Gln Gln Asp
                930                 935                 940

Val His Leu Glu Thr Thr Thr Val Arg Glu Ala Leu Gln Phe Ser Ala
945                 950                 955                 960

Tyr Leu Arg Gln Ser Asn Lys Ile Ser Lys Lys Glu Lys Asp Asp Tyr
                965                 970                 975

Val Asp Tyr Val Ile Asp Leu Leu Glu Met Thr Asp Tyr Ala Asp Ala
                980                 985                 990

Leu Val Gly Val Ala Gly Glu Gly Leu Asn Val Glu Gln Arg Lys Arg
                995                 1000                1005

Leu Thr Ile Gly Val Glu Leu Val Ala Lys Pro Lys Leu Leu Leu
        1010                1015                1020

Phe Leu Asp Glu Pro Ala Ser Gly Leu Asp Ser Gln Thr Ala Trp
        1025                1030                1035

Ser Ile Cys Lys Leu Met Arg Lys Leu Ala Asp His Gly Gln Ala
        1040                1045                1050

Ile Leu Cys Thr Ile His Gln Pro Ser Ala Leu Ile Met Ala Glu
        1055                1060                1065

Phe Asp Arg Leu Leu Phe Leu Gln Lys Gly Gly Arg Thr Ala Tyr
        1070                1075                1080

Phe Gly Glu Leu Gly Glu Asn Cys Gln Thr Met Ile Asn Tyr Phe
        1085                1090                1095

Glu Lys Tyr Gly Ala Asp Pro Cys Pro Lys Glu Ala Asn Pro Ala
        1100                1105                1110

Glu Trp Met Leu Gln Val Val Gly Ala Ala Pro Gly Ser His Ala
        1115                1120                1125

Lys Gln Asp Tyr Phe Glu Val Trp Arg Asn Ser Ser Glu Tyr Gln
        1130                1135                1140

Ala Val Arg Glu Glu Ile Asn Arg Met Glu Ala Glu Leu Ser Lys
        1145                1150                1155

Leu Pro Arg Asp Asn Asp Pro Glu Ala Leu Leu Lys Tyr Ala Ala
        1160                1165                1170

Pro Leu Trp Lys Gln Tyr Leu Leu Val Ser Trp Arg Thr Ile Val
        1175                1180                1185

Gln Asp Trp Arg Ser Pro Gly Tyr Ile Tyr Ser Lys Ile Phe Leu
        1190                1195                1200

Val Val Ser Ala Ala Leu Phe Asn Gly Phe Ser Phe Phe Lys Ala
        1205                1210                1215

Lys Asn Asn Met Gln Gly Leu Gln Asn Gln Met Phe Ser Val Phe
        1220                1225                1230

Met Phe Phe Ile Pro Phe Asn Thr Leu Val Gln Gln Met Leu Pro
        1235                1240                1245

Tyr Phe Val Lys Gln Arg Asp Val Tyr Glu Val Arg Glu Ala Pro
        1250                1255                1260

Ser Arg Thr Phe Ser Trp Phe Ala Phe Ile Ala Gly Gln Ile Thr
        1265                1270                1275

Ser Glu Ile Pro Tyr Gln Val Ala Val Gly Thr Ile Ala Phe Phe
        1280                1285                1290

Cys Trp Tyr Tyr Pro Leu Gly Leu Tyr Asn Asn Ala Thr Pro Thr
        1295                1300                1305

```
Asp Ser Val Asn Pro Arg Gly Val Leu Met Trp Met Leu Val Thr
    1310            1315                1320
Ala Phe Tyr Val Tyr Thr Ala Thr Met Gly Gln Leu Cys Met Ser
    1325            1330                1335
Phe Ser Glu Leu Ala Asp Asn Ala Ala Asn Leu Ala Thr Leu Leu
    1340            1345                1350
Phe Thr Met Cys Leu Asn Phe Cys Gly Val Leu Ala Gly Pro Asp
    1355            1360                1365
Val Leu Pro Gly Phe Trp Ile Phe Met Tyr Arg Cys Asn Pro Phe
    1370            1375                1380
Thr Tyr Leu Val Gln Ala Met Leu Ser Thr Gly Leu Ala Asn Thr
    1385            1390                1395
Phe Val Lys Cys Ala Glu Arg Glu Tyr Val Ser Val Lys Pro Pro
    1400            1405                1410
Asn Gly Glu Ser Cys Ser Thr Tyr Leu Asp Pro Tyr Ile Lys Phe
    1415            1420                1425
Ala Gly Gly Tyr Phe Glu Thr Arg Asn Asp Gly Ser Cys Ala Phe
    1430            1435                1440
Cys Gln Met Ser Ser Thr Asn Thr Phe Leu Lys Ser Val Asn Ser
    1445            1450                1455
Leu Tyr Ser Glu Arg Trp Arg Asn Phe Gly Ile Phe Ile Ala Phe
    1460            1465                1470
Ile Ala Ile Asn Ile Ile Leu Thr Val Ile Phe Tyr Trp Leu Ala
    1475            1480                1485
Arg Val Pro Lys Gly Asn Arg Glu Lys Lys Asn Lys Lys
    1490            1495                1500

<210> SEQ ID NO 53
<211> LENGTH: 4500
<212> TYPE: DNA
<213> ORGANISM: Candida glabrata

<400> SEQUENCE: 53
atgtctcttg caagtgacaa gaaggatgcc gatgtggcgt ctactactac aactgcgcaa      60
gatgatgaca acttgtccac atatcatggt ttcgaccatc atgtgcagga ccaagtcaga     120
cagcttgccc gtacattgac tcaacagagc agtctgcatc aaaagaaaga acacactctg     180
cctgaggaag gtatcaaccc tatctttacc aacactgagg ccgatgacta acccaaga      240
ttggacccta cttccgatga gttctcctct gcagaatggg ttcagaacat gagcaacatt     300
agcaactcag acccggatta ctacaaacca tactcccttg gctgttactg gaaggatttg     360
gtcgcaactg tgaatctgc tgatatcgaa taccaggcca acttcttgaa cggaccatat     420
aaaggtctga aaactgttta taacacggtg gtgccatcca cagcctcttc aaaggacaag     480
aatttcaaga ttttgaagtc tatggaaggt gccgtcaacc caggtgagct gctagttgtg     540
ctaggtagac ctggttcagg gtgtaccact ttgctaaaat ctatctcgtc taatacccac     600
ggtttcaaca tcgccaagga ttctactatc tcctatagcg gtatgactcc aaacgacatc     660
agaaaacact tccgtggtga agttgtctac aacgctgaag ccgatatcca tttaccacac     720
ttgactgttt accaaacttt actgacagtt gcaagattaa agacaccaca aaatcgtctg     780
aaaggaatcg atagagagac ttacgctaga catttaacgg aagtggccat ggccactttt     840
ggtcttttca c atacaagaaa caccaaagtc ggtaacgact tagttagagg tgtttctggt     900
ggtgaacgta agcgtgtctc cattgctgaa gtctctattt gtggttctaa attccaatgt     960
```

```
tgggataacg caacgagagg tttagattct gccaccgcac tggagtttat ccgtgcttta    1020
aaagttcaag ccagtatttc caatgctgct gctactgtgg ctatctacca atgttctcaa    1080
gatgcatacg atctattcga taaagtctgt gtgctttacg atggttatca aatttacttg    1140
ggacctgctg gtaaggctaa agatatttt caaaagatgg ggtacgttag tcctgaaaga    1200
cagactactg ctgacttcct aacagctgtc acttctccat ctgaaagaat aataaaccag    1260
gattacataa atagaggtat ctttgttcct caaactccta aggaaatgtg gaatattgg    1320 agagcctccg aagatcatgc tgacctaatt aaagaaattg acagtaagtt atctgataat    1380
tacgatgcta atcttgcaga aataaaggat gctcatgtcg ctagacagtc taagagagct    1440
agaccatctt ccccatatac cgtaagctat ggtatgcaaa taaatactt attaattcgt    1500 aatttctgga gaatcaaaca gagttcaggt gttacgttat ttatggtcat aggtaactcg    1560
tcgatggcgt ttatattggg ttcaatgttc tacaaggtaa tgaaacataa tactacctcc    1620
acattttatt tcagaggtgc tgccatgttc ttcgctgtct tatttaatgc cttctcatcc    1680
ctattggaaa ttttctcttt attcgaagct agaccaatca ctgaaaaaca tagaacatac    1740
tcgctatacc acccaagtgc tgatgcattt gcctctatcc tttctgaagt tccagctaaa    1800
cttattactg ccgtttgttt caatattatt tactacttct tggtgaattt cagaagaaat    1860
ggtggtgtct tcttcttcta tttcctgatc aacattgttg cagtatttgc catgtctcat    1920
ttatttagat gtgttggttc tgtctcaaag acattatctg ctgcgatggt tcctgcttcc    1980
atgttattgc ttggtttgtc aatgtattcc ggttttgcaa tcccaaggac taagattttg    2040
ggatggtcta atggatctg gtacatcaac ccacttgcat acttatttga atcgttgatg    2100
atcaatgagt ttcatgaccg taaattccca tgttcacaat atatcccatc tggttcagtt    2160
tataataacg ttccagctga ctcaaggatt tgttctagtg ttggtgccat tagaggtaat    2220
gactatgttt tgggtgacga cttcttgaga gagagttact cttacttgca caaacataag    2280
tggcgtggtt ttggtattgg tctggcctat gtgattttct tccttgtttt gtacttaatc    2340
ctttgtgagt acaatgaagg tgccaaacaa aagggtgaaa tcttggtctt cccacaaaat    2400
attgttagaa gaatgaaaaa agaacgtaaa ctgaagaatg ttagctctga caatgatgtt    2460
gaaattggtg atgttagtga tatctccgac aaaaagattc ttgctgattc atctgatgaa    2520
tcggaagaaa gtggtgctaa cattggttta tctcaatctg aagccatctt ccactggaga    2580
aacttgtgtt acgatgttca aattaaaaag gaaactagac gtatcttgaa taatgtggat    2640
ggttgggtta aaccaggtac tttgactgcg ctaatgggtg catcgggtgc tggtaagact    2700
acattattgg attgtttggc ggagagagta acgatgggtg ttattacagg tgaggtttca    2760
gttgatggta agcaaagaga tgactctttt gctagatcta ttggttactg tcaacaacaa    2820
gatttgcact tgaaaacatc gacagttagg gaatcgctaa gattctccgc ttacctacgt    2880
caacctgctg atgtgtctat tgaagaaaag accaatacg ttgaagatgt cattaagatt    2940
ctagaaatgg aacaatatgc agatgctgtt gttggtgttc ctggtgaagg tttaaatgtt    3000
gaacaaagaa agagactgac tattggtgtt gaattggctg ctaaaccaaa acttttggtc    3060
tttttggatg aacctacttc aggtctggat tcacaaacag catggtccat tgtcaactta    3120
atgaaaaaac tagctaatca tggccaagct atttttgtgta caattcacca accttctgct    3180
attttgatgc aagagtttga tagattgctg ttttttgcaac gtggtggtaa gaccgtttac    3240
tttggtgacc taggtgatgg ctgtaagact atgatcgatt attttgaaag ccatggctct    3300
cacaagtgtc caccagatgc taacccagct gaatggatgt tagaagtcgt tggtgctgct    3360
```

```
ccagggtctc atgctaatca ggattaccac gaagtatgga gaaattccga tgagtatcaa    3420
aaggttcagg aagaattgga gtggatgtcc aacgagcttc caaagaaaaa tactaataac    3480
tctgagacag tccataaaga atttgctact ggtgttcttt accaatgtaa gttggtttcc    3540
cctcgtctgt tccaacaata ctggagatct ccagattacc tatggtcaaa gttcttcttg    3600
actattttca acaatatctt tattggtttc acattcttca aagctgatag gtcattgcaa    3660
ggtttgcaaa accaaatgtt agctgttttt atgtttacag tgatcttcaa cccattgcta    3720
cagcagtatt tgccatcatt tgttcaacaa agagacttat acgaagcaag agaaagacct    3780
tccagaacat tttcatggaa ggctttcatt gtttctcaaa tccttgttga atcccatgg     3840 aatatcctag ctggtactgt cgcttttgtg atttactatt atgctattgg gttctactcc    3900
aatgcttctg tagcacatca actacacgaa cgtggtgctt tgttctggtt gttttcgtgc    3960
gcattctatg tgtacattgg atctcttgct ctattttgta tttcctttaa ccaggtggca    4020
gaagcagcag caaacatggc atccttaatg ttcactctat cgctatcttt ctgtggtgtt    4080
ctagttactc caaatggtat gccaagattc tggattttca tgtacagagt atcgccattg    4140
acttatctga ttgatggtat gctttctact ggtgttgcta atgtcgccat taagtgttct    4200
aactacgagt tactgcggtt ttctcctgct gcaaacctga cttgtggtga gtacttggga    4260
ccctacctac aaaccgtgaa gactggctac attgttgacc catctgctac agacacatgt    4320
gaattatgtc atactctca taccaatgac ttcttgagtt ctgttagttc caaatattct     4380
cgtagatgga gaaattgggg tattttcatc tgttacattg ctttcaacta tatcgctggt    4440
attttcttgt actggttggc cagagttcca aagaaatctg gtaaacttgc caagaaataa    4500
```

<210> SEQ ID NO 54
<211> LENGTH: 1499
<212> TYPE: PRT
<213> ORGANISM: Candida glabrata

<400> SEQUENCE: 54

```
Met Ser Leu Ala Ser Asp Lys Lys Asp Ala Asp Val Ala Ser Thr Thr
1               5                   10                  15

Thr Thr Ala Gln Asp Asp Asp Asn Leu Ser Thr Tyr His Gly Phe Asp
            20                  25                  30

His His Val Gln Asp Gln Val Arg Gln Leu Ala Arg Thr Leu Thr Gln
        35                  40                  45

Gln Ser Ser Leu His Gln Lys Lys Glu His Thr Leu Pro Glu Glu Gly
    50                  55                  60

Ile Asn Pro Ile Phe Thr Asn Thr Glu Ala Asp Asp Tyr Asn Pro Arg
65                  70                  75                  80

Leu Asp Pro Thr Ser Asp Glu Phe Ser Ser Ala Glu Trp Val Gln Asn
                85                  90                  95

Met Ser Asn Ile Ser Asn Ser Asp Pro Asp Tyr Tyr Lys Pro Tyr Ser
            100                 105                 110

Leu Gly Cys Tyr Trp Lys Asp Leu Val Ala Thr Gly Glu Ser Ala Asp
        115                 120                 125

Ile Glu Tyr Gln Ala Asn Phe Leu Asn Gly Pro Tyr Lys Gly Leu Lys
    130                 135                 140

Thr Val Tyr Asn Thr Val Val Pro Ser Thr Ala Ser Ser Lys Asp Lys
145                 150                 155                 160

Asn Phe Lys Ile Leu Lys Ser Met Glu Gly Ala Val Asn Pro Gly Glu
                165                 170                 175

Leu Leu Val Val Leu Gly Arg Pro Gly Ser Gly Cys Thr Thr Leu Leu
```

```
                    180                 185                 190
Lys Ser Ile Ser Ser Asn Thr His Gly Phe Asn Ile Ala Lys Asp Ser
                195                 200                 205

Thr Ile Ser Tyr Ser Gly Met Thr Pro Asn Asp Ile Arg Lys His Phe
            210                 215                 220

Arg Gly Glu Val Val Tyr Asn Ala Glu Ala Asp Ile His Leu Pro His
225                 230                 235                 240

Leu Thr Val Tyr Gln Thr Leu Leu Thr Val Ala Arg Leu Lys Thr Pro
                245                 250                 255

Gln Asn Arg Leu Lys Gly Ile Asp Arg Glu Thr Tyr Ala Arg His Leu
            260                 265                 270

Thr Glu Val Ala Met Ala Thr Phe Gly Leu Ser His Thr Arg Asn Thr
                275                 280                 285

Lys Val Gly Asn Asp Leu Val Arg Gly Val Ser Gly Gly Glu Arg Lys
            290                 295                 300

Arg Val Ser Ile Ala Glu Val Ser Ile Cys Gly Ser Lys Phe Gln Cys
305                 310                 315                 320

Trp Asp Asn Ala Thr Arg Gly Leu Asp Ser Ala Thr Ala Leu Glu Phe
                325                 330                 335

Ile Arg Ala Leu Lys Val Gln Ala Ser Ile Ser Asn Ala Ala Ala Thr
            340                 345                 350

Val Ala Ile Tyr Gln Cys Ser Gln Asp Ala Tyr Asp Leu Phe Asp Lys
                355                 360                 365

Val Cys Val Leu Tyr Asp Gly Tyr Gln Ile Tyr Leu Gly Pro Ala Gly
            370                 375                 380

Lys Ala Lys Arg Tyr Phe Gln Lys Met Gly Tyr Val Ser Pro Glu Arg
385                 390                 395                 400

Gln Thr Thr Ala Asp Phe Leu Thr Ala Val Thr Ser Pro Ser Glu Arg
                405                 410                 415

Ile Ile Asn Gln Asp Tyr Ile Asn Arg Gly Ile Phe Val Pro Gln Thr
            420                 425                 430

Pro Lys Glu Met Trp Glu Tyr Trp Arg Ala Ser Glu Asp His Ala Asp
                435                 440                 445

Leu Ile Lys Glu Ile Asp Ser Lys Leu Ser Asp Asn Tyr Asp Ala Asn
            450                 455                 460

Leu Ala Glu Ile Lys Asp Ala His Val Ala Arg Gln Ser Lys Arg Ala
465                 470                 475                 480

Arg Pro Ser Ser Pro Tyr Thr Val Ser Tyr Gly Met Gln Ile Lys Tyr
                485                 490                 495

Leu Leu Ile Arg Asn Phe Trp Arg Ile Lys Gln Ser Ser Gly Val Thr
            500                 505                 510

Leu Phe Met Val Ile Gly Asn Ser Ser Met Ala Phe Ile Leu Gly Ser
                515                 520                 525

Met Phe Tyr Lys Val Met Lys His Asn Thr Thr Ser Thr Phe Tyr Phe
            530                 535                 540

Arg Gly Ala Ala Met Phe Phe Ala Val Leu Phe Asn Ala Phe Ser Ser
545                 550                 555                 560

Leu Leu Glu Ile Phe Ser Leu Phe Glu Ala Arg Pro Ile Thr Glu Lys
                565                 570                 575

His Arg Thr Tyr Ser Leu Tyr His Pro Ser Ala Asp Ala Phe Ala Ser
            580                 585                 590

Ile Leu Ser Glu Val Pro Ala Lys Leu Ile Thr Ala Val Cys Phe Asn
                595                 600                 605
```

-continued

Ile Ile Tyr Tyr Phe Leu Val Asn Phe Arg Arg Asn Gly Gly Val Phe
610                 615                 620

Phe Phe Tyr Phe Leu Ile Asn Ile Val Ala Val Phe Ala Met Ser His
625                 630                 635                 640

Leu Phe Arg Cys Val Gly Ser Val Ser Lys Thr Leu Ser Ala Ala Met
            645                 650                 655

Val Pro Ala Ser Met Leu Leu Gly Leu Ser Met Tyr Ser Gly Phe
            660                 665                 670

Ala Ile Pro Arg Thr Lys Ile Leu Gly Trp Ser Lys Trp Ile Trp Tyr
            675                 680                 685

Ile Asn Pro Leu Ala Tyr Leu Phe Glu Ser Leu Met Ile Asn Glu Phe
690                 695                 700

His Asp Arg Lys Phe Pro Cys Ser Gln Tyr Ile Pro Ser Gly Ser Val
705                 710                 715                 720

Tyr Asn Asn Val Pro Ala Asp Ser Arg Ile Cys Ser Ser Val Gly Ala
            725                 730                 735

Ile Arg Gly Asn Asp Tyr Val Leu Gly Asp Asp Phe Leu Arg Glu Ser
            740                 745                 750

Tyr Ser Tyr Leu His Lys His Lys Trp Arg Gly Phe Gly Ile Gly Leu
            755                 760                 765

Ala Tyr Val Ile Phe Phe Leu Val Leu Tyr Leu Ile Leu Cys Glu Tyr
770                 775                 780

Asn Glu Gly Ala Lys Gln Lys Gly Glu Ile Leu Val Phe Pro Gln Asn
785                 790                 795                 800

Ile Val Arg Arg Met Lys Lys Glu Arg Lys Leu Lys Asn Val Ser Ser
            805                 810                 815

Asp Asn Asp Val Glu Ile Gly Asp Val Ser Asp Ile Ser Asp Lys Lys
            820                 825                 830

Ile Leu Ala Asp Ser Ser Asp Glu Ser Glu Glu Ser Gly Ala Asn Ile
            835                 840                 845

Gly Leu Ser Gln Ser Glu Ala Ile Phe His Trp Arg Asn Leu Cys Tyr
850                 855                 860

Asp Val Gln Ile Lys Lys Glu Thr Arg Arg Ile Leu Asn Asn Val Asp
865                 870                 875                 880

Gly Trp Val Lys Pro Gly Thr Leu Thr Ala Leu Met Gly Ala Ser Gly
            885                 890                 895

Ala Gly Lys Thr Thr Leu Leu Asp Cys Leu Ala Glu Arg Val Thr Met
            900                 905                 910

Gly Val Ile Thr Gly Glu Val Ser Val Asp Gly Lys Gln Arg Asp Asp
            915                 920                 925

Ser Phe Ala Arg Ser Ile Gly Tyr Cys Gln Gln Gln Asp Leu His Leu
930                 935                 940

Lys Thr Ser Thr Val Arg Glu Ser Leu Arg Phe Ser Ala Tyr Leu Arg
945                 950                 955                 960

Gln Pro Ala Asp Val Ser Ile Glu Glu Lys Asn Gln Tyr Val Glu Asp
            965                 970                 975

Val Ile Lys Ile Leu Glu Met Glu Gln Tyr Ala Asp Ala Val Val Gly
            980                 985                 990

Val Pro Gly Glu Gly Leu Asn Val Glu Gln Arg Lys Arg Leu Thr Ile
            995                 1000                1005

Gly Val Glu Leu Ala Ala Lys Pro Lys Leu Leu Val Phe Leu Asp
    1010            1015               1020

Glu Pro Thr Ser Gly Leu Asp Ser Gln Thr Ala Trp Ser Ile Cys
    1025            1030               1035

Gln Leu Met Lys Lys Leu Ala Asn His Gly Gln Ala Ile Leu Cys
    1040                1045                1050

Thr Ile His Gln Pro Ser Ala Ile Leu Met Gln Glu Phe Asp Arg
    1055                1060                1065

Leu Leu Phe Leu Gln Arg Gly Gly Lys Thr Val Tyr Phe Gly Asp
    1070                1075                1080

Leu Gly Asp Gly Cys Lys Thr Met Ile Asp Tyr Phe Glu Ser His
    1085                1090                1095

Gly Ser His Lys Cys Pro Pro Asp Ala Asn Pro Ala Glu Trp Met
    1100                1105                1110

Leu Glu Val Val Gly Ala Ala Pro Gly Ser His Ala Asn Gln Asp
    1115                1120                1125

Tyr His Glu Val Trp Arg Asn Ser Asp Glu Tyr Gln Lys Val Gln
    1130                1135                1140

Glu Glu Leu Glu Trp Met Ser Asn Glu Leu Pro Lys Lys Asn Thr
    1145                1150                1155

Asn Asn Ser Glu Thr Val His Lys Glu Phe Ala Thr Gly Val Leu
    1160                1165                1170

Tyr Gln Cys Lys Leu Val Ser Pro Arg Leu Phe Gln Gln Tyr Trp
    1175                1180                1185

Arg Ser Pro Asp Tyr Leu Trp Ser Lys Phe Phe Leu Thr Ile Phe
    1190                1195                1200

Asn Asn Ile Phe Ile Gly Phe Thr Phe Phe Lys Ala Asp Arg Ser
    1205                1210                1215

Leu Gln Gly Leu Gln Asn Gln Met Leu Ala Val Phe Met Phe Thr
    1220                1225                1230

Val Ile Phe Asn Pro Leu Leu Gln Gln Tyr Leu Pro Ser Phe Val
    1235                1240                1245

Gln Gln Arg Asp Leu Tyr Glu Ala Arg Glu Arg Pro Ser Arg Thr
    1250                1255                1260

Phe Ser Trp Lys Ala Phe Ile Val Ser Gln Ile Leu Val Glu Ile
    1265                1270                1275

Pro Trp Asn Ile Leu Ala Gly Thr Val Ala Phe Val Ile Tyr Tyr
    1280                1285                1290

Tyr Ala Ile Gly Phe Tyr Ser Asn Ala Ser Val Ala His Gln Leu
    1295                1300                1305

His Glu Arg Gly Ala Leu Phe Trp Leu Phe Ser Cys Ala Phe Tyr
    1310                1315                1320

Val Tyr Ile Gly Ser Leu Ala Leu Phe Cys Ile Ser Phe Asn Gln
    1325                1330                1335

Val Ala Glu Ala Ala Ala Asn Met Ala Ser Leu Met Phe Thr Leu
    1340                1345                1350

Ser Leu Ser Phe Cys Gly Val Leu Val Thr Pro Asn Gly Met Pro
    1355                1360                1365

Arg Phe Trp Ile Phe Met Tyr Arg Val Ser Pro Leu Thr Tyr Leu
    1370                1375                1380

Ile Asp Gly Met Leu Ser Thr Gly Val Ala Asn Val Ala Ile Lys
    1385                1390                1395

Cys Ser Asn Tyr Glu Leu Leu Arg Phe Ser Pro Ala Ala Asn Leu
    1400                1405                1410

Thr Cys Gly Glu Tyr Leu Gly Pro Tyr Leu Gln Thr Val Lys Thr
    1415                1420                1425

Gly Tyr Ile Val Asp Pro Ser Ala Thr Asp Thr Cys Glu Leu Cys

Pro Tyr Ser His Thr Asn Asp Phe Leu Ser Ser Val Ser Ser Lys
1445                1450                1455

Tyr Ser Arg Arg Trp Arg Asn Trp Gly Ile Phe Ile Cys Tyr Ile
1460                1465                1470

Ala Phe Asn Tyr Ile Ala Gly Ile Phe Leu Tyr Trp Leu Ala Arg
1475                1480                1485

Val Pro Lys Lys Ser Gly Lys Leu Ala Lys Lys
1490                1495

<210> SEQ ID NO 55
<211> LENGTH: 4518
<212> TYPE: DNA
<213> ORGANISM: Pichia stipitis

<400> SEQUENCE: 55

| | | | | | |
|---|---|---|---|---|---|
| atgtccgatg | cctctatagg | gaaagaatcc | caggaacaga | agaagaacat | cccatccaac | 60 |
| tcgtccaccg | tgtcagacac | atcttccatc | aacgaatacc | agggtttcaa | cagatccact | 120 |
| gctgctgatg | tgcaagaact | cgccagaaca | atcacccatg | agtcatacac | ctttgaaaac | 180 |
| gaccaggcct | cctccatcgg | tcttatcaag | tacttgtcgc | acatgtcgca | agtgccaggt | 240 |
| gtcaacccat | atgttgaaga | agagactaat | ccggaattag | accccaacag | cgagtcgttc | 300 |
| aatgccaagt | tctgggtcaa | gaatttgagg | aagttgtacg | actccgatcc | cgagtactac | 360 |
| cagccttcca | gttgggtat | tgcctaccgt | gacttgagag | cctatggtgt | cgctgctgac | 420 |
| tccgactacc | aacctactgt | gaccaatgcc | atctggaaat | tcgctgtaga | aacttctaga | 480 |
| acgttccaaa | aagaagatcc | ttcgcgttac | ttcgacattt | tgaagcctat | ggatgccata | 540 |
| atgaagcctg | gtgaagtcac | cgtcgtcttg | ggaagacctg | gttctggatg | ttcgactttg | 600 |
| ttgaagacca | tttctgccca | tacctacggt | ttccatgttg | gcgaagaatc | gagaatcacc | 660 |
| tacgacgggt | tatcgcctca | agatatcgtt | gacaaccacc | gtggtgatgt | cgtatattcg | 720 |
| gctgaaactg | atgtccattt | ccctcactta | actgtaggag | acaccttgga | gttcgcagcc | 780 |
| agattgagaa | ctccccagaa | cagaggtctc | ggcgtcgaca | gagaaaccta | cgctaagcac | 840 |
| atggccagtg | tatacatggc | cacatacggg | ttatctcata | ccagaaatac | caacgtcggt | 900 |
| aatgacttcg | ttagaggtgt | ttctggtggt | gaaagaaaaa | gagtctctat | tgccgaagta | 960 |
| tcgttgtcag | gtgccaactt | gcaatgttgg | gataacgcta | ccagaggttt | ggatgccgcc | 1020 |
| actgctttgg | aattcatcag | agccttgaaa | acttcggcca | ctattttaga | agccacacct | 1080 |
| ttgattgcta | tctaccagtg | ttcccaagat | gcctacgatt | tattcgataa | cgtggtattg | 1140 |
| ttgtacgagg | gctaccagat | cttctttggt | aaagctgaag | atgctaagac | attcttcgtc | 1200 |
| aacatgggtt | acgaatgtcc | acaaagacag | actactgccg | attatttgac | ttctttgact | 1260 |
| aaccctgctg | aaagaatcgt | cattccaggc | tacgagaact | cggtacctag | aacagccaag | 1320 |
| gagttcgaag | cctactggaa | gagctctcca | gagtacaaat | ccttggttga | agaaattgag | 1380 |
| cagcattttc | aagatgttga | aaccaataac | gtcaaacaat | catacctcga | ttctcacgtt | 1440 |
| gccaaacagt | cgaaacacct | ctcgccaaag | tcgccataca | ccgtttcgtt | cttcatgcaa | 1500 |
| gtcagataca | tcatgggaag | aaactttttta | agacttaagg | gtgatccttc | cattgctatt | 1560 |
| ttctcagtct | ttggtcaagg | tgttatgggt | ttgatcttgt | cttctgtgtt | ctacaacttg | 1620 |
| agtcaaacca | ctgagtcctt | ttactacaga | ggtgctgcta | tgttctttgc | tgtgttattc | 1680 |
| aatgcgtttg | cctctctttt | ggaaatcatg | tctcttttttg | aagccagacc | tatcgttgaa | 1740 |

```
aagcataaga aatacgctct ttatcgtcct tctgccgatg ctctagctgg tatcattaca    1800
gaattaccta ctaagttgtg tatgtctgtt tcgttcaact tcgtcttcta tttcatggtc    1860
aacttcagaa gaacacctgg taacttcttc ttctattggt tgatggctgg ttggtgtacg    1920
ttggtgatgt cacacttgtt cagatcattg ggtgctgtgt ctacgtcttt ggctggtgcc    1980
atgactcctg ctactgtttt gttacttgcc atggttattt acactggttt cgtcattcct    2040
actccaaaga tgttgggttg gtccagatgg atcaactata ttaatcccgt gggttatgtg    2100
ttcgagtcgt tgatggtcaa cgagttccac gaacgtgact ttgaatgtgc cacttttgtt    2160
ccaacgggtc ctaactatgt gaacgtacct gaagatgcca gagtctgcaa tactgttggt    2220
gccagacccg gctcgaacat cgttctgggt accgactacc ttgctctttc gtaccagtac    2280
taccactctc acaagtggag aaatctcggt atcactattg cctttgctgt tttcttctta    2340
tttgtctaca ttgcgttgac tgagttcaac aagggtgcca tgcaaaaggg tgaaattacc    2400
ttgttcctta gaggctcatt gaagaagcac aagaaggaag ccagaaaggt aaggctaac     2460 gtggctgaca ttgaaaccgc tgacacgaac gaaaagattg gtttcagtga cgaattggat    2520
gccactaaga caaatcgag ttccaactct ggcgataact ccttgccttc ttctaaagac     2580
attttccatt ggaaggactt gacctatcaa gtgaaaatca gagtgagga gcgtgttatc     2640 ttaaaccact gtgacggttg ggttaaacca ggccaattga ctgctttgat gggttcttct    2700
ggtgcaggta agactacgct tttgaactgt ttgtctgaaa gagtcactac tggtgttatc    2760
actgatggtg tcagaatggt taatggtcac tcttttggatt cttcttcca gagatccatt    2820 ggttatgtcc agcaacagga tttgcatctt cctacctcga ctgtccgtga agccttgaga    2880
ttctccgcct acttgagaca acccaattcg gttttcaaaga aggaaaagga agaatacgtt    2940
gaatacatca tcgacttgtt ggaaatgtac gactacgctg acgctttggt tggtgttgcc    3000
ggtgaaggtt tgaatgttga acagagaaag agattgacta tcggtgttga attggtggcc    3060
aaacccaaat tgttgttgtt tttggatgag cctacttctg gtttggattc gcaaactgcc    3120
tggtccattt gtaagttgat gagaaagttg gcagaccatg gtcaagcaat tttgtgtact    3180
atccatcagc cctctgctct tttgttgaag gaatttgacc gtttgttgtt cttgcaaagt    3240
ggtggtcaga ctgtgtactt tggagacttg ggtgaaaact gttctacctt gattgaatac    3300
ttcgagaaat acggttctca cccatgtcct aaggaagcta accctgccga atggatgttg    3360
gaagttgtcg gtgctgctcc tggttcccac gctaatcagg actaccatga agtctggaag    3420
aactctaccg aatacaagga cgtgcacgag gagttggcta aaatgaaag agaattggtt     3480 ttgcttccaa aggatgactc accagactcg cacttgaaat acgctgctcc aatctggaag    3540
caatacttga tcgtttcggc tagagtcatc caacaaaact ggagatcgcc tggctacatc    3600
tactccaagt tgttcttggt attgtcttct gctctttca acggtttctc tttttttcaag    3660 gctgacagat cgatgcaagg tttgcaaaat caaatgtttg ccatctttat gttcttcatt    3720
cctttcaaca ccttggtgca acagatgttg ccttactttg ttagacagag agatgtctac    3780
gaagtgagag aagctccttc cagaacattc agttggttttg cctttattac tggccagatc    3840
actgctgaaa tcccatacca cgttgctgtc ggtactttat cattcttctg ctggtactac    3900
cctgttggac tctaccagaa tgcagtccca accgacctgg ttaactctcg tggtgtcctc    3960
atgtggttgt tacttacgag tttctttgtc tactccggta ccatgggtca gttgtgtatg    4020
gccttcaacg aattggccga caacgctgct aacttggcta cattgttgtt caccatgtgt    4080
ttgaacttct gtggtgtctt agctggacct gatgtgttgc ccggcttctg gattttcatg    4140
```

```
tacagagcca accccttcac atacttgatc caggctattt tgtctactgg tttggccaac    4200
acttcagtag tctgttctcc aaatgagttg gttcctttga accctcctaa tggtcaaact    4260
tgtttggaat acatgcaacc ctacatcgac gctactggag gttacttagt tgacgagaat    4320
gccacatcag gatgtcaatt ctgtcaaatg gcaaaaacca acgatttctt gaagtctgtc    4380
aacgccttgt actctgaaag atggagaaac ttcggtattt tcattgcctt cattgccatc    4440
aacatcatct tgactgttgt attctactat tgggccagag ttccaaaggg taccagacaa    4500
aagaagtcgt ccaagtag                                                 4518

<210> SEQ ID NO 56
<211> LENGTH: 1505
<212> TYPE: PRT
<213> ORGANISM: Pichia stipitis

<400> SEQUENCE: 56
```

Met Ser Asp Ala Ser Ile Gly Lys Glu Ser Gln Glu Gln Lys Lys Asn
1               5                   10                  15

Ile Pro Ser Asn Ser Ser Thr Val Ser Asp Thr Ser Ser Ile Asn Glu
            20                  25                  30

Tyr Gln Gly Phe Asn Arg Ser Thr Ala Ala Asp Val Gln Glu Leu Ala
        35                  40                  45

Arg Thr Ile Thr His Glu Ser Tyr Thr Phe Glu Asn Asp Gln Ala Ser
    50                  55                  60

Ser Ile Gly Leu Ile Lys Tyr Leu Ser His Met Ser Gln Val Pro Gly
65                  70                  75                  80

Val Asn Pro Tyr Val Glu Glu Thr Asn Pro Glu Leu Asp Pro Asn
                85                  90                  95

Ser Glu Ser Phe Asn Ala Lys Phe Trp Val Lys Asn Leu Arg Lys Leu
            100                 105                 110

Tyr Asp Ser Asp Pro Glu Tyr Tyr Gln Pro Ser Lys Leu Gly Ile Ala
        115                 120                 125

Tyr Arg Asp Leu Arg Ala Tyr Gly Val Ala Ala Asp Ser Asp Tyr Gln
    130                 135                 140

Pro Thr Val Thr Asn Ala Ile Trp Lys Phe Ala Val Glu Thr Ser Arg
145                 150                 155                 160

Thr Phe Gln Lys Glu Asp Pro Ser Arg Tyr Phe Asp Ile Leu Lys Pro
                165                 170                 175

Met Asp Ala Ile Met Lys Pro Gly Glu Val Thr Val Leu Gly Arg
        180                 185                 190

Pro Gly Ser Gly Cys Ser Thr Leu Leu Lys Thr Ile Ser Ala His Thr
    195                 200                 205

Tyr Gly Phe His Val Gly Glu Glu Ser Arg Ile Thr Tyr Asp Gly Leu
    210                 215                 220

Ser Pro Gln Asp Ile Val Asp Asn His Arg Gly Asp Val Val Tyr Ser
225                 230                 235                 240

Ala Glu Thr Asp Val His Phe Pro His Leu Thr Val Gly Asp Thr Leu
                245                 250                 255

Glu Phe Ala Ala Arg Leu Arg Thr Pro Gln Asn Arg Gly Leu Gly Val
        260                 265                 270

Asp Arg Glu Thr Tyr Ala Lys His Met Ala Ser Val Tyr Met Ala Thr
    275                 280                 285

Tyr Gly Leu Ser His Thr Arg Asn Thr Asn Val Gly Asn Asp Phe Val
    290                 295                 300

Arg Gly Val Ser Gly Gly Glu Arg Lys Arg Val Ser Ile Ala Glu Val

```
                305                 310                 315                 320
        Ser Leu Ser Gly Ala Asn Leu Gln Cys Trp Asp Asn Ala Thr Arg Gly
                        325                 330                 335

Leu Asp Ala Ala Thr Ala Leu Glu Phe Ile Arg Ala Leu Lys Thr Ser
                        340                 345                 350

Ala Thr Ile Leu Glu Ala Thr Pro Leu Ile Ala Ile Tyr Gln Cys Ser
                        355                 360                 365

Gln Asp Ala Tyr Asp Leu Phe Asp Asn Val Val Leu Tyr Glu Gly
                370                 375                 380

Tyr Gln Ile Phe Phe Gly Lys Ala Glu Asp Ala Lys Thr Phe Phe Val
        385                 390                 395                 400

Asn Met Gly Tyr Glu Cys Pro Gln Arg Gln Thr Thr Ala Asp Tyr Leu
                        405                 410                 415

Thr Ser Leu Thr Asn Pro Ala Glu Arg Ile Val Ile Pro Gly Tyr Glu
                        420                 425                 430

Asn Ser Val Pro Arg Thr Ala Lys Glu Phe Glu Ala Tyr Trp Lys Ser
                        435                 440                 445

Ser Pro Glu Tyr Lys Ser Leu Val Glu Glu Ile Glu Gln His Phe Gln
                450                 455                 460

Asp Val Glu Thr Asn Asn Val Lys Gln Ser Tyr Leu Asp Ser His Val
        465                 470                 475                 480

Ala Lys Gln Ser Lys His Leu Ser Pro Lys Ser Pro Tyr Thr Val Ser
                        485                 490                 495

Phe Phe Met Gln Val Arg Tyr Ile Met Gly Arg Asn Phe Leu Arg Leu
                        500                 505                 510

Lys Gly Asp Pro Ser Ile Ala Ile Phe Ser Val Phe Gly Gln Gly Val
                        515                 520                 525

Met Gly Leu Ile Leu Ser Ser Val Phe Tyr Asn Leu Ser Gln Thr Thr
                        530                 535                 540

Glu Ser Phe Tyr Tyr Arg Gly Ala Ala Met Phe Phe Ala Val Leu Phe
        545                 550                 555                 560

Asn Ala Phe Ala Ser Leu Leu Glu Ile Met Ser Leu Phe Glu Ala Arg
                        565                 570                 575

Pro Ile Val Glu Lys His Lys Lys Tyr Ala Leu Tyr Arg Pro Ser Ala
                        580                 585                 590

Asp Ala Leu Ala Gly Ile Ile Thr Glu Leu Pro Thr Lys Leu Cys Met
                        595                 600                 605

Ser Val Ser Phe Asn Phe Val Phe Tyr Phe Met Val Asn Phe Arg Arg
                        610                 615                 620

Thr Pro Gly Asn Phe Phe Tyr Trp Leu Met Ala Gly Trp Cys Thr
        625                 630                 635                 640

Leu Val Met Ser His Leu Phe Arg Ser Leu Gly Ala Val Ser Thr Ser
                        645                 650                 655

Leu Ala Gly Ala Met Thr Pro Ala Thr Val Leu Leu Ala Met Val
                        660                 665                 670

Ile Tyr Thr Gly Phe Val Ile Pro Thr Pro Lys Met Leu Gly Trp Ser
                        675                 680                 685

Arg Trp Ile Asn Tyr Ile Asn Pro Val Gly Tyr Val Phe Glu Ser Leu
                        690                 695                 700

Met Val Asn Glu Phe His Glu Arg Asp Phe Glu Cys Ala Thr Phe Val
        705                 710                 715                 720

Pro Thr Gly Pro Asn Tyr Val Asn Val Pro Glu Asp Ala Arg Val Cys
                        725                 730                 735
```

-continued

Asn Thr Val Gly Ala Arg Pro Gly Ser Asn Ile Val Ser Gly Thr Asp
             740                 745                 750

Tyr Leu Ala Leu Ser Tyr Gln Tyr Tyr His Ser His Lys Trp Arg Asn
             755                 760                 765

Leu Gly Ile Thr Ile Ala Phe Ala Val Phe Leu Phe Val Tyr Ile
         770                 775                 780

Ala Leu Thr Glu Phe Asn Lys Gly Ala Met Gln Lys Gly Glu Ile Thr
785                 790                 795                 800

Leu Phe Leu Arg Gly Ser Leu Lys Lys His Lys Lys Glu Ala Lys Lys
                 805                 810                 815

Gly Lys Ala Asn Val Ala Asp Ile Glu Thr Ala Asp Thr Asn Glu Lys
             820                 825                 830

Ile Gly Phe Ser Asp Glu Leu Asp Ala Thr Lys Asn Lys Ser Ser Ser
         835                 840                 845

Asn Ser Gly Asp Asn Ser Leu Pro Ser Ser Lys Asp Ile Phe His Trp
850                 855                 860

Lys Asp Leu Thr Tyr Gln Val Lys Ile Lys Ser Glu Glu Arg Val Ile
865                 870                 875                 880

Leu Asn His Cys Asp Gly Trp Val Lys Pro Gly Gln Leu Thr Ala Leu
                 885                 890                 895

Met Gly Ser Ser Gly Ala Gly Lys Thr Thr Leu Leu Asn Cys Leu Ser
             900                 905                 910

Glu Arg Val Thr Thr Gly Val Ile Thr Asp Gly Val Arg Met Val Asn
         915                 920                 925

Gly His Ser Leu Asp Ser Ser Phe Gln Arg Ser Ile Gly Tyr Val Gln
     930                 935                 940

Gln Gln Asp Leu His Leu Pro Thr Ser Thr Val Arg Glu Ala Leu Arg
945                 950                 955                 960

Phe Ser Ala Tyr Leu Arg Gln Pro Asn Ser Val Ser Lys Lys Glu Lys
                 965                 970                 975

Glu Glu Tyr Val Glu Tyr Ile Ile Asp Leu Leu Glu Met Tyr Asp Tyr
             980                 985                 990

Ala Asp Ala Leu Val Gly Val Ala  Gly Glu Gly Leu Asn  Val Glu Gln
         995                 1000                1005

Arg Lys Arg Leu Thr Ile Gly  Val Glu Leu Val Ala  Lys Pro Lys
     1010                1015                1020

Leu Leu Leu Phe Leu Asp Glu  Pro Thr Ser Gly Leu  Asp Ser Gln
     1025                1030                1035

Thr Ala Trp Ser Ile Cys Lys  Leu Met Arg Lys Leu  Ala Asp His
     1040                1045                1050

Gly Gln Ala Ile Leu Cys Thr  Ile His Gln Pro Ser  Ala Leu Leu
     1055                1060                1065

Leu Lys Glu Phe Asp Arg Leu  Leu Phe Leu Gln Ser  Gly Gly Gln
     1070                1075                1080

Thr Val Tyr Phe Gly Asp Leu  Gly Glu Asn Cys Ser  Thr Leu Ile
     1085                1090                1095

Glu Tyr Phe Glu Lys Tyr Gly  Ser His Pro Cys Pro  Lys Glu Ala
     1100                1105                1110

Asn Pro Ala Glu Trp Met Leu  Glu Val Val Gly Ala  Ala Pro Gly
     1115                1120                1125

Ser His Ala Asn Gln Asp Tyr  His Glu Val Trp Lys  Asn Ser Thr
     1130                1135                1140

Glu Tyr Lys Asp Val His Glu  Glu Leu Ala Lys Met  Glu Arg Glu
     1145                1150                1155

Leu Val Leu Leu Pro Lys Asp Asp Ser Pro Asp Ser His Leu Lys
    1160            1165            1170

Tyr Ala Ala Pro Ile Trp Lys Gln Tyr Leu Ile Val Ser Ala Arg
    1175            1180            1185

Val Ile Gln Gln Asn Trp Arg Ser Pro Gly Tyr Ile Tyr Ser Lys
    1190            1195            1200

Leu Phe Leu Val Leu Ser Ser Ala Leu Phe Asn Gly Phe Ser Phe
    1205            1210            1215

Phe Lys Ala Asp Arg Ser Met Gln Gly Leu Gln Asn Gln Met Phe
    1220            1225            1230

Ala Ile Phe Met Phe Phe Ile Pro Phe Asn Thr Leu Val Gln Gln
    1235            1240            1245

Met Leu Pro Tyr Phe Val Arg Gln Arg Asp Val Tyr Glu Val Arg
    1250            1255            1260

Glu Ala Pro Ser Arg Thr Phe Ser Trp Phe Ala Phe Ile Thr Gly
    1265            1270            1275

Gln Ile Thr Ala Glu Ile Pro Tyr His Val Ala Val Gly Thr Leu
    1280            1285            1290

Ser Phe Phe Cys Trp Tyr Tyr Pro Val Gly Leu Tyr Gln Asn Ala
    1295            1300            1305

Val Pro Thr Asp Ser Val Asn Ser Arg Gly Val Leu Met Trp Leu
    1310            1315            1320

Leu Leu Thr Ser Phe Phe Val Tyr Ser Gly Thr Met Gly Gln Leu
    1325            1330            1335

Cys Met Ala Phe Asn Glu Leu Ala Asp Asn Ala Ala Asn Leu Ala
    1340            1345            1350

Thr Leu Leu Phe Thr Met Cys Leu Asn Phe Cys Gly Val Leu Ala
    1355            1360            1365

Gly Pro Asp Val Leu Pro Gly Phe Trp Ile Phe Met Tyr Arg Ala
    1370            1375            1380

Asn Pro Phe Thr Tyr Leu Ile Gln Ala Ile Leu Ser Thr Gly Leu
    1385            1390            1395

Ala Asn Thr Ser Val Val Cys Ser Pro Asn Glu Leu Val Pro Leu
    1400            1405            1410

Asn Pro Pro Asn Gly Gln Thr Cys Leu Glu Tyr Met Gln Pro Tyr
    1415            1420            1425

Ile Asp Ala Thr Gly Gly Tyr Leu Val Asp Glu Asn Ala Thr Ser
    1430            1435            1440

Gly Cys Gln Phe Cys Gln Met Ala Lys Thr Asn Asp Phe Leu Lys
    1445            1450            1455

Ser Val Asn Ala Leu Tyr Ser Glu Arg Trp Arg Asn Phe Gly Ile
    1460            1465            1470

Phe Ile Ala Phe Ile Ala Ile Asn Ile Ile Leu Thr Val Val Phe
    1475            1480            1485

Tyr Tyr Trp Ala Arg Val Pro Lys Gly Thr Arg Gln Lys Lys Ser
    1490            1495            1500

Ser Lys
    1505

<210> SEQ ID NO 57
<211> LENGTH: 4506
<212> TYPE: DNA
<213> ORGANISM: Debaryomyces hansenii

<400> SEQUENCE: 57

```
atgtcaagta catctaattc agtagaacat aaatccaagt ttgaggattc gaactcagta      60
actgagttcg ttccctctgc ggaccaaagt tctgtacctc aatacgaggg gttcgacgat     120
gccacaaatg atattaagga gttggcaaga accatgtcta acatcagtag acagcaaact     180
aataagacta aaggtagtga agatttgatt cgttacttat ctcatatgtc gcaggtgcca     240
ggtgtcgagc cgtataataa tgaaattgag gatacctta a atccggatag cgacaatttc     300
aacgctaaat actgggtgaa aaatttgaga aaattgcacg attcagatcc taactattac     360
aaaccatcgt ctttgggaat tgcttatagg aatttaagag catcggggt tgctgctgac     420
tccgattacc agcccactgt ggacaatgca ttatataagt taggaggtga ggcattcaga     480
tctttgcaaa aagatgatcc ttctcgttac tttgatatat tgaagagcat ggatggtatc     540
atgagacccg gtgaagtcac tgttgtcttg ggtagaccag ttctggttg ctccactttg     600
ttgaagacaa ttgcctctca cacatacggg ttcaaaattg gcgaagaatc caagatttcg     660
tacgatggct taactccaaa agatatagaa aatcagttca gaggtgatgt tgtgtattct     720
gctgagaccg atacccattt ccctcacttg acagtgggag atacc ttaga attcgcagct     780
aaattgagaa caccacaaaa tagaggtaac attgatagag agacttacgc caagcatatg     840
gcgtcagtgt acatggccac atatggttta tcgcatacta gaaacaccaa tgtcgggaat     900
gatttcgtga gaggtgtttc cggtggtgaa cgtaagagag tttccattgc cgaagtctcg     960
ttgtgtggat ctaacattca atgttgggat aacgctactc gtggtttaga ttcggcgact    1020
gcattagaat ttattagagc attaaagaca tcagctacga ttttagatgc tacgccatta    1080
attgctattt accaatgttc tcaagatgcc tacgatttat ttgacaatgt tgttgttttg    1140
tacgaaggac accaaatctt cttcggtaag gcagatgagg ctaaggaata tttcattaat    1200
atgggatggg aatgtccaca agacaaaact acagccgatt tcttaacatc gttaactaac    1260
ccagctgaaa gaaccccaag accaggattt gaaaacagtg ttccttatac tcccaaagaa    1320
ttcgaaaccc actggaaaaa ttctccacaa tacaagaaat tggttgaaga tatagaagaa    1380
tatttccaaa agactgatag tgatagccac ggcgaagagt atcaccaagc acacgttgca    1440
agacaatcta atcacatttc tccaaaatct ccattcaccg tttcgttctt catgcaaacc    1500
agatatatca tgggtagaaa tatattgaga ttaaagggtg atccatctat tgctatccaa    1560
tcgatttcg gtcaagcagt tatgggttta atttgtcat cagttttcta taatttgcaa    1620
cctgtaacag attctttcta ttatagaggt gctgctatgt ttttgctgt tttgttaat    1680
gcattttctt ccttattaga aattatgtcg ttattcgaag caagacctat tgttgaaaaa    1740
cacaaacaat atgctttgta tcgtccatct gctgatgctt tggccggtat tattactgaa    1800
ttgcctacta aacttttat gtctatgagt tttaattttg tattttactt tatggtgcat    1860
tttagacgtg atgcaggaag gtttttcttc tactggttaa tgtgcattat gtgtaccttta    1920
gtcatgtcac atttgtttag atcattgggt gctgtctcta actctttagc tggtgctatg    1980
acacctgcta cggttttatt gatggccatg gttattttca ctggtttcgt tattccaacg    2040
ccaaatatgt tgggctggtc tagatggatt aattatatta accctgttgc atatgtcttc    2100
gaagccttaa tgactaacga gtttagtggt cgtgattttg aatgttcgca atttgttcca    2160
gctggtccaa gttaccaagg tatttctcct gaccaacgaa tttgttctac cactggtagt    2220
agaccgggct cagaagttgt tcgtggttca gagtatcttg ccacgtctta tgaatactac    2280
gcttctcata aatggagaaa tttcggtatt actgttgctt tcgtagtatt tttcttattc    2340
atctatattt cattgactga attcaacaag ggttcaatgc aaaagggaga agttgcattg    2400
```

-continued

```
ttttaaaga gttcattaac ggaccaaaag aagaaatctg gtaaatcgga gacaacctca    2460
aaagatattg aaaactctgc tattccagat gaaaagattt cgcagaagga tcaattagaa    2520
gcaaataaag aaaccgaaac ggctgaaaaa gccttaccat cttccaatga tattttccac    2580
tggagagatt taacgtacca agttaagatt aagtctgagg atcgtgttat tttgaatcat    2640
gtcgatggat gggttaaacc aggtcaattg accgctttaa tgggttcatc aggtgctggt    2700
aagactactt tattgaactg tttgtccgaa agagtcacca caggtgtgat ctcagacggt    2760
gtaagaatgg tgaatggaca ttcattagac tcatcgttcc aaagatctat tggatatgtt    2820
caacaacaag atttgcattt acctacatcc actgtgagag aagcgttaag attttcagcc    2880
caattaaggc agccaaactc agtaacaacc aaagagaaga atgactacgt tgaatacatt    2940
attgatttat tagacatgta cccatatgca gacgcattgg ttggtgttgc tggagaaggt    3000
cttaatgttg aacaacgtaa gagattgacg attggtgttg aattagttgc taagccaaag    3060
ttattattat tcttagatga acctacttcc gggttagatt cgcaaacagc ttggtctatt    3120
tgtaagttga tgaggaagtt agcggatcat ggtcaagcta ttttatgtac tatccatcag    3180
ccatcagcac ttttattaca agaatttgac agattattat tcttacagaa gggaggtaaa    3240
acggtttact ttggagactt aggtgaaaat tgtcagactt tgattaacta ttttcagaag    3300
tacggagcac atcactgtcc agaagaagct aacccagcag aatggatgtt gcaggttgtt    3360
ggtgctgcac caggtagtca cgccaatcag gattatcacg aagtttggag aagttcatca    3420
gaataccaag gcacacaagc ggaattagac aatatggaac gtgaattagt taacttacct    3480
gtggatgaat ctccagaggc taagaagtca tatgctgcac caatttggaa gcaatacctc    3540
attgttacta aaagagtttt ccaacaaaac tggagatctc ctacctatat ctattccaaa    3600
ttatttttgg ttgtttcttc cgctttgttt aacgggtttt cttcttaa ggctgataga    3660 tctatgcaag gattacaaaa ccaaatgttt gctatgttta tgttttgat tccattcaat    3720 actttggtcc aacaaatgtt accatatttc gttaaacaga gagatgtcta tgaagtcaga    3780
gaagcaccat ccaagacatt tagttggttt gctttcgttg ctgctcaaat tacgtccgaa    3840
gttccatacc agatcttctg cggtacaatc gcattccttt gttggttcta tcctgttggt    3900
ttctaccaaa atgcagttcc tactaattct gttgaccaac gtgctgtctt aatgtggatg    3960
tacatttgtt catttatgt ctacacttct accatgggtc aattgtgtat gtcttcaac    4020 gaactcgctg acaatgcggc caatttagct actttgttat tcacaatgtg tttgaatttc    4080
tgtggtgtct tagctggtcc agatgtctta ccaggattct ggattttcat gtacagatgt    4140
tctcctttca cttatttcat ccaaggtatg ttgtcaaccg gtttagcgaa cactaatgcc    4200
gaatgttcta aagctgaatt cttacacttt aagcctaacg aaggtcaatc ttgtggtgaa    4260
tacatgtctg attacatcaa acaagcaggt ggttatttgg ttgacgaaaa ggcttcctct    4320
gaatgtcaat tttgtccaat ggcttctacc aacgatttc tagctagtgt caattcattc    4380
tacgatgaaa gatggagaaa ttggggtatc tttatttgtt tcatcgccat taacattatt    4440
cttacaattt tcttctactg gttagccaga gttccaaagg gtaacagaga aagaagaag    4500 aaataa                                                              4506
```

<210> SEQ ID NO 58
<211> LENGTH: 1501
<212> TYPE: PRT
<213> ORGANISM: Debaryomyces hansenii

<400> SEQUENCE: 58

```
Met Ser Ser Thr Ser Asn Ser Val Glu His Lys Ser Lys Phe Glu Asp
1               5                   10                  15

Ser Asn Ser Val Thr Glu Phe Val Pro Ser Ala Asp Gln Ser Ser Val
            20                  25                  30

Pro Gln Tyr Glu Gly Phe Asp Asp Ala Thr Asn Asp Ile Lys Glu Leu
        35                  40                  45

Ala Arg Thr Met Ser Asn Ile Ser Arg Gln Gln Thr Asn Lys Thr Lys
    50                  55                  60

Gly Ser Glu Asp Leu Ile Arg Tyr Leu Ser His Met Ser Gln Val Pro
65                  70                  75                  80

Gly Val Glu Pro Tyr Asn Asn Glu Ile Glu Asp Thr Leu Asn Pro Asp
                85                  90                  95

Ser Asp Asn Phe Asn Ala Lys Tyr Trp Val Lys Asn Leu Arg Lys Leu
                100                 105                 110

His Asp Ser Asp Pro Asn Tyr Tyr Lys Pro Ser Ser Leu Gly Ile Ala
            115                 120                 125

Tyr Arg Asn Leu Arg Ala Ser Gly Val Ala Ala Asp Ser Asp Tyr Gln
    130                 135                 140

Pro Thr Val Asp Asn Ala Leu Tyr Lys Leu Gly Glu Ala Phe Arg
145                 150                 155                 160

Ser Leu Gln Lys Asp Asp Pro Ser Arg Tyr Phe Asp Ile Leu Lys Ser
                165                 170                 175

Met Asp Gly Ile Met Arg Pro Gly Glu Val Thr Val Leu Gly Arg
                180                 185                 190

Pro Gly Ser Gly Cys Ser Thr Leu Leu Lys Thr Ile Ala Ser His Thr
        195                 200                 205

Tyr Gly Phe Lys Ile Gly Glu Glu Ser Lys Ile Ser Tyr Asp Gly Leu
    210                 215                 220

Thr Pro Lys Asp Ile Glu Asn Gln Phe Arg Gly Asp Val Val Tyr Ser
225                 230                 235                 240

Ala Glu Thr Asp Thr His Phe Pro His Leu Thr Val Gly Asp Thr Leu
                245                 250                 255

Glu Phe Ala Ala Lys Leu Arg Thr Pro Gln Asn Arg Gly Asn Ile Asp
            260                 265                 270

Arg Glu Thr Tyr Ala Lys His Met Ala Ser Val Tyr Met Ala Thr Tyr
        275                 280                 285

Gly Leu Ser His Thr Arg Asn Thr Asn Val Gly Asn Asp Phe Val Arg
    290                 295                 300

Gly Val Ser Gly Gly Glu Arg Lys Arg Val Ser Ile Ala Glu Val Ser
305                 310                 315                 320

Leu Cys Gly Ser Asn Ile Gln Cys Trp Asp Asn Ala Thr Arg Gly Leu
                325                 330                 335

Asp Ser Ala Thr Ala Leu Glu Phe Ile Arg Ala Leu Lys Thr Ser Ala
            340                 345                 350

Thr Ile Leu Asp Ala Thr Pro Leu Ile Ala Ile Tyr Gln Cys Ser Gln
        355                 360                 365

Asp Ala Tyr Asp Leu Phe Asp Asn Val Val Leu Tyr Glu Gly His
    370                 375                 380

Gln Ile Phe Phe Gly Lys Ala Asp Glu Ala Lys Glu Tyr Phe Ile Asn
385                 390                 395                 400

Met Gly Trp Glu Cys Pro Gln Arg Gln Thr Thr Ala Asp Phe Leu Thr
                405                 410                 415

Ser Leu Thr Asn Pro Ala Glu Arg Thr Pro Arg Pro Gly Phe Glu Asn
```

```
                    420             425             430
Ser Val Pro Tyr Thr Pro Lys Glu Phe Glu Thr His Trp Lys Asn Ser
                435             440             445

Pro Gln Tyr Lys Lys Leu Val Glu Asp Ile Glu Tyr Phe Gln Lys
        450             455             460

Thr Asp Ser Asp Ser His Gly Glu Glu Tyr His Gln Ala His Val Ala
465             470             475             480

Arg Gln Ser Asn His Ile Ser Pro Lys Ser Pro Phe Thr Val Ser Phe
                485             490             495

Phe Met Gln Thr Arg Tyr Ile Met Gly Arg Asn Ile Leu Arg Leu Lys
            500             505             510

Gly Asp Pro Ser Ile Ala Ile Gln Ser Ile Phe Gly Gln Ala Val Met
        515             520             525

Gly Leu Ile Leu Ser Ser Val Phe Tyr Asn Leu Gln Pro Val Thr Asp
        530             535             540

Ser Phe Tyr Tyr Arg Gly Ala Ala Met Phe Phe Ala Val Leu Phe Asn
545             550             555             560

Ala Phe Ser Ser Leu Leu Glu Ile Met Ser Leu Phe Glu Ala Arg Pro
                565             570             575

Ile Val Glu Lys His Lys Gln Tyr Ala Leu Tyr Arg Pro Ser Ala Asp
                580             585             590

Ala Leu Ala Gly Ile Ile Thr Glu Leu Pro Thr Lys Leu Phe Met Ser
            595             600             605

Met Ser Phe Asn Phe Val Phe Tyr Phe Met Val His Phe Arg Arg Asp
        610             615             620

Ala Gly Arg Phe Phe Phe Tyr Trp Leu Met Cys Ile Met Cys Thr Leu
625             630             635             640

Val Met Ser His Leu Phe Arg Ser Leu Gly Ala Val Ser Asn Ser Leu
                645             650             655

Ala Gly Ala Met Thr Pro Ala Thr Val Leu Leu Met Ala Met Val Ile
                660             665             670

Phe Thr Gly Phe Val Ile Pro Thr Pro Asn Met Leu Gly Trp Ser Arg
            675             680             685

Trp Ile Asn Tyr Ile Asn Pro Val Ala Tyr Val Phe Glu Ala Leu Met
        690             695             700

Thr Asn Glu Phe Ser Gly Arg Asp Phe Glu Cys Ser Gln Phe Val Pro
705             710             715             720

Ala Gly Pro Ser Tyr Gln Gly Ile Ser Pro Asp Gln Arg Ile Cys Ser
                725             730             735

Thr Thr Gly Ser Arg Pro Gly Ser Glu Val Val Arg Gly Ser Glu Tyr
                740             745             750

Leu Ala Thr Ser Tyr Glu Tyr Tyr Ala Ser His Lys Trp Arg Asn Phe
            755             760             765

Gly Ile Thr Val Ala Phe Val Phe Phe Leu Phe Ile Tyr Ile Ser
        770             775             780

Leu Thr Glu Phe Asn Lys Gly Ser Met Gln Lys Gly Glu Val Ala Leu
785             790             795             800

Phe Leu Lys Ser Ser Leu Thr Asp Gln Lys Lys Ser Gly Lys Ser
                805             810             815

Glu Thr Thr Ser Lys Asp Ile Glu Asn Ser Ala Ile Pro Asp Glu Lys
            820             825             830

Ile Ser Gln Lys Asp Gln Leu Glu Ala Asn Lys Glu Thr Glu Thr Ala
        835             840             845
```

```
Glu Lys Ala Leu Pro Ser Ser Asn Asp Ile Phe His Trp Arg Asp Leu
850                 855                 860

Thr Tyr Gln Val Lys Ile Lys Ser Glu Asp Arg Val Ile Leu Asn His
865                 870                 875                 880

Val Asp Gly Trp Val Lys Pro Gly Gln Leu Thr Ala Leu Met Gly Ser
                885                 890                 895

Ser Gly Ala Gly Lys Thr Thr Leu Leu Asn Cys Leu Ser Glu Arg Val
            900                 905                 910

Thr Thr Gly Val Ile Ser Asp Gly Val Arg Met Val Asn Gly His Ser
        915                 920                 925

Leu Asp Ser Ser Phe Gln Arg Ser Ile Gly Tyr Val Gln Gln Gln Asp
930                 935                 940

Leu His Leu Pro Thr Ser Thr Val Arg Glu Ala Leu Arg Phe Ser Ala
945                 950                 955                 960

Gln Leu Arg Gln Pro Asn Ser Val Thr Thr Lys Glu Lys Asn Asp Tyr
                965                 970                 975

Val Glu Tyr Ile Ile Asp Leu Leu Asp Met Tyr Pro Tyr Ala Asp Ala
                980                 985                 990

Leu Val Gly Val Ala Gly Glu Gly Leu Asn Val Glu Gln Arg Lys Arg
                995                 1000                1005

Leu Thr Ile Gly Val Glu Leu Val Ala Lys Pro Lys Leu Leu Leu
    1010                1015                1020

Phe Leu Asp Glu Pro Thr Ser Gly Leu Asp Ser Gln Thr Ala Trp
    1025                1030                1035

Ser Ile Cys Lys Leu Met Arg Lys Leu Ala Asp His Gly Gln Ala
    1040                1045                1050

Ile Leu Cys Thr Ile His Gln Pro Ser Ala Leu Leu Gln Glu
    1055                1060                1065

Phe Asp Arg Leu Leu Phe Leu Gln Lys Gly Gly Lys Thr Val Tyr
    1070                1075                1080

Phe Gly Asp Leu Gly Glu Asn Cys Gln Thr Leu Ile Asn Tyr Phe
    1085                1090                1095

Gln Lys Tyr Gly Ala His His Cys Pro Glu Glu Ala Asn Pro Ala
    1100                1105                1110

Glu Trp Met Leu Gln Val Val Gly Ala Ala Pro Gly Ser His Ala
    1115                1120                1125

Asn Gln Asp Tyr His Glu Val Trp Arg Ser Ser Glu Tyr Gln
    1130                1135                1140

Gly Thr Gln Ala Glu Leu Asp Asn Met Glu Arg Glu Leu Val Asn
    1145                1150                1155

Leu Pro Val Asp Glu Ser Pro Glu Ala Lys Lys Ser Tyr Ala Ala
    1160                1165                1170

Pro Ile Trp Lys Gln Tyr Leu Ile Val Thr Lys Arg Val Phe Gln
    1175                1180                1185

Gln Asn Trp Arg Ser Pro Thr Tyr Ile Tyr Ser Lys Leu Phe Leu
    1190                1195                1200

Val Val Ser Ser Ala Leu Phe Asn Gly Phe Ser Phe Phe Lys Ala
    1205                1210                1215

Asp Arg Ser Met Gln Gly Leu Gln Asn Gln Met Phe Ala Met Phe
    1220                1225                1230

Met Phe Leu Ile Pro Phe Asn Thr Leu Val Gln Gln Met Leu Pro
    1235                1240                1245

Tyr Phe Val Lys Gln Arg Asp Val Tyr Glu Val Arg Glu Ala Pro
    1250                1255                1260
```

| | | | | | | | | | | |
|---|---|---|---|---|---|---|---|---|---|---|
| Ser | Lys | Thr | Phe | Ser | Trp | Phe | Ala | Phe | Val | Ala | Ala | Gln | Ile | Thr |
| | 1265 | | | | 1270 | | | | 1275 | |

Ser Lys Thr Phe Ser Trp Phe Ala Phe Val Ala Ala Gln Ile Thr
    1265                1270                1275

Ser Glu Val Pro Tyr Gln Ile Phe Cys Gly Thr Ile Ala Phe Leu
    1280                1285                1290

Cys Trp Phe Tyr Pro Val Gly Phe Tyr Gln Asn Ala Val Pro Thr
    1295                1300                1305

Asn Ser Val Asp Gln Arg Ala Val Leu Met Trp Met Tyr Ile Cys
    1310                1315                1320

Ser Phe Tyr Val Tyr Thr Ser Thr Met Gly Gln Leu Cys Met Ser
    1325                1330                1335

Phe Asn Glu Leu Ala Asp Asn Ala Ala Asn Leu Ala Thr Leu Leu
    1340                1345                1350

Phe Thr Met Cys Leu Asn Phe Cys Gly Val Leu Ala Gly Pro Asp
    1355                1360                1365

Val Leu Pro Gly Phe Trp Ile Phe Met Tyr Arg Cys Ser Pro Phe
    1370                1375                1380

Thr Tyr Phe Ile Gln Gly Met Leu Ser Thr Gly Leu Ala Asn Thr
    1385                1390                1395

Asn Ala Glu Cys Ser Lys Ala Glu Phe Leu His Phe Lys Pro Asn
    1400                1405                1410

Glu Gly Gln Ser Cys Gly Glu Tyr Met Ser Asp Tyr Ile Lys Gln
    1415                1420                1425

Ala Gly Gly Tyr Leu Val Asp Glu Lys Ala Ser Ser Glu Cys Gln
    1430                1435                1440

Phe Cys Pro Met Ala Ser Thr Asn Asp Phe Leu Ala Ser Val Asn
    1445                1450                1455

Ser Phe Tyr Asp Glu Arg Trp Arg Asn Trp Gly Ile Phe Ile Cys
    1460                1465                1470

Phe Ile Ala Ile Asn Ile Ile Leu Thr Ile Phe Phe Tyr Trp Leu
    1475                1480                1485

Ala Arg Val Pro Lys Gly Asn Arg Glu Lys Lys Lys Lys
    1490                1495                1500

<210> SEQ ID NO 59
<211> LENGTH: 4593
<212> TYPE: DNA
<213> ORGANISM: Schizosaccharomyces pombe

<400> SEQUENCE: 59

```
atgaatcaaa attcggatac tactcacggt caggccttag gcagtacttt aaatcatacc        60
accgaggtta cgcgtatttc taattcctct gatcatttcg aggattcttc ttcgaatgtt       120
gacgagtctt tagattcttc taatccttca tccaatgaga aggcatcaca cactaatgag       180
gaataccgtt caaaaggtaa tcaaagttac gtcccatctt catcaaacga accctcccca       240
gaatcctcat cgaattcgga ttcttcctca tctgatgatt catcggtcga ccgtttggcc       300
ggtgatccct ttgaactagg ggaaaacttc aacttgaagc attatttaag agcatacaaa       360
gattctttac aacgagacga tatcatcact cgtagtagtg tgtctgcat gcgcgaccat        420
agtgtttatg gcgttggttc tggatatgaa tttttgaaaa catttcctga tattttttta       480
caaccttatc gagctatcac tgaaaaacaa gtggtgaaa aagccatttt aagtcattgt        540
catgctcttg ccaatgctgg tgaactggtg atggttttgg acaaccagg ttctggatgt        600
tccactttct tgcgttcagt tactagcgat actgttcact acaagcgtgt cgagggaacc       660
actcattatg acggtattga caaggccgac atgaaaaagt ttttcccgg tgatctttta        720
```

| | |
|---|---|
| tacagtggtg aaaacgatgt ccatttccca tctttgacta ccgctgaaac ccttgatttt | 780 |
| gcggctaaat gccgtacccc aaacaaccgt ccttgcaacc tcacccgtca agaatatgtg | 840 |
| agtcgtgaga ggcatttaat tgctaccgca tttggcttga cacacacttt caataccaag | 900 |
| gtaggtaatg atttcgtacg tggtgtctct ggtggtgaac gtaagcgtgt aactattagt | 960 |
| gaaggttttg ctactcgtcc aactatcgct tgctgggata atagtactcg tggtttggac | 1020 |
| tctagtacgg ctttcgagtt cgtcaatgtc cttcgcactt gtgccaatga acttaaaatg | 1080 |
| acatccttcg ttactgcata ccaagcttcg gaaaagattt acaaactttt cgatcgaatt | 1140 |
| tgtgtacttt atgccggtag gcaaatttat tatggaccag ctgacaaagc caagcaatac | 1200 |
| ttcttagata tggggtttga ctgtcatcct cgtgaaacaa ctcctgactt cctcactgct | 1260 |
| atttctgacc cgaaggctag gtttcctaga aagggtttcg aaaatcgcgt tcccagaacc | 1320 |
| cctgatgagt ttgaacaaat gtggcgcaat agttctgtat atgctgacct tatggccgaa | 1380 |
| atggaaagct atgacaaacg gtggaccgag actactcctg cttcttctga agccccgaa | 1440 |
| aaagacaact ttggaagcga tatctctgcc actaccaagc atgagctcta tcgtcaaagt | 1500 |
| gcggtagcgg aaaagagtaa acgtgttaag gatacctctc cgtatactgt gacttttagt | 1560 |
| caacagttgt ggtattgttt agctaggtca tgggagagat atatcaatga tcctgcatat | 1620 |
| attggttcaa tggcttttgc tttccttttc caatctctta ttatcggttc tattttctac | 1680 |
| gatatgaaat taaacaccgt tgatgtattc tcacgtggtg gtgttctttt cttctctatt | 1740 |
| ctgtttttgcg cacttcagag tctttctgaa atcgctaata tgttttccca acgacccatc | 1800 |
| attgctaagc atagagcttc tgctttgtac catcctgctg cagatgttat tagtagcttg | 1860 |
| attgtcgatc tacctttcag attcattaat atttcggttt tctcaattgt gttgtatttt | 1920 |
| ttaacaaatt taaagaggac tgctggcgga ttttggactt acttttgtt ccttttcata | 1980 |
| ggtgctactt gtatgtctgc ctttttcga tcattagctg gaattatgcc caatgttgaa | 2040 |
| tctgcatctg ctttgggtgg tatcggtgtg cttgcaattg ccatttacac tggttatgct | 2100 |
| attcctaata tcgacgttgg atggtggttc cgctggattg cttatctcga cccgttgcaa | 2160 |
| tttggttttg agtcttaat gattaatgaa ttcaaggcac gacagttcga atgctctcaa | 2220 |
| ttgattccgt acggtagtgg atatgacaat tatcctgtag ctaacaaaat ctgtcccgtc | 2280 |
| acctctgcag aacctggaac agattacgtt gacggctcaa cttacttgta tattagtttc | 2340 |
| aactacaaga cgcgtcaatt atggagaaat ttggctatta ttattggata ttatgcgttc | 2400 |
| ttggtatttg tcaacatcgt cgccagtgaa actcttaatt tcaacgattt gaaaggtgaa | 2460 |
| tatctggtct ttcgccgcgg ccatgctcct gacgctgtaa aagcagctgt caatgaaggt | 2520 |
| ggaaaaccgc tggatttaga aactggtcaa gatactcaag gtggtgacgt tgttaaagag | 2580 |
| tctccggaca acgaagaaga gcttaacaag gaatatgaag gaattgaaaa aggccatgac | 2640 |
| atttcagct ggagaaatct taactacgac attcaaataa aaggtgagca tcgccggtta | 2700 |
| cttaatggtg tgcaaggctt tgttgttcca ggtaaattga cggctttgat gggtgaatcc | 2760 |
| ggtgctggta aaaccacttt actaaatgta cttgctcaac gtgttgacac tggtgtagta | 2820 |
| actggcgaca tgttggttaa tggtagagga ttggattcaa cttccaacg gcgcactggt | 2880 |
| tatgtacaac agcaggatgt ccacattggt gaatctacgg ttagagaagc gttgcgtttc | 2940 |
| agtgctgctc tacgtcaacc tgcttccgtt cctcttttcgg aaaagtacga atatgtcgaa | 3000 |
| tcagtcatta aacttttgga aatggagagc tatgctgaag caattatcgg tactcctggc | 3060 |
| tccggattga acgtagaaca acgtaagcgt gcaaccattg gtgtcgagtt ggctgcgaag | 3120 |

```
cctgctttat tgttgttttt agacgagcca acttctggtc tagatagtca gtctgcatgg    3180
tccattgttt gtttcttgcg aaaattagct gatgctggtc aagcaattct ttgtacaatc    3240
catcaaccca gtgccgtact gtttgatcaa tttgatagat tgttactgct acagaaaggt    3300
ggtaaaacag tgtactttgg tgatatagga gaacattcta agactttgtt aaattacttt    3360
gaatctcatg gagcagtaca ttgtcctgac gacggtaatc cagctgaata cattttagat    3420
gttattggtg ctggtgccac tgccactact aatcgtgatt ggcatgaagt ttggaataac    3480
tcagaagaac gtaaagccat tagtgcagag ctagacaaaa ttaacgcttc attctcaaac    3540
agtgaggata aaagacttt gtcaaaggaa gataggagca cttacgccat gcctctgtgg    3600
ttccaagtca aaatggtcat gaccagaaat ttccagtctt attggagaga gccctctata    3660
ttgatgtcta aattagcact ggatattttc gctggtttat ttattggatt tacatttat     3720 aatcaaggtc tcggtgtaca gaatattcag acaagctttt cgctgtgtt tatggcaacc    3780 gttcttgcag ttcctttgat taatggtctt caaccaaaat ttattgagtt gcgtaacgtc    3840
tttgaagtta gagaaaagcc ttcgaatatt tacagttggg ttgcattcgt attttcagcc    3900
attatagtag aaattccatt taacctggtg tttggcacgc ttttcttcct ttgttggttt    3960
tatccaatca gtttttataa gcatattcat catcctggtg acaaaactgg ttacgcttgg    4020
ttgctttata tgttcttcca aatgtacttc tcaactttg gccaagctgt cgccagtgcg    4080
tgccctaatg ctcaaacagc gtccgttgtc aacagtttgt tattcacatt cgtgattaca    4140
tttaacggtg ttctgcagcc taatagtaat ttggtcggat tttggcattg gatgcattcg    4200
ttgactccgt ttacctattt gatcgaagga ttactttctg atttggtgca tggacttcca    4260
gttgaatgca gtctcatga gatgcttact atcaaccctc ctagcggtca acatgcggt     4320 gaatatatga gtgctttctt aactaataac acagctgctg gaaacctctt aaatcctaat    4380 gctacaaccct catgcagtta ctgtccatat caaaccgctg accagttttt ggagcggttt    4440
agtatgcgtt atactcatcg ctggagaaat ttgggtatct ttgttggtta tgtgttcttc    4500
aatatctttg cggtgctttt gttgttttac gtattccgag tcatgaagct tagaagtact    4560
tggcttggta aaaagattac cggaactggt taa                                 4593
```

<210> SEQ ID NO 60
<211> LENGTH: 1530
<212> TYPE: PRT
<213> ORGANISM: Schizosaccharomyces pombe

<400> SEQUENCE: 60

```
Met Asn Gln Asn Ser Asp Thr Thr His Gly Gln Ala Leu Gly Ser Thr
1               5                   10                  15

Leu Asn His Thr Thr Glu Val Thr Arg Ile Ser Asn Ser Ser Asp His
            20                  25                  30

Phe Glu Asp Ser Ser Asn Val Asp Glu Ser Leu Asp Ser Ser Asn
        35                  40                  45

Pro Ser Ser Asn Glu Lys Ala Ser His Thr Asn Glu Glu Tyr Arg Ser
    50                  55                  60

Lys Gly Asn Gln Ser Tyr Val Pro Ser Ser Asn Glu Pro Ser Pro
65                  70                  75                  80

Glu Ser Ser Ser Asn Ser Asp Ser Ser Ser Asp Asp Ser Ser Val
                85                  90                  95

Asp Arg Leu Ala Gly Asp Pro Phe Glu Leu Gly Glu Asn Phe Asn Leu
            100                 105                 110
```

-continued

```
Lys His Tyr Leu Arg Ala Tyr Lys Asp Ser Leu Gln Arg Asp Asp Ile
        115                 120                 125

Ile Thr Arg Ser Ser Gly Val Cys Met Arg Asp His Ser Val Tyr Gly
    130                 135                 140

Val Gly Ser Gly Tyr Glu Phe Leu Lys Thr Phe Pro Asp Ile Phe Leu
145                 150                 155                 160

Gln Pro Tyr Arg Ala Ile Thr Glu Lys Gln Val Val Glu Lys Ala Ile
                165                 170                 175

Leu Ser His Cys His Ala Leu Ala Asn Ala Gly Glu Leu Val Met Val
            180                 185                 190

Leu Gly Gln Pro Gly Ser Gly Cys Ser Thr Phe Leu Arg Ser Val Thr
        195                 200                 205

Ser Asp Thr Val His Tyr Lys Arg Val Glu Gly Thr Thr His Tyr Asp
    210                 215                 220

Gly Ile Asp Lys Ala Asp Met Lys Lys Phe Phe Pro Gly Asp Leu Leu
225                 230                 235                 240

Tyr Ser Gly Glu Asn Asp Val His Phe Pro Ser Leu Thr Thr Ala Glu
                245                 250                 255

Thr Leu Asp Phe Ala Ala Lys Cys Arg Thr Pro Asn Asn Arg Pro Cys
            260                 265                 270

Asn Leu Thr Arg Gln Glu Tyr Val Ser Arg Glu Arg His Leu Ile Ala
        275                 280                 285

Thr Ala Phe Gly Leu Thr His Thr Phe Asn Thr Lys Val Gly Asn Asp
    290                 295                 300

Phe Val Arg Gly Val Ser Gly Gly Glu Arg Lys Arg Val Thr Ile Ser
305                 310                 315                 320

Glu Gly Phe Ala Thr Arg Pro Thr Ile Ala Cys Trp Asp Asn Ser Thr
                325                 330                 335

Arg Gly Leu Asp Ser Ser Thr Ala Phe Glu Phe Val Asn Val Leu Arg
            340                 345                 350

Thr Cys Ala Asn Glu Leu Lys Met Thr Ser Phe Val Thr Ala Tyr Gln
        355                 360                 365

Ala Ser Glu Lys Ile Tyr Lys Leu Phe Asp Arg Ile Cys Val Leu Tyr
    370                 375                 380

Ala Gly Arg Gln Ile Tyr Tyr Gly Pro Ala Asp Lys Ala Lys Gln Tyr
385                 390                 395                 400

Phe Leu Asp Met Gly Phe Asp Cys His Pro Arg Glu Thr Thr Pro Asp
                405                 410                 415

Phe Leu Thr Ala Ile Ser Asp Pro Lys Ala Arg Phe Pro Arg Lys Gly
            420                 425                 430

Phe Glu Asn Arg Val Pro Arg Thr Pro Asp Glu Phe Glu Gln Met Trp
        435                 440                 445

Arg Asn Ser Ser Val Tyr Ala Asp Leu Met Ala Glu Met Glu Ser Tyr
    450                 455                 460

Asp Lys Arg Trp Thr Glu Thr Pro Ala Ser Ser Glu Ala Pro Glu
465                 470                 475                 480

Lys Asp Asn Phe Gly Ser Asp Ile Ser Ala Thr Thr Lys His Glu Leu
                485                 490                 495

Tyr Arg Gln Ser Ala Val Ala Glu Lys Ser Lys Arg Val Lys Asp Thr
            500                 505                 510

Ser Pro Tyr Thr Val Thr Phe Ser Gln Gln Leu Trp Tyr Cys Leu Ala
        515                 520                 525

Arg Ser Trp Glu Arg Tyr Ile Asn Asp Pro Ala Tyr Ile Gly Ser Met
    530                 535                 540
```

```
Ala Phe Ala Phe Leu Phe Gln Ser Leu Ile Ile Gly Ser Ile Phe Tyr
545                 550                 555                 560

Asp Met Lys Leu Asn Thr Val Asp Val Phe Ser Arg Gly Gly Val Leu
                565                 570                 575

Phe Phe Ser Ile Leu Phe Cys Ala Leu Gln Ser Leu Ser Glu Ile Ala
            580                 585                 590

Asn Met Phe Ser Gln Arg Pro Ile Ile Ala Lys His Arg Ala Ser Ala
        595                 600                 605

Leu Tyr His Pro Ala Ala Asp Val Ile Ser Ser Leu Ile Val Asp Leu
    610                 615                 620

Pro Phe Arg Phe Ile Asn Ile Ser Val Phe Ser Ile Val Leu Tyr Phe
625                 630                 635                 640

Leu Thr Asn Leu Lys Arg Thr Ala Gly Gly Phe Trp Thr Tyr Phe Leu
                645                 650                 655

Phe Leu Phe Ile Gly Ala Thr Cys Met Ser Ala Phe Phe Arg Ser Leu
            660                 665                 670

Ala Gly Ile Met Pro Asn Val Glu Ser Ala Ser Ala Leu Gly Gly Ile
        675                 680                 685

Gly Val Leu Ala Ile Ala Ile Tyr Thr Gly Tyr Ala Ile Pro Asn Ile
    690                 695                 700

Asp Val Gly Trp Trp Phe Arg Trp Ile Ala Tyr Leu Asp Pro Leu Gln
705                 710                 715                 720

Phe Gly Phe Glu Ser Leu Met Ile Asn Glu Phe Lys Ala Arg Gln Phe
                725                 730                 735

Glu Cys Ser Gln Leu Ile Pro Tyr Gly Ser Gly Tyr Asp Asn Tyr Pro
            740                 745                 750

Val Ala Asn Lys Ile Cys Pro Val Thr Ser Ala Glu Pro Gly Thr Asp
        755                 760                 765

Tyr Val Asp Gly Ser Thr Tyr Leu Tyr Ile Ser Phe Asn Tyr Lys Thr
    770                 775                 780

Arg Gln Leu Trp Arg Asn Leu Ala Ile Ile Ile Gly Tyr Tyr Ala Phe
785                 790                 795                 800

Leu Val Phe Val Asn Ile Val Ala Ser Glu Thr Leu Asn Phe Asn Asp
                805                 810                 815

Leu Lys Gly Glu Tyr Leu Val Phe Arg Arg Gly His Ala Pro Asp Ala
            820                 825                 830

Val Lys Ala Ala Val Asn Glu Gly Gly Lys Pro Leu Asp Leu Glu Thr
        835                 840                 845

Gly Gln Asp Thr Gln Gly Gly Asp Val Val Lys Glu Ser Pro Asp Asn
    850                 855                 860

Glu Glu Glu Leu Asn Lys Glu Tyr Glu Gly Ile Glu Lys Gly His Asp
865                 870                 875                 880

Ile Phe Ser Trp Arg Asn Leu Asn Tyr Asp Ile Gln Ile Lys Gly Glu
                885                 890                 895

His Arg Arg Leu Leu Asn Gly Val Gln Gly Phe Val Val Pro Gly Lys
            900                 905                 910

Leu Thr Ala Leu Met Gly Glu Ser Gly Ala Gly Lys Thr Thr Leu Leu
        915                 920                 925

Asn Val Leu Ala Gln Arg Val Asp Thr Gly Val Val Thr Gly Asp Met
    930                 935                 940

Leu Val Asn Gly Arg Gly Leu Asp Ser Thr Phe Gln Arg Arg Thr Gly
945                 950                 955                 960

Tyr Val Gln Gln Gln Asp Val His Ile Gly Glu Ser Thr Val Arg Glu
                965                 970                 975
```

-continued

```
Ala Leu Arg Phe Ser Ala Ala Leu Arg Gln Pro Ala Ser Val Pro Leu
            980                 985                 990

Ser Glu Lys Tyr Glu Tyr Val Glu Ser Val Ile Lys Leu Leu Glu Met
            995                1000                1005

Glu Ser Tyr Ala Glu Ala Ile Ile Gly Thr Pro Gly Ser Gly Leu
        1010                1015                1020

Asn Val Glu Gln Arg Lys Arg Ala Thr Ile Gly Val Glu Leu Ala
        1025                1030                1035

Ala Lys Pro Ala Leu Leu Leu Phe Leu Asp Glu Pro Thr Ser Gly
        1040                1045                1050

Leu Asp Ser Gln Ser Ala Trp Ser Ile Val Cys Phe Leu Arg Lys
        1055                1060                1065

Leu Ala Asp Ala Gly Gln Ala Ile Leu Cys Thr Ile His Gln Pro
        1070                1075                1080

Ser Ala Val Leu Phe Asp Gln Phe Asp Arg Leu Leu Leu Leu Gln
        1085                1090                1095

Lys Gly Gly Lys Thr Val Tyr Phe Gly Asp Ile Gly Glu His Ser
        1100                1105                1110

Lys Thr Leu Leu Asn Tyr Phe Glu Ser His Gly Ala Val His Cys
        1115                1120                1125

Pro Asp Asp Gly Asn Pro Ala Glu Tyr Ile Leu Asp Val Ile Gly
        1130                1135                1140

Ala Gly Ala Thr Ala Thr Thr Asn Arg Asp Trp His Glu Val Trp
        1145                1150                1155

Asn Asn Ser Glu Glu Arg Lys Ala Ile Ser Ala Glu Leu Asp Lys
        1160                1165                1170

Ile Asn Ala Ser Phe Ser Asn Ser Glu Asp Lys Lys Thr Leu Ser
        1175                1180                1185

Lys Glu Asp Arg Ser Thr Tyr Ala Met Pro Leu Trp Phe Gln Val
        1190                1195                1200

Lys Met Val Met Thr Arg Asn Phe Gln Ser Tyr Trp Arg Glu Pro
        1205                1210                1215

Ser Ile Leu Met Ser Lys Leu Ala Leu Asp Ile Phe Ala Gly Leu
        1220                1225                1230

Phe Ile Gly Phe Thr Phe Tyr Asn Gln Gly Leu Gly Val Gln Asn
        1235                1240                1245

Ile Gln Asn Lys Leu Phe Ala Val Phe Met Ala Thr Val Leu Ala
        1250                1255                1260

Val Pro Leu Ile Asn Gly Leu Gln Pro Lys Phe Ile Glu Leu Arg
        1265                1270                1275

Asn Val Phe Glu Val Arg Glu Lys Pro Ser Asn Ile Tyr Ser Trp
        1280                1285                1290

Val Ala Phe Val Phe Ser Ala Ile Ile Val Glu Ile Pro Phe Asn
        1295                1300                1305

Leu Val Phe Gly Thr Leu Phe Phe Leu Cys Trp Phe Tyr Pro Ile
        1310                1315                1320

Lys Phe Tyr Lys His Ile His His Pro Gly Asp Lys Thr Gly Tyr
        1325                1330                1335

Ala Trp Leu Leu Tyr Met Phe Phe Gln Met Tyr Phe Ser Thr Phe
        1340                1345                1350

Gly Gln Ala Val Ala Ser Cys Pro Asn Ala Gln Thr Ala Ser
        1355                1360                1365

Val Val Asn Ser Leu Leu Phe Thr Phe Val Ile Thr Phe Asn Gly
        1370                1375                1380
```

| | | | | | | | | | |
|---|---|---|---|---|---|---|---|---|---|
| Val | Leu | Gln | Pro | Asn | Ser | Asn | Leu | Val | Gly | Phe | Trp | His | Trp | Met |
| 1385 | | | | 1390 | | | | | 1395 | | | | | |

His Ser Leu Thr Pro Phe Thr Tyr Leu Ile Glu Gly Leu Leu Ser
    1400            1405                1410

Asp Leu Val His Gly Leu Pro Val Glu Cys Lys Ser His Glu Met
    1415            1420                1425

Leu Thr Ile Asn Pro Pro Ser Gly Gln Thr Cys Gly Glu Tyr Met
    1430            1435                1440

Ser Ala Phe Leu Thr Asn Asn Thr Ala Ala Gly Asn Leu Leu Asn
    1445            1450                1455

Pro Asn Ala Thr Thr Ser Cys Ser Tyr Cys Pro Tyr Gln Thr Ala
    1460            1465                1470

Asp Gln Phe Leu Glu Arg Phe Ser Met Arg Tyr Thr His Arg Trp
    1475            1480                1485

Arg Asn Leu Gly Ile Phe Val Gly Tyr Val Phe Phe Asn Ile Phe
    1490            1495                1500

Ala Val Leu Leu Leu Phe Tyr Val Phe Arg Val Met Lys Leu Arg
    1505            1510                1515

Ser Thr Trp Leu Gly Lys Lys Ile Thr Gly Thr Gly
    1520            1525                1530

<210> SEQ ID NO 61
<211> LENGTH: 448
<212> TYPE: DNA
<213> ORGANISM: Saccharomyces cerevisiae

<400> SEQUENCE: 61
cccattaccg acatttgggc gctatacgtg catatgttca tgtatgtatc tgtatttaaa      60
acacttttgt attatttttc ctcatatatg tgtataggtt tatacggatg atttaattat     120
tacttcacca ccctttattt caggctgata tcttagcctt gttactagtt agaaaaagac     180 attttttgctg tcagtcactg tcaagagatt cttttgctgg catttcttct agaagcaaaa    240
agagcgatgc gtcttttccg ctgaaccgtt ccagcaaaaa agactaccaa cgcaatatgg     300
attgtcagaa tcatataaaa gagaagcaaa taactccttg tcttgtatca attgcattat     360
aatatcttct tgttagtgca atatcatata gaagtcatcg aaatagatat taagaaaaac     420
aaactgtaca atcaatcaat caatcatc                                        448

<210> SEQ ID NO 62
<211> LENGTH: 270
<212> TYPE: DNA
<213> ORGANISM: Saccharomyces cerevisiae

<400> SEQUENCE: 62
gacctcgagt catgtaatta gttatgtcac gcttacattc acgccctccc cccacatccg      60
ctctaaccga aaaggaagga gttagacaac ctgaagtcta ggtccctatt tattttttta     120
tagttatgtt agtattaaga acgttattta tatttcaaat ttttcttttt tttctgtaca     180
gacgcgtgta cgcatgtaac attatactga aaaccttgct tgagaaggtt ttgggacgct     240
cgaaggcttt aatttgcggc cggtacccaa                                      270

<210> SEQ ID NO 63
<211> LENGTH: 643
<212> TYPE: DNA
<213> ORGANISM: Saccharomyces cerevisiae

```
<400> SEQUENCE: 63
gaaatgaata acaatactga cagtactaaa taattgccta cttggcttca catacgttgc      60
atacgtcgat atagataata atgataatga cagcaggatt atcgtaatac gtaatagttg     120
aaaatctcaa aaatgtgtgg gtcattacgt aaataatgat aggaatggga ttcttctatt     180
tttccttttt ccattctagc agccgtcggg aaaacgtggc atcctctctt cgggctcaa      240
ttggagtcac gctgccgtga gcatcctctc tttccatatc taacaactga gcacgtaacc     300
aatggaaaag catgagctta gcgttgctcc aaaaagtat tggatggtta ataccatttg      360
tctgttctct tctgactttg actcctcaaa aaaaaaaat ctacaatcaa cagatcgctt      420
caattacgcc ctcacaaaaa cttttttcct tcttcttcgc ccacgttaaa ttttatccct     480
catgttgtct aacggatttc tgcacttgat ttattataaa aagacaaaga cataatactt     540
ctctatcaat ttcagttatt gttcttcctt gcgttattct tctgttcttc ttttctttt      600
gtcatatata accataacca agtaatacat attcaaatct aga                       643

<210> SEQ ID NO 64
<211> LENGTH: 316
<212> TYPE: DNA
<213> ORGANISM: Saccharomyces cerevisiae

<400> SEQUENCE: 64
gagtaagcga atttcttatg atttatgatt tttattatta ataagttat aaaaaaaata      60
agtgtataca aattttaaag tgactcttag gttttaaaac gaaaattctt attcttgagt     120
aactctttcc tgtaggtcag gttgctttct caggtatagc atgaggtcgc tcttattgac     180
cacacctcta ccggcatgcc gagcaaatgc ctgcaaatcg ctccccattt cacccaattg     240
tagatatgct aactccagca atgagttgat gaatctcggt gtgtattta tgtcctcaga     300
ggacaacacc tgtggt                                                    316

<210> SEQ ID NO 65
<211> LENGTH: 753
<212> TYPE: DNA
<213> ORGANISM: Saccharomyces cerevisiae

<400> SEQUENCE: 65
gcatgcttgc atttagtcgt gcaatgtatg actttaagat ttgtgagcag gaagaaaagg      60
gagaatcttc taacgataaa cccttgaaaa actgggtaga ctacgctatg ttgagttgct     120
acgcaggctg cacaattaca cgagaatgct cccgcctagg atttaaggct aagggacgtg     180
caatgcagac gacagatcta atgaccgtgt cggtgaagt gttcgccaaa cttttcggtt      240
aacacatgca gtgatgcacg cgcgatggtg ctaagttaca tatatatata tatagccata     300
gtgatgtcta agtaacctt atggtatatt tcttaatgtg gaaagatact agcgcgcgca      360
cccacacaca agcttcgtct tttcttgaag aaagaggaa gctcgctaaa tgggattcca      420
ctttccgttc cctgccagct gatggaaaaa ggttagtgga acgatgaaga ataaaaagag     480
agatccactg aggtgaaatt tcagctgaca gcgagtttca tgatcgtgat gaacaatggt     540
aacgagttgt ggctgttgcc agggaggggtg gttctcaact tttaatgtat ggccaaatcg     600
ctacttgggg ttgttatata acaaagaaga ataatgaac tgattctctt cctccttctt      660
gtcctttctt aattctgttg taattacctt cctttgtaat ttttttgta attattcttc      720
ttaataatcc aaacaaacac acatattaca ata                                 753
```

YEAST WITH INCREASED BUTANOL TOLERANCE INVOLVING A MULTIDRUG EFFLUX PUMP GENE

CROSS-REFERENCE TO RELATED APPLICATIONS

This application is related to and claims the benefit of U.S. Provisional Application No. 61/156,067 filed on Feb. 27, 2009, which is hereby incorporated by reference in its entirety.

FIELD OF THE INVENTION

The invention relates to the field of microbiology and genetic engineering. More specifically, a yeast gene that contributes to the cell response to butanol was identified. This gene may be engineered to improve growth yield in the presence of butanol.

BACKGROUND OF THE INVENTION

Butanol is an important industrial chemical, useful as a fuel additive, as a feedstock chemical in the plastics industry, and as a foodgrade extractant in the food and flavor industry. Each year 10 to 12 billion pounds of butanol are produced by petrochemical means and the need for this commodity chemical will likely increase.

Butanol may be made through chemical synthesis or by fermentation. Isobutanol is produced biologically as a by-product of yeast fermentation. It is a component of "fusel oil" that forms as a result of incomplete metabolism of amino acids by this group of fungi. Isobutanol is specifically produced from catabolism of L-valine and the yield is typically very low. Additionally, recombinant microbial production hosts, expressing a 1-butanol biosynthetic pathway (Donaldson et al., co-pending and commonly owned U.S. Patent Application Publication No. US20080182308A1), a 2-butanol biosynthetic pathway (Donaldson et al., co-pending and commonly owned U.S. Patent Publication Nos. US 20070259410A1 and US 20070292927), and an isobutanol biosynthetic pathway (Maggio-Hall et al., co-pending and commonly owned U.S. Patent Publication No. US 20070092957) have been described.

Biological production of butanols is believed to be limited by butanol toxicity to the host microorganism used in fermentation for butanol production. Yeast are typically sensitive to butanol in the medium. Using a screen for 1-butanol insensitive *Saccharomyces cerevisiae* mutants, Lorenz et al. (Molec. Biol. of the Cell (2000) 11:183-199) identified proteins that regulate polarized growth (BUD8, BEM1, BEM4, and FIG1), mitochondrial function (MSM1, MRP21, and HM11), and a transcriptional regulator (CHD1). They also found that 1-butanol stimulates filamentous growth in haploid cells and induces cell elongation and changes in budding pattern, leading to a pseudohyphal morphology. Ashe et al. (The EMBO Journal (2001) 20:6464-6474) found that butanol brings about a rapid inhibition of translation at the initiation step in *Saccharomyces cerevisiae*. The GCD1-P180 allele has a single amino acid change in Gcd1p, which is part of the eIF2B guanine nucleotide complex that is responsible for recycling eIF2-GDP to eIF2-GTP, that allows translational regulation upon butanol addition. Smirnova et al. (Molecular and Cellular Biology (2005) 25:9340-9340) found by using microarray analysis that with addition of fusel alcohol, there is widespread translational reprogramming in yeast. These studies all indicate the complexity of butanol sensitivity in yeast.

A pleiotropic drug resistant sake yeast with improved fermentative activity was shown to have increased levels of the PDR5 mRNA (Watanabe, M., Mizoguchi, H., and Nishimura, A. (2000) *J Biosci Bioeng* 89, 569-76).

There remains a need for yeast cells with increased tolerance to butanol, as well as methods of producing butanols using yeast host strains that are more tolerant to these chemicals.

SUMMARY OF THE INVENTION

The invention provides a recombinant yeast cell that is engineered to produce butanol and that is engineered to have decreased activity of a multidrug resistance ATP-binding cassette transporter protein encoded by PDR5, CDR1 or BFR1 genes. This decreased activity confers on the cell increased tolerance to butanol. The present recombinant yeast cell may be used for production of butanol. Butanol refers herein to 1-butanol, 2-butanol, and/or isobutanol.

In one aspect, a recombinant yeast cell comprising at least one genetic modification that reduces Pdr5p activity wherein said yeast cell has improved tolerance to butanol and isomers thereof as compared to a yeast cell that lacks said modification, is provided.

Also provided, is recombinant yeast cell comprising at least one genetic modification that decreases activity of a multidrug resistance ATP-binding cassette transporter protein encoded by a PDR5, CDR1, or BFR1 gene wherein said yeast cell has improved tolerance to butanol and isomers thereof as compared to a yeast cell that lacks said modification.

The yeast cells described above may further comprise a butanol biosynthetic pathway. The butanol biosynthetic pathway may be selected from the group consisting of:
 a) a 1-butanol biosynthetic pathway
 b) a 2-butanol biosynthetic pathway; and
 c) an isobutanol biosynthetic pathway.

The yeast cell may have at least about a 1.8-fold improvement in growth yield in 0.75% (w/v) isobutanol as compared to a parental cell that does not have said genetic modification.

The genetic modification may substantially eliminate expression of a multidrug resistance ATP-binding cassette transporter protein encoded by a PDR5, CDR1 or BFR1 gene that is endogenous to the cell.

Also provided is a method for the production of butanol or an isomer thereof comprising growing the yeast cells as described herein under conditions wherein butanol or an isomer thereof is produced and optionally recovering said butanol or isomer thereof. The method is improved by the genetic modifications described herein in that said modifications provide tolerance to butanol.

Also provided is a method for producing a recombinant yeast cell having increased tolerance to butanol comprising:
 a) providing a recombinant yeast cell comprising a butanol biosynthetic pathway selected from the group consisting of:
  i) a 1-butanol biosynthetic pathway
  ii) a 2-butanol biosynthetic pathway; and
  iii) an isobutanol biosynthetic pathway; and
 b) engineering the yeast cell of (a) to comprise at least one genetic modification which decreases activity of a multidrug resistance ATP-binding cassette transporter protein encoded by a PDR5, CDR1 or BFR1 gene.

SEQUENCE DESCRIPTIONS

The various embodiments of the invention can be more fully understood from the following detailed description and the accompanying sequence descriptions, which form a part of this application.

The following sequences conform with 37C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5 (a-bis), and Section 208 and Annex C of the Administrative Instructions). The symbols and format used for nucleotide and amino acid sequence data comply with the rules set forth in 37 C.F.R. §1.822.

TABLE 1

Summary of Coding Region and Protein SEQ ID Numbers for 1-Butanol Biosynthetic Pathway

| Description | SEQ ID NO: Nucleic acid | SEQ ID NO: Peptide |
|---|---|---|
| Acetyl-CoA acetyltransferase thlA from *Clostridium acetobutylicum* ATCC 824 | 1 | 2 |
| Acetyl-CoA acetyltransferase thlB from *Clostridium acetobutylicum* ATCC 824 | 3 | 4 |
| Acetyl-CoA acetyltransferase from *Saccharomyces cerevisiae* | 39 | 40 |
| 3-Hydroxybutyryl-CoA dehydrogenase from *Clostridium acetobutylicum* ATCC 824 | 5 | 6 |
| Crotonase from *Clostridium acetobutylicum* ATCC 824 | 7 | 8 |
| Putative trans-enoyl CoA reductase from *Clostridium acetobutylicum* ATCC 824 | 9 | 10 |
| Butyraldehyde dehydrogenase from *Clostridium beijerinckii* NRRL B594 | 11 | 12 |
| 1-Butanol dehydrogenase bdhB from *Clostridium acetobutylicum* ATCC 824 | 13 | 14 |
| 1-Butanol dehydrogenase bdhA from *Clostridium acetobutylicum* ATCC 824 | 15 | 16 |

TABLE 2

Summary of Coding Region and Protein SEQ ID Numbers for 2-Butanol Biosynthetic Pathway

| Description | SEQ ID NO: Nucleic acid | SEQ ID NO: Peptide |
|---|---|---|
| budA, acetolactate decarboxylase from *Klebsiella pneumoniae* ATCC 25955 | 17 | 18 |
| budB, acetolactate synthase from *Klebsiella pneumoniae* ATCC 25955 | 19 | 20 |
| budC, butanediol dehydrogenase from *Klebsiella pneumoniae* IAM1063 | 21 | 22 |
| pddA, butanediol dehydratase alpha subunit from *Klebsiella oxytoca* ATCC 8724 | 23 | 24 |
| pddB, butanediol dehydratase beta subunit from *Klebsiella oxytoca* ATCC 8724 | 25 | 26 |
| pddC, butanediol dehydratase gamma subunit from *Klebsiella oxytoca* ATCC 8724 | 27 | 28 |
| sadH, 2-butanol dehydrogenase from *Rhodococcus ruber* 219 | 29 | 30 |

TABLE 3

Summary of Coding Region and Protein SEQ ID Numbers for Isobutanol Biosynthetic Pathway

| Description | SEQ ID NO: Nucleic acid | SEQ ID NO: Peptide |
|---|---|---|
| *Klebsiella pneumoniae* budB (acetolactate synthase) | 19 | 20 |
| *Bacillus subtilis* alsS (acetolactate synthase) | 41 | 42 |

TABLE 3-continued

Summary of Coding Region and Protein SEQ ID Numbers for Isobutanol Biosynthetic Pathway

| Description | SEQ ID NO: Nucleic acid | SEQ ID NO: Peptide |
|---|---|---|
| *E. coli* ilvC (acetohydroxy acid reductoisomerase) | 31 | 32 |
| *S. cerevisiae* ILV5 (acetohydroxy acid reductoisomerase) | 43 | 44 |
| *B. subtilis* ilvC (acetohydroxy acid reductoisomerase) | 45 | 46 |
| *E. coli* ilvD (acetohydroxy acid dehydratase) | 33 | 34 |
| *S. cerevisiae* ILV3 (Dihydroxyacid dehydratase) | 47 | 48 |
| *Lactococcus lactis* kivD (branched-chain α-keto acid decarboxylase), codon optimized | 35 | 36 |
| *E. coli* yqhD (branched-chain alcohol dehydrogenase) | 37 | 38 |

TABLE 4

Summary of SEQ ID Numbers for multidrug resistance ATP-binding cassette transporters

| Organism | SEQ ID NO: Nucleic acid | SEQ ID NO: Peptide |
|---|---|---|
| PDR5 of *Saccharomyces cerevisiae* | 49 | 50 |
| CDR1 of *Candida albicans* | 51 | 52 |
| CDR1 of *Candida glabrata* | 53 | 54 |
| CDR1 of *Pichia stipitis* | 55 | 56 |
| CDR1 of *Debaryomyces hansenii* | 57 | 58 |
| Bfr1 of *Schizosaccharomyces pombe* | 59 | 60 |

SEQ ID NO:61 is the nucleotide sequence of the CUP1 promoter.

SEQ ID NO:62 is the nucleotide sequence of the CYC1 terminator.

SEQ ID NO:63 is the nucleotide sequence of the FBA promoter.

SEQ ID NO:64 is the nucleotide sequence of the ADH1 terminator.

SEQ ID NO:65 is the nucleotide sequence of the GPM promoter.

DETAILED DESCRIPTION

The present invention relates to recombinant yeast cells that are engineered for production of butanol and that additionally are engineered to have decreased activity of a protein encoded by the PDR5 gene (Pdr5p). These yeast cells have increased tolerance to butanol and may be used for production of butanol which is valuable as a fuel or fuel additive to reduce demand for fossil fuels.

The following abbreviations and definitions will be used for the interpretation of the specification and the claims.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value The term "butanol" as used herein, refers to 1-butanol, 2-butanol, isobutanol, or mixtures thereof.

The terms "butanol tolerant yeast cell" and "tolerant" when used to describe a modified yeast cell of the invention, refers to a modified yeast that shows better growth in the presence of butanol than the parent strain from which it is derived.

The term "butanol biosynthetic pathway" refers to an enzyme pathway to produce 1-butanol, 2-butanol, or isobutanol.

The term "1-butanol biosynthetic pathway" refers to an enzyme pathway to produce 1-butanol from acetyl-coenzyme A (acetyl-CoA).

The term "2-butanol biosynthetic pathway" refers to an enzyme pathway to produce 2-butanol from pyruvate.

The term "isobutanol biosynthetic pathway" refers to an enzyme pathway to produce isobutanol from pyruvate.

The term "PDR5" refers to a gene encoding a protein that is a multidrug ATP-binding cassette (ABC) transporter, also called a multidrug efflux pump, that has been identified in *Saccharomyces cerevisiae*. The PDR initials stand for Pleiotropic Drug Resistance. The PDR5 encoded protein Pdr5p is a is designated TC#3.A.1.205.1 in the transporter classification system as given by the Transport Classification Database (M. Saier; U of CA, San Diego). Proteins with the same function as Pdr5p encoded by PDR5 may be referred to in the art as being encoded by genes with other names including STS1, YDR1, LEM1 and YOR153W. The term "Pdr5p" refers herein to any of these encoded proteins that functions similarly to Pdr5p and that has sequence identity to a Pdr5p amino acid sequence that is at least about 75%-80%, 80%-85%, 85%-90%, 90%-95%, or 95%-100%. These genes may or may not be endogenous to the yeast cell.

The term "CDR1" refers to a gene encoding a protein that is a multidrug ATP-binding cassette (ABC) transporter and multidrug resistance protein that has been identified in *Candida albicans* and other yeasts. The encoded Cdr1p is designated TC#3.A.1.205.4 in the transporter classification system as given by the Transport Classification Database (M. Saier; U of CA, San Diego). The term Cdr1p refers herein to any protein that functions similarly to Cdr1p of *Candida albicans* and that has sequence identity to a Cdr1p amino acid sequence that is at least about 75%-80%, 80%-85%, 85%-90%, 90%-95%, or 95%-100%.

The term "BFR1" refers to a gene encoding a protein that is a multidrug ATP-binding cassette (ABC) transporter and multidrug resistance protein that has been identified in *Schizosaccharomyces pombe*. The encoded Bfr1p is designated TC#3.A.1.205.11 in the transporter classification system as given by the Transport Classification Database (M. Saier; U of CA, San Diego). The term Bfr1p refers herein to any protein that functions similarly to Bfr1p of *Schizosaccharomyces pombe* and that has sequence identity to *S. pombe* Bfr1p amino acid sequence that is at least about 75%-80%, 80%-85%, 85%-90%, 90%-95%, or 95%-100%.

The term "acetyl-CoA acetyltransferase" refers to an enzyme that catalyzes the conversion of two molecules of acetyl-CoA to acetoacetyl-CoA and coenzyme A (CoA). Preferred acetyl-CoA acetyltransferases are acetyl-CoA acetyltransferases with substrate preferences (reaction in the forward direction) for a short chain acyl-CoA and acetyl-CoA and are classified as E.C. 2.3.1.9 [*Enzyme Nomenclature* 1992, Academic Press, San Diego]; although, enzymes with a broader substrate range (E.C. 2.3.1.16) will be functional as well. Acetyl-CoA acetyltransferases are available from a number of sources, for example, *Escherichia coli* (GenBank Nos: NP_416728, NC_000913; NCBI (National Center for Biotechnology Information) amino acid sequence, NCBI nucleotide sequence), *Clostridium acetobutylicum* (GenBank Nos: NP_349476.1 (SEQ ID NO:2), NC_003030; NP_149242 (SEQ ID NO:4), NC_001988), *Bacillus subtilis* (GenBank Nos: NP_390297, NC_000964), and *Saccharomyces cerevisiae* (GenBank Nos: NP_015297, NC_001148 (SEQ ID NO:39)).

The term "3-hydroxybutyryl-CoA dehydrogenase" refers to an enzyme that catalyzes the conversion of acetoacetyl-CoA to 3-hydroxybutyryl-CoA. 3-Hydroxybutyryl-CoA dehydrogenases may be reduced nicotinamide adenine dinucleotide (NADH)-dependent, with a substrate preference for (S)-3-hydroxybutyryl-CoA or (R)-3-hydroxybutyryl-CoA and are classified as E.C. 1.1.1.35 and E.C. 1.1.1.30, respectively. Additionally, 3-hydroxybutyryl-CoA dehydrogenases may be reduced nicotinamide adenine dinucleotide phosphate (NADPH)-dependent, with a substrate preference for (S)-3-hydroxybutyryl-CoA or (R)-3-hydroxybutyryl-CoA and are classified as E.C. 1.1.1.157 and E.C. 1.1.1.36, respectively. 3-Hydroxybutyryl-CoA dehydrogenases are available from a number of sources, for example, *C. acetobutylicum* (GenBank NOs: NP_349314 (SEQ ID NO:6), NC_003030), *B. subtilis* (GenBank NOs: AAB09614, U29084), *Ralstonia eutropha* (GenBank NOs: ZP_0017144, NZ_AADY01000001, *Alcaligenes eutrophus* (GenBank NOs: YP_294481, NC_007347), and *A. eutrophus* (GenBank NOs: P14697, J04987).

The term "crotonase" refers to an enzyme that catalyzes the conversion of 3-hydroxybutyryl-CoA to crotonyl-CoA and $H_2O$. Crotonases may have a substrate preference for (S)-3-hydroxybutyryl-CoA or (R)-3-hydroxybutyryl-CoA and are classified as E.C. 4.2.1.17 and E.C. 4.2.1.55, respectively. Crotonases are available from a number of sources, for example, *E. coli* (GenBank NOs: NP_415911 (SEQ ID NO:8), NC_000913), *C. acetobutylicum* (GenBank NOs:

NP_349318, NC_003030), *B. subtilis* (GenBank NOs: CAB13705, Z99113), and *Aeromonas caviae* (GenBank NOs: BAA21816, D88825).

The term "butyryl-CoA dehydrogenase", also called trans-enoyl CoA reductase, refers to an enzyme that catalyzes the conversion of crotonyl-CoA to butyryl-CoA. Butyryl-CoA dehydrogenases may be NADH-dependent or NADPH-dependent and are classified as E.C. 1.3.1.44 and E.C. 1.3.1.38, respectively. Butyryl-CoA dehydrogenases are available from a number of sources, for example, *C. acetobutylicum* (GenBank NOs: NP_347102 (SEQ ID NO:10), NC_003030), *Euglena gracilis* (GenBank NOs: Q5EU90, AY741582), *Streptomyces collinus* (Gen Bank NOs: AAA92890, U37135), and *Streptomyces coelicolor* (GenBank NOs: CAA22721, AL939127).

The term "butyraldehyde dehydrogenase" refers to an enzyme that catalyzes the conversion of butyryl-CoA to butyraldehyde, using NADH or NADPH as cofactor. Butyraldehyde dehydrogenases with a preference for NADH are known as E.C. 1.2.1.57 and are available from, for example, *Clostridium beijerinckii* (GenBank NOs: AAD31841 (SEQ ID NO:12), AF157306) and *C. acetobutylicum* (GenBank NOs: NP_149325, NC_001988).

The term "1-butanol dehydrogenase" refers to an enzyme that catalyzes the conversion of butyraldehyde to 1-butanol. 1-butanol dehydrogenases are a subset of the broad family of alcohol dehydrogenases. 1-butanol dehydrogenase may be NADH- or NADPH-dependent. 1-butanol dehydrogenases are available from, for example, *C. acetobutylicum* (GenBank NOs: NP_149325, NC_001988; NP_349891 (SEQ ID NO:14), NC_003030; and NP_349892 (SEQ ID NO:16), NC_003030) and *E. coli* (GenBank NOs: NP_417484, NC_000913).

The term "acetolactate synthase", also known as "acetohydroxy acid synthase", refers to a polypeptide (or polypeptides) having an enzyme activity that catalyzes the conversion of two molecules of pyruvic acid to one molecule of alpha-acetolactate. Acetolactate synthase, known as EC 2.2.1.6 [formerly 4.1.3.18] (*Enzyme Nomenclature* 1992, Academic Press, San Diego) may be dependent on the cofactor thiamin pyrophosphate for its activity. Suitable acetolactate synthase enzymes are available from a number of sources, for example, *Bacillus subtilis* (GenBank Nos: AAA22222 NCBI (National Center for Biotechnology Information) amino acid sequence (SEQ ID NO:42), L04470 NCBI nucleotide sequence (SEQ ID NO:41)), *Klebsiella terrigena* (GenBank Nos: AAA25055, L04507), and *Klebsiella pneumoniae* (GenBank Nos: AAA25079 (SEQ ID NO:20), M73842 (SEQ ID NO:19).

The term "acetolactate decarboxylase" refers to a polypeptide (or polypeptides) having an enzyme activity that catalyzes the conversion of alpha-acetolactate to acetoin. Acetolactate decarboxylases are known as EC 4.1.1.5 and are available, for example, from *Bacillus subtilis* (GenBank Nos: AAA22223, L04470), *Klebsiella terrigena* (GenBank Nos: AAA25054, L04507) and *Klebsiella pneumoniae* (SEQ ID NO:18 (amino acid) SEQ ID NO:17 (nucleotide)).

The term "butanediol dehydrogenase" also known as "acetoin reductase" refers to a polypeptide (or polypeptides) having an enzyme activity that catalyzes the conversion of acetoin to 2,3-butanediol. Butanediol dehydrogenases are a subset of the broad family of alcohol dehydrogenases. Butanediol dehydrogenase enzymes may have specificity for production of R- or S-stereochemistry in the alcohol product. S-specific butanediol dehydrogenases are known as EC 1.1.1.76 and are available, for example, from *Klebsiella pneumoniae* (GenBank Nos: BBA13085 (SEQ ID NO:22), D86412. R-specific butanediol dehydrogenases are known as EC 1.1.1.4 and are available, for example, from *Bacillus cereus* (GenBank Nos. NP_830481, NC_004722; AAP07682, AE017000), and *Lactococcus lactis* (GenBank Nos. AAK04995, AE006323).

The term "butanediol dehydratase", also known as "diol dehydratase" or "propanediol dehydratase" refers to a polypeptide (or polypeptides) having an enzyme activity that catalyzes the conversion of 2,3-butanediol to 2-butanone, also known as methyl ethyl ketone (MEK). Butanediol dehydratase may utilize the cofactor adenosyl cobalamin. Adenosyl cobalamin-dependent enzymes are known as EC 4.2.1.28 and are available, for example, from *Klebsiella oxytoca* (GenBank Nos: BAA08099 (alpha subunit) (SEQ ID NO:24), BAA08100 (beta subunit) (SEQ ID NO:26), and BBA08101 (gamma subunit) (SEQ ID NO:28), (Note all three subunits are required for activity), D45071).

The term "2-butanol dehydrogenase" refers to a polypeptide (or polypeptides) having an enzyme activity that catalyzes the conversion of 2-butanone to 2-butanol. 2-butanol dehydrogenases are a subset of the broad family of alcohol dehydrogenases. 2-butanol dehydrogenase may be NADH- or NADPH-dependent. The NADH-dependent enzymes are known as EC 1.1.1.1 and are available, for example, from *Rhodococcus ruber* (GenBank Nos: CAD36475 (SEQ ID NO:30), AJ491307 (SEQ ID NO:29)). The NADPH-dependent enzymes are known as EC 1.1.1.2 and are available, for example, from *Pyrococcus furiosus* (GenBank Nos: AAC25556, AF013169).

The term "acetohydroxy acid isomeroreductase" or "acetohydroxy acid reductoisomerase" refers to an enzyme that catalyzes the conversion of acetolactate to 2,3-dihydroxyisovalerate using NADPH (reduced nicotinamide adenine dinucleotide phosphate) as an electron donor. Preferred acetohydroxy acid isomeroreductases are known by the EC number 1.1.1.86 and sequences are available from a vast array of microorganisms, including, but not limited to, *Escherichia coli* (GenBank Nos: NP_418222 (SEQ ID NO:32), NC_000913 (SEQ ID NO:31)), *Saccharomyces cerevisiae* (GenBank Nos: NP_013459 (SEQ ID NO:44), NC_001144 (SEQ ID NO:43)), *Methanococcus maripaludis* (GenBank Nos: CAF30210, BX957220), and *Bacillus subtilis* (GenBank Nos: CAB14789 (SEQ ID NO:46), Z99118 (SEQ ID NO:45)).

The term "acetohydroxy acid dehydratase" or "dihydroxy acid dehydratase" refers to an enzyme that catalyzes the conversion of 2,3-dihydroxyisovalerate to α-ketoisovalerate. Preferred acetohydroxy acid dehydratases are known by the EC number 4.2.1.9. These enzymes are available from a vast array of microorganisms, including, but not limited to, *E. coli* (GenBank Nos: YP_026248 (SEQ ID NO:34), NC_000913 (SEQ ID NO:33)), *S. cerevisiae* (GenBank Nos: NP_012550 (SEQ ID NO:48), NC_001142 (SEQ ID NO:47)), *M. maripaludis* (GenBank Nos: CAF29874, BX957219), and *B. subtilis* (GenBank Nos: CAB14105, Z99115).

The term "branched-chain α-keto acid decarboxylase" refers to an enzyme that catalyzes the conversion of α-ketoisovalerate to isobutyraldehyde and $CO_2$. Preferred branched-chain α-keto acid decarboxylases are known by the EC number 4.1.1.72 and are available from a number of sources, including, but not limited to, *Lactococcus lactis* (GenBank Nos: AAS49166, AY548760; CAG34226 (SEQ ID NO:36), AJ746364, *Salmonella typhimurium* (GenBank Nos: NP_461346, NC_003197), and *Clostridium acetobutylicum* (GenBank Nos: NP_149189, NC_001988).

The term "branched-chain alcohol dehydrogenase" refers to an enzyme that catalyzes the conversion of isobutyraldehyde to isobutanol. Preferred branched-chain alcohol dehydrogenases are known by the EC number 1.1.1.265, but may also be classified under other alcohol dehydrogenases (specifically, EC 1.1.1.1 or 1.1.1.2). These enzymes utilize NADH (reduced nicotinamide adenine dinucleotide) and/or NADPH as electron donor and are available from a number of sources, including, but not limited to, *S. cerevisiae* (GenBank Nos: NP_010656, NC_001136; NP_014051, NC_001145), *E. coli* (GenBank Nos: NP_417484 (SEQ ID NO:38), NC_000913 (SEQ ID NO:37)), and *C. acetobutylicum* (GenBank Nos: NP_349892, NC_003030).

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein the term "coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

The term "reduced activity" as it applies to the expression of a protein in a cell host will include those situations where the activity of the protein is diminished as compared with a wildtype form (as with antisense technology for example) or substantially eliminated as with gene disruption, deletion or inactivation for example.

As used herein the term "transformation" refers to the transfer of a nucleic acid fragment into a host organism, resulting in genetically stable inheritance. Host organisms containing the transformed nucleic acid fragments are referred to as "transgenic" or "recombinant" or "transformed" organisms.

The terms "plasmid" and "vector" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation vector" refers to a specific vector containing a foreign gene and having elements in addition to the foreign gene that facilitates transformation of a particular host cell.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.*, 215: 403-410 (1993)). In general, a sequence of ten or more contiguous amino acids or thirty or more nucleotides is necessary in order to identify putatively a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

As used herein, "substantially similar" enzymes will refer to enzymes belonging to a family of proteins in the art known to share similar structures and function. It is well within the skill of one in the art to identify substantially similar proteins given a known structure. Typical methods to identify substantially similar structures will rely upon known sequence information (nucleotide sequence and/or amino acid sequences) and may include PCR amplification, nucleic acid hybridization, and/or sequence identity/similarity analysis (e.g., sequence alignments between partial and/or complete sequences and/or known functional motifs associated with the desired activity).

A nucleic acid molecule is "hybridizable" to another nucleic acid molecule, such as a cDNA, genomic DNA, or RNA molecule, when a single-stranded form of the nucleic acid molecule can anneal to the other nucleic acid molecule under the appropriate conditions of temperature and solution ionic strength. Given the nucleic acid sequences described herein, one of skill in the art can identify substantially similar nucleic acid fragments that may encode proteins having similar activity. Hybridization and washing conditions are well known and exemplified in Sambrook, J., Fritsch, E. F. and Maniatis, T. *Molecular Cloning: A Laboratory Manual,* 3rd ed., Cold Spring Harbor Laboratory: Cold Spring Harbor, N.Y. (2001), particularly Chapter 11 and Table 11.1 therein. The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS at 65° C. followed by 0.1×SSC, 0.1% SDS at 65° C., for example.

In one aspect, suitable nucleic acid fragments encode polypeptides that are at least about 70% identical to the amino acid sequences reported herein. In another aspect, the nucleic acid fragments encode amino acid sequences that are about 85-90% identical to the amino acid sequences reported herein. In a further aspect, the nucleic acid fragments encode amino acid sequences that are at least about 90-100% identical to the amino acid sequences reported herein. Suitable nucleic acid fragments not only have the above homologies but typically encode a polypeptide having at least about 50 amino acids, preferably at least about 100 amino acids, more preferably at least about 150 amino acids, still more preferably at least about 200 amino acids, and most preferably at least about 250 amino acids.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences is performed using the Clustal method of alignment (Higgins and Sharp, *CABIOS.* 5:151-153 (1989)) with default parameters (GAP PENALTY=10, GAP LENGTH PENALTY=10), unless otherwise specified. Default parameters for pairwise alignments using the Clustal method are: KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 75% identical, and more preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "homology" refers to the relationship among sequences whereby there is some extent of likeness, typically due to descent from a common ancestral sequence. Homologous sequences can share homology based on genic, structural, functional and/or behavioral properties. The term "ortholog" or "orthologous sequences" refers herein to a relationship where sequence divergence follows speciation (i.e., homologous sequences in different species arose from a common ancestral gene during speciation). In contrast, the term "paralogous" refers to homologous sequences within a single species that arose by gene duplication. One skilled in the art will be familiar with techniques required to identify homologous, orthologous and paralogous sequences.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.*, 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein, "default values" will mean any set of values or parameters (as set by the software manufacturer) which originally load with the software when first initialized Standard recombinant DNA and molecular cloning techniques used here are well known in the art and are described by Sambrook, J., Fritsch, E. F. and Maniatis, T. *Molecular Cloning: A Laboratory Manual*, 2$^{nd}$ ed.; Cold Spring Harbor Laboratory: Cold Spring Harbor, N.Y., 1989 (hereinafter "Maniatis"); and by Silhavy, T. J., Bennan, M. L. and Enquist, L. W. Experiments with Gene Fusions; Cold Spring Harbor Laboratory: Cold Spring Harbor, N.Y., 1984; and by Ausubel, F. M. et al., In *Current Protocols in Molecular Biology*, published by Greene Publishing and Wiley-Interscience, 1987.

Butanol Tolerance

The invention relates to the discovery that strains of *Saccharomyces cerevisiae* that are engineered to have a PDR5 gene deletion have increased butanol tolerance. About twenty strains of *Saccharomyces cerevisiae* having deletions of different genes were tested for increased butanol tolerance. The tested strains included those with deletions in different efflux transporters. From this testing it was found that the most improvement in butanol tolerance was in a strain in which the deletion was of the PDR5 gene.

The PDR5 gene encodes a protein (Pdr5p: coding region SEQ ID NO:49 and protein SEQ ID NO:50) that is an ATP-binding cassette (ABC) transporter. Pdr5p has efflux pump activity that mediates resistance to many xenobiotic compounds including mutagens, fungicides, steroids, and anticancer drugs. In addition to drug response, Pdr5p is also involved in cation resistance and lipid translocation. Overexpression of Pdr5p results in multidrug resistance (MDR). Loss-of-function mutations in PDR5 create hypersensitivity to a large array of chemically diverse inhibitors because of an inability to cause efflux of such compounds. The finding herein that PDR5 deletion confers increased tolerance to butanol seems to be an opposite effect to this hypersensitive drug response.

In other types of yeasts ATP-binding cassette (ABC) transporters with multidrug resistance conferring properties are encoded by genes named CDR1 and BFR1. For example, CDR1 is present in *Candida albicans* (coding region SEQ ID NO:51, protein SEQ ID NO:52), *Candida glabrata* (coding region SEQ ID NO:53, protein SEQ ID NO:54), *Pichia stipitis* (coding region SEQ ID NO:55, protein SEQ ID NO:56), and *Degaryomces hansenii* (coding region SEQ ID NO:57, protein SEQ ID NO:58). For example, BFR1 is present in *Schizosaccharomyces pombe* (coding region SEQ ID NO:59, protein SEQ ID NO:60).

Reducing or substantially eliminating the activity of protein encoded by the gene endogenous to a yeast cell that may be PDR5, CDR1, or BFR1 and that functions as an ATP-binding cassette (ABC) transporter may be used to increase butanol tolerance of the cell. In yeast cells with a genetic modification that inactivates the endogenous PDR5 gene, improved butanol tolerance may be measured through growth yield. Improved growth yield in the presence of butanol varies with the concentration and type of butanol in the growth medium. For example, in 0.625% (w/v) 1-butanol growth yield was 1.4 fold compared to that of the parental non-deleted cells, while in 0.75% (w/v) isobutanol growth yield was 2.7 fold compared to that of the parental non-deleted cells. These results were for a diploid strain. In a haploid yeast grown in 0.75% (w/v) isobutanol, growth yield was 1.8 fold compared to that of the parental non-deleted cells.

Yeast Cells with Reduced Expression of Endogenous ATP-Binding Cassette (ABC) Transporter Pdr5p, Cdr1p or Bfr1p Reduced expression of the endogenous PDR5, CDR1, or BFR1 gene to confer reduced Pdr5p, Cdr1p, or Bfr1p activity, respectively, may be engineered in any yeast cell that is amenable to genetic manipulation. Examples include yeasts of *Saccharomyces, Schizosaccharomyces, Hansenula, Candida, Kluyveromyces, Yarrowia* and *Pichia*. Suitable strains include, but are not limited to, *Saccharomyces cerevisiae, Schizosaccharomyces pombe, Kluyveromyces lactis, Kluyveromyces thermotolerans, Candida glabrata, Candida albicans, Pichia stipitis* and *Yarrowia lipolytica*. Particularly suitable is *Saccharomyces cerevisiae*.

In any yeast cell, an endogenous PDR5, CDR1, or BFR1 gene, or gene encoding a protein with the same function as the proteins encoded by these genes, may be a target for reduced expression. A gene encoding a protein that performs the same function as Pdr5p encoded by PDR5 may be referred to in the art as a gene with another name including STS1, YDR1, LEM1 and YOR153W. In referring to PDR5 and Pdr5p herein are included genes and their encoded proteins such as these with the same function and high sequence identities. Examples of target genes are those encoding Pdr5p from *Saccharomyces cerevisiae* (coding region SEQ ID NO:49; protein SEQ ID NO:50), Cdr1p from *Candida albicans* (coding region SEQ ID NO:51, protein SEQ ID NO:52), *Candida glabrata* (coding region SEQ ID NO:53, protein SEQ ID NO:54), *Pichia stipitis* (coding region SEQ ID NO:55, protein SEQ ID NO:56), and *Degaryomces hansenii* (coding region SEQ ID NO:57, protein SEQ ID NO:58), and BFR1 from *Schizosaccharomyces pombe* (coding region SEQ ID NO:59, protein SEQ ID NO:60).

Because the sequences of PDR5, CDR1, and BFR1 coding regions and the encoded ABC transporter proteins are known, as exemplified in the SEQ ID NOs listed above and given in Table 4, suitable Pdr5p, Cdr1p, and Bfr1p proteins and their encoding regions may be readily identified by one skilled in the art on the basis of sequence similarity using bioinformatics approaches. Typically BLAST (described above) searching of publicly available databases with known Pdr5p, Cdr1p, or Bfr1p amino acid sequences, such as those provided herein, is used to identify other Pdr5ps, Cdr1ps, or Bfr1ps and their encoding sequences, that may be used as targets in the present strains. These proteins may have at least about 75%-80%, 80-85%, 85%-90%, 90%-95% or 95%-99% sequence identity to any of the Pdr5ps, Cdr1ps or Bfr1p of SEQ ID NOS:50, 52, 54, 56, 58, or 60 while having multidrug resistance ABC transporter activity. Identities are based on the Clustal W method of alignment using the default parameters of GAP PENALTY=10, GAP LENGTH PENALTY=0.1, and Gonnet 250 series of protein weight matrix.

In addition to using protein or coding region sequence and bioinformatics methods to identify additional target genes, the sequences described herein or those recited in the art may be used to experimentally identify other homologs in nature. For example each of the of Pdr5p, Cdr1p, or Bfr1p encoding nucleic acid fragments described herein may be used to isolate genes encoding homologous proteins. Isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci. USA* 82:1074 (1985); or strand displacement amplification (SDA), Walker, et al., *Proc. Natl. Acad. Sci. U.S.A.*, 89:392 (1992)]; and 3.) methods of library construction and screening by complementation.

For example, genes encoding similar proteins or polypeptides to the Pdr5p, Cdr1p or Bfr1p encoding genes described herein could be isolated directly by using all or a portion of the instant nucleic acid fragments as DNA hybridization probes to screen libraries from any desired organism using methodology well known to those skilled in the art. Specific oligonucleotide probes based upon the disclosed nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments by hybridization under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotides as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the described sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the described nucleic acid fragments, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., PNAS USA 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (e.g., BRL, Gaithersburg, Md.), specific 3' or 5' cDNA fragments can be isolated (Ohara et al., *PNAS USA* 86:5673 (1989); Loh et al., *Science* 243:217 (1989)).

Alternatively, the described Pdr5p, Cdr1p, or Bfr1p encoding sequences may be employed as hybridization reagents for the identification of homologs. The basic components of a nucleic acid hybridization test include a probe, a sample suspected of containing the gene or gene fragment of interest, and a specific hybridization method. Probes are typically single-stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143-5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide and cesium trifluoroacetate, among others. Typically, the chaotropic agent will be present at a final concentration of about 3 M. If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal) and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

At least one gene encoding Pdr5p, Cdr1p, or Bfr1p may be disrupted in any yeast cell to decrease or substantially eliminate the Pdr5p, Cdr1p, or Bfr1p activity using genetic modification. Many methods for genetic modification of target genes are known to one skilled in the art and may be used to create the present yeast strains. Modifications that may be used to reduce or substantially eliminate expression of a target protein are disruptions that include, but are not limited to, deletion of the entire gene or a portion of the gene, inserting a DNA fragment into the gene (in either the promoter or coding region) so that the protein is not expressed or expressed at lower levels, introducing a mutation into the coding region which adds a stop codon or frame shift such that a functional protein is not expressed, and introducing one or more mutations into the coding region to alter amino acids so that a non-functional or a less enzymatically active protein is expressed. In addition, expression of a gene may be blocked by expression of an antisense RNA or an interfering RNA, and constructs may be introduced that result in cosuppression. In addition, the synthesis or stability of the transcript may be lessened by mutation. Similarly the efficiency by which a protein is translated from mRNA may be modulated by mutation. All of these methods may be readily practiced by one skilled in the art making use of the known or identified coding sequences of the target PDR5, CDR1, or BFR1 gene. DNA sequences surrounding coding sequence of the target gene are also useful in some modification procedures and are available for yeasts such as for *Saccharomyces cerevisiae* in the complete genome sequence coordinated by Genome Project ID9518 of Genome Projects coordinated by NCBI (National Center for Biotechnology Information) with identifying GOPID 13838. Additional examples of yeast genomic sequences include that of *Yarrowia lipolytica*, GOPIC 13837, and of *Candida albicans*, which is included in GPID 10771, 10701 and 16373. Additional genomes have been completely sequenced and annotated and are publicly available for the following yeast strains: *Candida glabrata* CBS 138, *Kluyveromyces lactis* NRRL Y-1140, *Pichia stipitis* CBS 6054, and *Schizosaccharomyces pombe* 972h-.

In particular, DNA sequences surrounding a target coding sequence are useful for modification methods using homologous recombination. For example, in this method flanking sequences are placed bounding a selectable marker gene to mediate homologous recombination whereby the marker gene replaces the target gene. Also partial target gene sequences and flanking sequences bounding a selectable marker gene may be used to mediate homologous recombination whereby the marker gene replaces a portion of the target gene. In addition, the selectable marker may be bounded by site-specific recombination sites, so that following expression of the corresponding site-specific recombinase, the resistance gene is excised from the target gene without reactivating the latter. The site-specific recombination leaves behind a recombination site which disrupts expression of the target gene encoded protein. The homologous recombination vector may be constructed to also leave a deletion in the target gene following excision of the selectable marker, as is well known to one skilled in the art.

Deletions may be made using mitotic recombination as described in Wach et al. ((1994) Yeast 10:1793-1808). This method involves preparing a DNA fragment that contains a selectable marker between genomic regions that may be as short as 20 bp, and which bound a target DNA sequence. This DNA fragment can be prepared by PCR amplification of the selectable marker gene using as primers oligonucleotides that hybridize to the ends of the marker gene and that include the genomic regions that can recombine with the yeast genome. The linear DNA fragment can be efficiently transformed into yeast and recombined into the genome resulting in gene replacement including with deletion of the target DNA sequence (as described in Methods in Enzymology, v 194, pp 281-301 (1991)).

Moreover, promoter replacement methods may be used to exchange the endogenous transcriptional control elements allowing another means to modulate expression such as described in Mnaimneh et al. ((2004) Cell 118(1):31-44) and in Example 12 herein.

In addition, a target gene in any yeast cell may be disrupted using random mutagenesis, which is followed by screening to identify strains with reduced target gene encoded activity. Using this type of method, the DNA sequence of a PDR5, CDR1, or BFR1 gene, or any other region of the genome affecting expression of the target gene, need not be known.

Methods for creating genetic mutations are common and well known in the art and may be applied to the exercise of creating mutants. Commonly used random genetic modification methods (reviewed in *Methods in Yeast Genetics*, 2005, Cold Spring Harbor Laboratory Press, Cold Spring Harbor, N.Y.) include spontaneous mutagenesis, mutagenesis caused by mutator genes, chemical mutagenesis, irradiation with UV or X-rays, or transposon mutagenesis.

Chemical mutagenesis of yeast commonly involves treatment of yeast cells with one of the following DNA mutagens: ethyl methanesulfonate (EMS), nitrous acid, diethyl sulfate, or N-methyl-N'-nitro-N-nitroso-guanidine (MNNG). These methods of mutagenesis have been reviewed in Spencer et al (Mutagenesis in Yeast, 1996, *Yeast Protocols: Methods in Cell and Molecular Biology*. Humana Press, Totowa, N.J.). Chemical mutagenesis with EMS may be performed as described in *Methods in Yeast Genetics*, 2005, Cold Spring Harbor Laboratory Press, Cold Spring Harbor, N.Y. Irradiation with ultraviolet (UV) light or X-rays can also be used to produce random mutagenesis in yeast cells. The primary effect of mutagenesis by UV irradiation is the formation of pyrimidine dimers which disrupt the fidelity of DNA replication. Protocols for UV-mutagenesis of yeast can be found in Spencer et al (Mutagenesis in Yeast, 1996, *Yeast Protocols: Methods in Cell and Molecular Biology*. Humana Press, Totowa, N.J.). Introduction of a mutator phenotype can also be used to generate random chromosomal mutations in yeast. Common mutator phenotypes can be obtained through disruption of one or more of the following genes: PMS1, MAG1, RAD18 or RAD51. Restoration of the non-mutator phenotype can be easily obtained by insertion of the wildtype allele. Collections of modified cells produced from any of these or other known random mutagenesis processes may be screened for reduced Pdr5p activity.

In addition, transcription factors regulating PDR5, CDR1, or BFR1 expression may be altered to decrease Pdr5p, Cdr1p, or Bfr1p activity. For example, PDR5 expression is positively regulated by transcription factors Pdr1p and Pdr3p. Decreasing function of these transcription factors may be used to decrease PDR5 expression. PDR5 expression is negatively regulated by transcription factor Rdr1p, and increased function of this transcription factor may be used to decrease PDR5 expression.

Butanol Biosynthetic Pathway

In the present invention, a genetic modification conferring increased butanol tolerance, as described above, is engineered in a yeast cell that is engineered to express a butanol biosynthetic pathway. Either genetic modification may take place prior to the other. The butanol biosynthetic pathway may be a 1-butanol, 2-butanol, or isobutanol biosynthetic pathway.

Suitable biosynthetic pathways are known in the art, and certain suitable pathways are described herein. In some embodiments, the butanol biosynthetic pathway comprises at least one gene that is heterologous to the yeast cell. In some embodiments, the butanol biosynthetic pathway comprises more than one gene that is heterologous to the yeast cell. In some embodiments, the butanol biosynthetic pathway comprises heterologous genes encoding polypeptides corresponding to every step of a biosynthetic pathway.

Likewise, certain suitable proteins having the ability to catalyze the indicated substrate to product conversions are described herein and other suitable proteins are described in the art. For example, US Published Patent Application Nos. US20080261230 and US20090163376, incorporated herein by reference, describe acetohydroxy acid isomeroreductases; U.S. patent application Ser. No. 12/569,636, incorporated by reference, describes dihydroxyacid dehydratases; an alcohol dehydrogenase is described in US Published Patent Application US20090269823, incorporated herein by reference.

1-Butanol Biosynthetic Pathway

A biosynthetic pathway for the production of 1-butanol that may be used is described by Donaldson et al. in copending and commonly owned U.S. Patent Application Publication No. US20080182308A1, incorporated herein by reference. This biosynthetic pathway comprises the following substrate to product conversions:
a) acetyl-CoA to acetoacetyl-CoA, as catalyzed for example by acetyl-CoA acetyltransferase with protein sequence such as SEQ ID NO:2, 4 or 40 encoded by the genes given as SEQ ID NO:1, 3 or 39;
b) acetoacetyl-CoA to 3-hydroxybutyryl-CoA, as catalyzed for example by 3-hydroxybutyryl-CoA dehydrogenase with protein sequence such as SEQ ID NO:6 encoded by the gene given as SEQ ID NO:5;
c) 3-hydroxybutyryl-CoA to crotonyl-CoA, as catalyzed for example by crotonase with protein sequence such as SEQ ID NO:8 encoded by the gene given as SEQ ID NO:7;
d) crotonyl-CoA to butyryl-CoA, as catalyzed for example by butyryl-CoA dehydrogenase with protein sequence such as SEQ ID NO:10 encoded by the gene given as SEQ ID NO:9;
e) butyryl-CoA to butyraldehyde, as catalyzed for example by butyraldehyde dehydrogenase with protein sequence such as SEQ ID NO:12 encoded by the gene given as SEQ ID NO:11; and
f) butyraldehyde to 1-butanol, as catalyzed for example by 1-butanol dehydrogenase with protein sequence such as SEQ ID NO:14 or 16 encoded by the genes given as SEQ ID NO:13 or 15.

The pathway requires no ATP and generates NAD+ and/or NADP+, thus, it balances with the central, metabolic routes that generate acetyl-CoA. In some embodiments, the 1-butanol biosynthetic pathway comprises at least one gene, at least two genes, at least three genes, at least four genes, or at least five genes that is/are heterologous to the yeast cell.

2-Butanol Biosynthetic Pathway

Biosynthetic pathways for the production of 2-butanol that may be used are described by Donaldson et al. in co-pending and commonly owned U.S. Patent Application Publication Nos. US20070259410A1 and US 20070292927A1, each incorporated herein by reference. One 2-butanol biosynthetic pathway comprises the following substrate to product conversions:
a) pyruvate to alpha-acetolactate, as catalyzed for example by acetolactate synthase with protein sequence such as SEQ ID NO:20 encoded by the gene given as SEQ ID NO:19;
b) alpha-acetolactate to acetoin, as catalyzed for example by acetolactate decarboxylase with protein sequence such as SEQ ID NO:18 encoded by the gene given as SEQ ID NO:17;
c) acetoin to 2,3-butanediol, as catalyzed for example by butanediol dehydrogenase with protein sequence such as SEQ ID NO:22 encoded by the gene given as SEQ ID NO:21;
d) 2,3-butanediol to 2-butanone, catalyzed for example by butanediol dehydratase with protein sequence such as SEQ ID NO:24, 26, or 28 encoded by genes given as SEQ ID NO:23, 25, or 27; and
e) 2-butanone to 2-butanol, as catalyzed for example by 2-butanol dehydrogenase with protein sequence such as SEQ ID NO:30 encoded by the gene given as SEQ ID NO:29.

In some embodiments, the 2-butanol biosynthetic pathway comprises at least one gene, at least two genes, at least three genes, or at least four genes that is/are heterologous to the yeast cell.

Isobutanol Biosynthetic Pathway

Biosynthetic pathways for the production of isobutanol that may be used are described by Maggio-Hall et al. in copending and commonly owned U.S. Patent Application Publication No. US20070092957 A1, incorporated herein by reference. One isobutanol biosynthetic pathway comprises the following substrate to product conversions:
a) pyruvate to acetolactate, as catalyzed for example by acetolactate synthase with protein sequence such as SEQ ID NO:20 or 42 encoded by genes given as SEQ ID NO:19 or 41;
b) acetolactate to 2,3-dihydroxyisovalerate, as catalyzed for example by acetohydroxy acid isomeroreductase with protein sequence such as SEQ ID NO:32, 44 or 46 encoded by genes given as SEQ ID NO:31, 43 or 45;
c) 2,3-dihydroxyisovalerate to α-ketoisovalerate, as catalyzed for example by acetohydroxy acid dehydratase with protein sequence such as SEQ ID NO:34 encoded by the gene given as SEQ ID NO:33; or dihydroxyacid dehydratase with protein sequence such as SEQ ID NO:48 encoded by the gene given as SEQ ID NO:47;
d) α-ketoisovalerate to isobutyraldehyde, as catalyzed for example by a branched-chain keto acid decarboxylase with protein sequence such as SEQ ID NO:36 encoded by the gene given as SEQ ID NO:35; and
e) isobutyraldehyde to isobutanol, as catalyzed for example by a branched-chain alcohol dehydrogenase with protein sequence such as SEQ ID NO:38 encoded by the gene given as SEQ ID NO:37.

In some embodiments, the isobutanol biosynthetic pathway comprises at least one gene, at least two genes, at least three genes, or at least four genes that is/are heterologous to the yeast cell.

Construction of Yeast Strains for Butanol Production

Any yeast strain that is genetically modified for butanol tolerance as described herein is additionally genetically modified (before or after modification to tolerance) to incorporate a butanol biosynthetic pathway by methods well known to one skilled in the art. Genes encoding the enzyme activities described above, or homologs that may be identified and obtained by commonly used methods, such as those described above, that are well known to one skilled in the art, are introduced into a yeast host. Representative coding and amino acid sequences for pathway enzymes that may be used are given in Tables 1, 2, and 3, with SEQ ID NOs:1-48.

Methods for gene expression in yeasts are known in the art; specifically, basic yeast molecular biology protocols including transformation, cell growth, gene expression, gap repair recombination, etc. are described in *Methods in Enzymology*, Volume 194, *Guide to Yeast Genetics and Molecular and Cell Biology* (Part A, 2004, Christine Guthrie and Gerald R. Fink (Eds.), Elsevier Academic Press, San Diego, Calif. Expression of a gene in yeast typically requires a promoter, followed by the coding region of interest, and a transcriptional terminator, all of which are operably linked to provide expression cassettes. A number of yeast promoters can be used in constructing expression cassettes for genes encoding a butanol biosynthetic pathway, including, but not limited to constitutive promoters FBA, GPD, and GPM, and the inducible promoters GAL1, GAL10, and CUP1. Suitable transcriptional terminators include, but are not limited to FBAt, GPDt, GPMt, ERG10t, and GAL1t. For example, suitable promoters, transcriptional terminators, and the genes of a 1-butanol or isobutanol biosynthetic pathway may be cloned into *E. coli*-yeast shuttle vectors, as described in Example 2.

Typically used plasmids in yeast are shuttle vectors pRS423, pRS424, pRS425, and pRS426 (American Type Culture Collection, Rockville, Md.), which contain an *E. coli* replication origin (e.g., pMB1), a yeast 2μ origin of replication, and a marker for nutritional selection. The selection markers for these four vectors are His3 (vector pRS423), Trp1 (vector pRS424), Leu2 (vector pRS425) and Ura3 (vector pRS426). These vectors allow strain propagation in both *E. coli* and yeast strains. Typical hosts for gene cloning and expression include a yeast haploid strain BY4741 (MA Ta his3Δ1 leu2Δ0 met15Δ0 ura3Δ0) (Research Genetics, Huntsville, Ala., also available from ATCC 201388) and a diploid strain BY4743 (MA Ta/alpha his3Δ1/his3Δ1 leu2Δ0/leu2Δ0 lys2Δ0/LYS2 MET15/met15Δ0 ura3Δ0/ura3Δ0) (Research Genetics, Huntsville, Ala., also available from ATCC 201390). Construction of expression vectors for genes encoding butanol biosynthetic pathway enzymes may be performed by either standard molecular cloning techniques in *E. coli* or by the gap repair recombination method in yeast.

The gap repair cloning approach takes advantage of the highly efficient homologous recombination in yeast. Typically, a yeast vector DNA is digested (e.g., in its multiple cloning site) to create a "gap" in its sequence. A number of insert DNAs of interest are generated that contain a≥21 by sequence at both the 5' and the 3' ends that sequentially overlap with each other, and with the 5' and 3' terminus of the vector DNA. For example, to construct a yeast expression vector for "Gene X', a yeast promoter and a yeast terminator are selected for the expression cassette. The promoter and terminator are amplified from the yeast genomic DNA, and Gene X is either PCR amplified from its source organism or obtained from a cloning vector comprising Gene X sequence. There is at least a 21 by overlapping sequence between the 5' end of the linearized vector and the promoter sequence, between the promoter and Gene X, between Gene X and the terminator sequence, and between the terminator and the 3' end of the linearized vector. The "gapped" vector and the insert DNAs are then co-transformed into a yeast strain and plated on the medium containing the appropriate compound mixtures that allow complementation of the nutritional selection markers on the plasmids. The presence of correct insert combinations can be confirmed by PCR mapping using plasmid DNA prepared from the selected cells. The plasmid DNA isolated from yeast (usually low in concentration) can then be transformed into an *E. coli* strain, e.g. TOP10, followed by mini preps and restriction mapping to further verify the plasmid construct. Finally the construct can be verified by sequence analysis. Yeast transformants of positive plasmids are grown for performing enzyme assays to characterize the activities of the enzymes expressed by the genes of interest.

Fermentation Media

Fermentation media in the present invention must contain suitable carbon substrates. Carbon substrates can include, but are not limited to, monosaccharides such as fructose or galactose, oligosaccharides such as lactose, maltose, or sucrose, polysaccharides such as starch or cellulose or mixtures thereof and unpurified mixtures from renewable feedstocks such as cheese whey permeate, cornsteep liquor, sugar beet molasses, and barley malt. Other carbon substrates can include ethanol, lactate, succinate, or glycerol.

Additionally a carbon substrate can also be one-carbon substrates such as carbon dioxide, or methanol for which metabolic conversion into key biochemical intermediates has been demonstrated. In addition to one and two carbon substrates, methylotrophic organisms are also known to utilize a number of other carbon containing compounds such as methylamine, glucosamine and a variety of amino acids for metabolic activity. For example, methylotrophic yeasts are known to utilize the carbon from methylamine to form trehalose or glycerol (Bellion et al., Microb. Growth C1 Compd., [Int. Symp.], 7th (1993), 415-32, Editor(s): Murrell, J. Collin; Kelly, Don P. Publisher: Intercept, Andover, UK). Similarly, various species of Candida will metabolize alanine or oleic acid (Sulter et al., Arch. Microbiol. 153:485-489 (1990)). Hence it is contemplated that the source of carbon utilized in the present invention can encompass a wide variety of carbon containing substrates and will only be limited by the choice of organism.

Although it is contemplated that all of the above mentioned carbon substrates and mixtures thereof are suitable in the present invention, in some embodiments, a carbon substrates can be glucose, fructose, and sucrose, or mixtures of these with C5 sugars such as xylose and/or arabinose for yeast cells modified to use C5 sugars. Sucrose can be derived from renewable sugar sources such as sugar cane, sugar beets, cassava, sweet sorghum, and mixtures thereof. Glucose can be derived from renewable grain sources through saccharification of starch based feedstocks including grains such as corn, wheat, rye, barley, oats, and mixtures thereof. In addition, fermentable sugars can be derived from renewable cellulosic or lignocellulosic biomass through processes of pretreatment and saccharification, as described, for example, in co-owned and co-pending U.S. Patent Application Publication No. US 20070031918 A1, which is herein incorporated by reference. Biomass refers to any cellulosic or lignocellulosic material and includes materials comprising cellulose, and optionally further comprising hemicellulose, lignin, starch, oligosaccharides and/or monosaccharides. Biomass can also comprise additional components, such as protein and/or lipid. Biomass can be derived from a single source, or biomass can comprise a mixture derived from more than one source; for example, biomass can comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, animal manure, and mixtures thereof.

In addition to an appropriate carbon source, fermentation media must contain suitable minerals, salts, cofactors, buffers and other components, known to those skilled in the art, suitable for the growth of the cultures and promotion of the enzymatic pathway necessary for butanol production.

Culture Conditions

Typically cells are grown at a temperature in the range of about 20° C. to about 37° C. in an appropriate medium. Suitable growth media in the present invention are common commercially prepared media such as broth that includes yeast nitrogen base, ammonium sulfate, and dextrose as the carbon/energy source) or YPD Medium, a blend of peptone, yeast extract, and dextrose in optimal proportions for growing most *Saccharomyces cerevisiae* strains. Other defined or synthetic growth media may also be used and the appropriate medium for growth of the particular microorganism will be known by one skilled in the art of microbiology or fermentation science.

Suitable pH ranges for the fermentation are between pH 3.0 to pH 7.5, where pH 4.5.0 to pH 6.5 is preferred as the initial condition.

Fermentations may be performed under aerobic or anaerobic conditions, where anaerobic or microaerobic conditions are preferred.

The amount of butanol produced in the fermentation medium can be determined using a number of methods known in the art, for example, high performance liquid chromatography (HPLC) or gas chromatography (GC).

Industrial Batch and Continuous Fermentations

The present process employs a batch method of fermentation. A classical batch fermentation is a closed system where the composition of the medium is set at the beginning of the fermentation and not subject to artificial alterations during the fermentation. Thus, at the beginning of the fermentation the medium is inoculated with the desired organism or organisms, and fermentation is permitted to occur without adding anything to the system. Typically, however, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as CO2. Batch and Fed-Batch fermentations are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Mukund V., Appl. *Biochem. Biotechnol.*, 36:227, (1992), herein incorporated by reference.

Although the present invention is performed in batch mode it is contemplated that the method would be adaptable to continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using either batch, fed-batch or continuous processes and that any known mode of fermentation would be suitable. Additionally, it is contemplated that cells may be immobilized on a substrate as whole cell catalysts and subjected to fermentation conditions for 1-butanol production.

Methods for Butanol Isolation from the Fermentation Medium

The bioproduced butanol may be isolated from the fermentation medium using methods known in the art. For example, solids may be removed from the fermentation medium by centrifugation, filtration, decantation, or the like. Then, the butanol may be isolated from the fermentation medium, which has been treated to remove solids as described above, using methods such as distillation, liquid-liquid extraction, or membrane-based separation. Because butanol forms a low boiling point, azeotropic mixture with water, distillation can only be used to separate the mixture up to its azeotropic composition. Distillation may be used in combination with another separation method to obtain separation around the azeotrope. Methods that may be used in combination with distillation to isolate and purify butanol include, but are not limited to, decantation, liquid-liquid extraction, adsorption, and membrane-based techniques. Additionally, butanol may be isolated using azeotropic distillation using an entrainer (see for example Doherty and Malone, *Conceptual Design of Distillation Systems*, McGraw Hill, New York, 2001).

The butanol-water mixture forms a heterogeneous azeotrope so that distillation may be used in combination with decantation to isolate and purify the butanol. In this method, the butanol containing fermentation broth is distilled to near the azeotropic composition. Then, the azeotropic mixture is condensed, and the butanol is separated from the fermentation medium by decantation. The decanted aqueous phase may be returned to the first distillation column as reflux. The butanol-rich decanted organic phase may be further purified by distillation in a second distillation column.

The butanol may also be isolated from the fermentation medium using liquid-liquid extraction in combination with distillation. In this method, the butanol is extracted from the fermentation broth using liquid-liquid extraction with a suitable solvent. The butanol-containing organic phase is then distilled to separate the butanol from the solvent.

Distillation in combination with adsorption may also be used to isolate butanol from the fermentation medium. In this method, the fermentation broth containing the butanol is distilled to near the azeotropic composition and then the remaining water is removed by use of an adsorbent, such as molecular sieves (Aden et al. *Lignocellulosic Biomass to Ethanol Process Design and Economics Utilizing Co-Current Dilute Acid Prehydrolysis and Enzymatic Hydrolysis for Corn Stover*, Report NREL/TP-510-32438, National Renewable Energy Laboratory, June 2002).

Additionally, distillation in combination with pervaporation may be used to isolate and purify the butanol from the fermentation medium. In this method, the fermentation broth containing the butanol is distilled to near the azeotropic composition, and then the remaining water is removed by pervaporation through a hydrophilic membrane (Guo et al., *J. Membr. Sci.* 245, 199-210 (2004)).

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations is as follows: "s" means second(s), "min" means minute(s), "h" means hour(s), "psi" means pounds per square inch, "nm" means nanometers, "d" means day(s), "µL" means microliter(s), "mL" means milliliter(s), "L" means liter(s), "mm" means millimeter(s), "nm" means nanometers, "mM" means millimolar, "µM" means micromolar, "M" means molar, "mmol" means millimole(s), "µmol" means micromole(s)", "g" means gram(s), "µg" means microgram(s) and "ng" means nanogram(s), "PCR" means polymerase chain reaction, "OD" means optical density, "OD600" means the optical density measured at a wavelength of 600 nm, "kDa" means kilodaltons, "g" means the gravitation constant, "bp" means base pair(s), "kbp" means kilobase pair(s), "% w/v" means weight/volume percent, % v/v" means volume/volume percent, "HPLC" means high performance liquid chromatography, and "GC" means gas chromatography General Methods Materials and methods suitable for the maintenance and growth of yeast cultures are well known in the art. Techniques suitable for use in the following Examples may be found as set out in *Yeast Protocols, Second Edition* (Wei Xiao, ed; Humana Press, Totowa, N.J. (2006))). All reagents were obtained from Aldrich Chemicals (Milwaukee, Wis.), BD Diagnostic Systems (Sparks, Md.), Life Technologies (Rockville, Md.), Sigma Chemical Company (St. Louis, Mo.), or Teknova (Half Moon Bay, Calif.) unless otherwise specified.

YPD contains per liter: 10 g yeast extract, 20 g peptone, and 20 g dextrose.

Example 1

Improved Isobutanol Tolerance of *S. cerevisiae* by Deletion of PDR5 in Diploid Strain A homozygous diploid strain of *Saccharomyces cerevisiae* containing a PDR5 deletion mutation (strain #32409) was obtained from Research Genetics Inc. (Huntsville, Ala.). The deletion strain was made made as part of the *Saccharomyces* Genome Deletion Project described in Winzeler al. (Science, 285:901-906, (1999)).

Strain #32409, renamed S04, was tested for the growth yield as compared with the otherwise isogenic diploid parental strain BY4743 (ATCC #201390) in the presence of several concentrations of isobutanol, as listed in Table 1, in YPD medium. The inoculum OD600 was 0.01. The OD600 of each culture was measured after 24 hours incubation on a roller drum at 30° C. Triplicate cultures of each strain were tested. The average and standard deviation of the 24 hour growth yield measurements in each isobutanol concentration are given in Table 5.

TABLE 5

Average and standard deviations of triplicate measurements of OD600 of diploid yeast strains with PDR5 deletion and the otherwise isogenic parental strain after 24 hours incubation with isobutanol.

| [Isobutanol] % w/v | BY4743 | PDR5 mutant |
|---|---|---|
| 0 | 7.77 +/− 0.42 | 8.08 +/− 0.12 |
| 0.25 | 7.36 +/− 0.04 | 7.51 +/− 0.11 |
| 0.5 | 6.62 +/− 0.24 | 7.17 +/− 0.12 |
| 0.75 | 1.84 +/− 0.36 | 4.91 +/− 0.29 |
| 0.825 | 0.19 +/− 0.03 | 1.67 +/− 0.13 |
| 1 | 0.08 +/− 0.01 | 0.16 +/− 0.01 |

The growth yield for the strain with the PDR5 deletion was substantially greater than that of BY4743 at 0.75% and 0.825% w/v isobutanol (2.7-fold and 8.8-fold, respectively).

Thus, deletion of PDR5 in diploid *S. cerevisiae* conferred tolerance to isobutanol.

Example 2

Improved Isobutanol Tolerance of *S. cerevisiae* by Deletion of PDR5 in Haploid Strain A haploid strain of *Saccharomyces cerevisiae* containing a PDR5 deletion mutation (strain #2409) was obtained from Open Biosystems (Huntsville, Ala.) The deletion strain was made as part of the *Saccharomyces* Genome Deletion Project described in Winzeler al. (Science, 285:901-906, (1999)). Strain #2409 was tested for the growth yield as compared with the otherwise isogenic diploid parental strain, BY4741 (ATCC #201388), in the presence of several concentrations of isobutanol in YPD medium. The inoculum OD600 was 0.01. The OD600 of each culture was measured after 24 hours incubation on a roller drum at 30° C. Duplicate cultures of each strain were tested. The average and standard deviation of the 24 hour growth yield measurements in each isobutanol concentration are given in Table 6.

TABLE 6

Average and standard deviations of triplicate measurements of OD600 of haploid yeast strains with PDR5 deletion and the otherwise isogenic parental strain after 24 hours incubation with isobutanol.

| [Isobutanol] % w/v | BY4741 | PDR5 mutant |
|---|---|---|
| 0 | 8.93 +/− 0.26 | 9.16 +/− 0.06 |
| 0.75 | 2.68 +/− 0.07 | 4.71 +/− 0.53 |
| 0.875 | 0.692 +/− 0.04 | 2.45 +/− 0.42 |
| 1 | 0.09 +/− 0.02 | 0.76 +/− 0.13 |

The growth yield for the strain with the PDR5 deletion was substantially greater than that of BY4741 at 0.75%, 0.825% and 1% w/v isobutanol (1.8-fold, 3.5-fold, and 8-fold, respectively). Thus, deletion of PDR5 in haploid *S. cerevisiae* conferred tolerance to isobutanol.

Example 3

Improved 1-Butanol Tolerance of *S. cerevisiae* by Deletion of PDR5 in Diploid Strain The homozygous diploid strain of Example 1 containing a PDR5 deletion mutation (obtained from Research Genetics Inc, Huntsville, Ala.) was tested for the growth yield as compared with the otherwise isogenic diploid parental strain BY4743 in the presence of several concentrations of 1-butanol in YPD medium. The inoculum OD600 was 0.01. The OD600 of each culture was measured after 23 hours incubation on a roller drum at 30° C. Triplicate cultures of each strain were tested.

The average and standard deviation of the 23 hour growth yield measurements in each 1-butanol concentration are given in Table 7.

TABLE 7

Average and standard deviations of triplicate measurements of OD600 of diploid yeast strains with PDR5 deletion and the otherwise isogenic parental strain after 23 hours incubation with 1-butanol.

| [1-Butanol] % w/v | BY4743 | PDR5 mutant |
| --- | --- | --- |
| 0 | 12.9 +/− 0.10 | 13.1 +/− 0.20 |
| 0.625 | 2.38 +/− 0.25 | 3.27 +/− 0.23 |
| 0.75 | 0.30 +/− 0.03 | 0.40 +/− 0.02 |
| 0.875 | 0.22 +/− 0.01 | 0.27 +/− 0.01 |

The growth yield of the strain with the PDR5 deletion was substantially greater than that of BY4743 at 0.625%, 0.75% and 0.875% w/v 1-butanol (1.4-fold, 1.3-fold, and 1.2-fold, respectively). Thus, deletion of PDR5 in diploid *S. cerevisiae* conferred tolerance to 1-butanol.

Example 4

Prophetic

Production of Isobutanol in Recombinant *S. cerevisiae* with Engineered Isobutanol Pathway and Deletion of PDR5

The purpose of this prophetic example is to describe how to enhance isobutanol production in a yeast strain by combining an isobutanol biosynthetic pathway with a PDR5 deletion. The two starting strains are BY4741 and Strain #2409, which is BY4741 carrying a PDR5 deletion.

Construction of vectors pRS423::CUP1p-alsS+FBAp-ILV3 and pHR81::FBAp-ILV5-GPMp-kivD is described in US Patent Publication #US20070092957 A1, Example 17, which is herein incorporated by reference. pRS423::CUP1p-alsS+FBAp-ILV3 has a chimeric gene containing the CUP1 promoter (SEQ ID NO:61), the alsS coding region from *Bacillus subtilis* (SEQ ID NO: 41), and CYC1 terminator (SEQ ID NO:62) as well as a chimeric gene containing the FBA promoter (SEQ ID NO:63), the coding region of the ILV3 gene of *S. cerevisiae* (SEQ ID NO:47), and the ADH1 terminator (SEQ ID NO:64). pHR81::FBAp-ILV5+GPMp-kivD is the pHR81 vector (ATCC #87541) with a chimeric gene containing the FBA promoter, the coding region of the ILV5 gene of *S. cerevisiae* (SEQ ID NO 43), and the CYC1 terminator as well as a chimeric gene containing the GPM promoter (SEQ ID NO:65), the coding region from kivD gene of *Lactococcus* lactis (SEQ ID NO:35), and the ADH1 terminator. pHR81 has URA3 and leu2-d selection markers.

Plasmid vectors pRS423::CUP1p-alsS+FBAp-ILV3 and pHR81::FBAp-ILV5+GPMp-kivD are transformed into BY4741 or Strain #2409 using standard genetic techniques to yield the doubly transformed strains BY4741-iso and BY4741ΔPDR5-iso, respectively (*Methods in Yeast Genetics*, 2005, Cold Spring Harbor Laboratory Press, Cold Spring Harbor, N.Y.).

Aerobic cultures are grown in 250 ml flasks containing 50 ml synthetic complete media lacking histidine and uracil and supplemented with 2% glucose in an Innova4000 incubator (New Brunswick Scientific, Edison, N.J.) at 30° C. and 225 rpm. Low oxygen cultures are prepared by adding 45 mL of medium to 60 mL serum vials that are sealed with crimped caps after inoculation and kept at 30° C. Approximately 24 h and 48 h after induction with 0.03 mM $CuSO_4$ (final concentration), an aliquot of the broth is analyzed by HPLC (Shodex Sugar SH1011 column (Showa Denko America, Inc. NY) with refractive index (RI) detection and GC (HP-Innowax, 0.32 mm×0.25 μm×30 m; Agilent Technologies, Inc., Santa Clara, Calif.) with flame ionization detection (FID) for isobutanol content. Isobutanol is detected. More isobutanol is produced by BY4741ΔPDR5-iso than by BY4741-iso.

---

What is claimed is:

1. A recombinant yeast cell comprising:
   a) an isobutanol biosynthetic pathway, wherein the recombinant yeast cell comprises heterologous genes encoding an acetolactate synthase, an acetohydroxy acid isomeroreductase, an acetohydroxy acid dehydratase, a branched-chain keto acid decarboxylase, and a branched-chain alcohol dehydrogenase that perform the following substrate to product conversions:
      i) pyruvate to acetolactate catalyzed by the acetolactate synthase,
      ii) acetolactate to 2,3-dihydroxyisovalerate catalyzed by the acetohydroxy acid isomeroreductase,
      iii) 2,3-dihydroxyisovalerate to α-ketoisovalerate catalyzed by the acetohydroxy acid dehydratase,
      iv) α-ketoisovalerate to isobutyraldehyde catalyzed by the branched-chain keto acid decarboxylase,
      v) isobutyraldehyde to isobutanol catalyzed by the branched-chain alcohol dehydrogenase; and
   b) at least one genetic modification in an endogenous gene encoding a multidrug ATP-binding cassette transporter protein, wherein the multidrug ATP-binding cassette transporter protein has at least 95% sequence identity to SEQ ID NO:50, 52, 54, 56, or 58, wherein the at least one genetic modification decreases activity of the endogenous multidrug resistance ATP-binding cassette transporter protein, and;
      wherein the yeast cell has improved tolerance to isobutanol as compared to the corresponding yeast cell that lacks the at least one genetic modification of (b).

2. The yeast cell of claim 1 wherein the genetic modification substantially eliminates expression of the endogenous multidrug resistance ATP-binding cassette transporter protein.

3. A method for the production of isobutanol comprising growing the yeast cell of claim 1 under conditions wherein isobutanol is produced.

4. The method of claim 3, further comprising recovering the isobutanol.

5. A method for producing a recombinant yeast cell having increased tolerance to isobutanol comprising:
   a) providing a recombinant yeast cell comprising an isobutanol biosynthetic pathway, wherein the recombinant yeast cell comprises heterologous genes encoding an acetolactate synthase, an acetohydroxy acid isomeroreductase, an acetohydroxy acid dehydratase, a branched-chain keto acid decarboxylase and a branched-chain alcohol dehydrogenase that perform the following substrate to product conversions:
      i) pyruvate to acetolactate catalyzed by the acetolactate synthase,
      ii) acetolactate to 2,3-dihydroxyisovalerate catalyzed by the acetohydroxy acid isomeroreductase,
      iii 2,3-dihydroxyisovalerate to α-ketoisovalerate catalyzed by the acetohydroxy acid dehydratase,
      iv α-ketoisovalerate to isobutyraldehyde catalyzed by the branched-chain keto acid decarboxylase,
      v isobutyraldehyde to isobutanol catalyzed by the branched-chain alcohol dehydrogenase; and
   b) engineering the yeast cell of (a) to comprise at least one genetic modification in an endogenous gene encoding a multidrug ATP-binding cassette transporter protein, wherein the multidrug ATP-binding cassette transporter protein has at least 95% sequence identity to SEQ ID NO:50, 52, 54 56, or 58, wherein the at least one genetic modification decreases activity of the multidrug resistance ATP-binding cassette transporter protein, and wherein the yeast cell has improved tolerance to isobutanol as compared to the corresponding yeast cell that lacks the at least one genetic modification.

* * * * *